United States Patent [19]

Berthelon et al.

[11] Patent Number: 5,652,252

[45] Date of Patent: Jul. 29, 1997

[54] BENZOCYCLOHEPTENES

[75] Inventors: Jean Jacques Berthelon, Lyons; Michel Brunet, Toussieu; Marc Noblet, Lyons; Philippe Durbin, Villeurbanne; Daniel Guerrier, Sait-Genis-Laval; Trong Nghia Luong, Crepieux la Pape, all of France

[73] Assignee: Merck Patent Gesellschaft Mit Beschränkter Haftung, Darmstadt, Germany

[21] Appl. No.: 460,866

[22] Filed: Jun. 5, 1995

Related U.S. Application Data

[62] Division of Ser. No. 284,454, Aug. 5, 1994.

[30] Foreign Application Priority Data

Jul. 12, 1992 [FR] France ............... P.V. 92 14720

[51] Int. Cl.$^6$ .................. A61K 31/44; C07D 213/04
[52] U.S. Cl. .................. 514/357; 514/277; 514/337; 546/330; 546/344; 546/281.7
[58] Field of Search ............... 546/330, 344; 514/357, 277

[56] References Cited

U.S. PATENT DOCUMENTS

| | | | |
|---|---|---|---|
| 4,416,687 | 11/1983 | D'Amico et al. | 560/62 |
| 4,971,982 | 11/1990 | Attwood et al. | 514/337 |
| 5,112,839 | 5/1992 | Gericke et al. | 514/337 |

OTHER PUBLICATIONS

Polo et al. CA 112:55664, 1990.
DeBernardis et al. CA 104:148801, 1986.
Chemical Abstracts, vol. 93, No. 1, Jul. 7, 1980, Abstract No. 7854K, Jendrichovsky, et al. (CSA 180377).

*Primary Examiner*—Jane Fan
*Attorney, Agent, or Firm*—Millen, White, Zelano & Branigan, P.C.

[57] ABSTRACT

The subject of the invention is compounds of general formula:

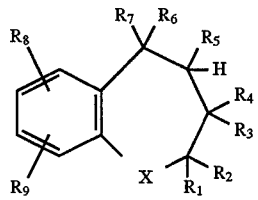

in which:

X represents O or CHR, $R_1$, $R_2$, $R_3$ and $R_4$, which are identical or different, represent a hydrogen atom or a $C_1$–$C_7$ alkyl group, it being possible for $R_1$ to additionally form a bond with R;

$R_5$ represents a hydrogen atom, a hydroxyl group or $R_5$, taken together with $R_7$, forms a bond or a>O; group;

$R_6$ represents a group of formula:

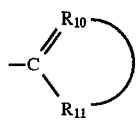

in which $R_{10}$ and $R_{11}$, taken together with the carbon atom to which they are attached, form a nitrogenous heterocyclic group, and their N-oxides and pharmaceutically acceptable salts.

These compounds are powerful activators of potassium channels.

9 Claims, No Drawings

BENZOCYCLOHEPTENES

This is a division of the U.S. application Ser. No. 08/284,454 filed Aug. 5, 1994.

The subject of the present invention is new heterocyclic compounds having a pharmacological activity in the activation of potassium channels.

Activators pf potassium channels or potassium agonists have the property of activating the potassium channels of the cell membrane by opening these channels or prolonging their opening. This results in transmembrane ionic movements and, inter alia, a decrease in free intracellular $Ca^{++}$ ions which causes relaxation of smooth muscle fibres.

This therapeutic potentiality makes it possible today for great hopes to be placed in potassium agonists. Among the most studied fields, arterial hypertension, angina and asthma are the most often mentioned. Large families of activators of potassium channels are already recognized for their relaxant properties.

A family of benzopyran derivatives has formed the subject of many publications in this field.

These compounds correspond to the following general formula A:

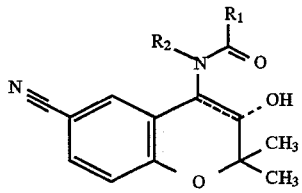

EP-0,076,075 describes compounds of general formula A, where

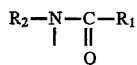

represents a pyrrolidone. DE-3,726,261 describes compounds of general formula A, where

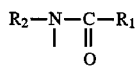

represents a pyridone.

Another benzopyran family corresponds to the formula B below; it is described in EP-0,298,452:

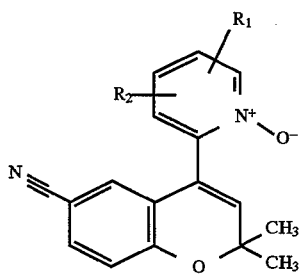

WO-89/11477 and EP-0,360,131 relate to benzoxepines of general formula C:

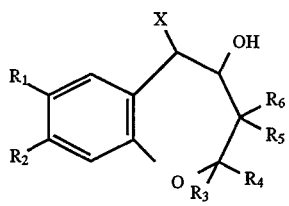

where X represents a nitrogenous ring connected via the nitrogen atom to the 5-position of the benzoxepines, such as a 2-oxo-1-pyrrolidinyl and 2-oxo-1-pyridyl group for the first and a 2-oxo-1-pyridyl group or a 4-fluorobenzoylamino group for the second.

$R_3$, $R_4$, $R_5$ and $R_6$ represent a hydrogen atom or a lower alkyl group and $R_1$ and $R_2$ a hydrogen atom or a nitrile, arylsulfonyl or nitro group.

Novel compounds possessing a benzocycloheptene or benzoxepine ring system, which show notable effects on the activation of potassium channels, have now been discovered.

The subject of the invention is compounds of general formula:

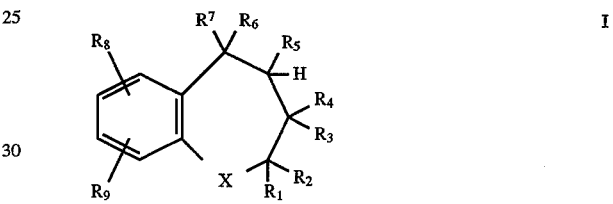

in which:

X represents O, or CHR, R being a hydrogen atom or R, taken together with $R_1$, forming a bond, $R_1$, $R_2$, $R_3$ and $R_4$, which are identical or different, represent a hydrogen atom or a $C_1$–$C_7$ alkyl group, it being possible for $R_1$ to additionally form a bond with R;

$R_5$ represents a hydrogen atom, a hydroxyl group or $R_5$, taken together with $R_7$, forms a bond or a >O; group;

$R_6$ represents a group of formula:

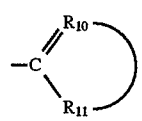

in which $R_{10}$ and $R_{11}$, taken together with the carbon atom to which they are attached, form an optionally aromatic mono- or bicyclic nitrogenous heterocyclic group having from 3 to 11 members, including 1 or 2 nitrogen atoms, optionally substituted on the carbon atoms by 1 to 7 groups chosen from hydroxyl, nitro, cyano. $C_1$–$C_7$ alkyl or $C_1$–$C_7$ alkoxy. it being possible for at least one of the nitrogen atoms of the heterocycle to be N-oxidized;

$R_7$ represents a hydrogen atom or a hydroxyl, $C_1$–$C_7$ alkoxy or $C_1$–$C_7$ acyloxy group or $R_5$ and $R_7$ together form a bond or a>O group;

$R_8$ and $R_9$, which are identical or different, represent a hydrogen or halogen atom, a hydroxyl, nitro, cyano, trifluoromethyl, trifluoromethoxy, pentafluoroethyl, $C_1$–$C_7$ alkyl, $C_1$–$C_7$ alkoxy, $C_1$–$C_7$ alkylthlo, $C_1$–$C_7$ acylthio. $C_1$–$C_7$ alkylsulfonyl or $C_1$–$C_7$ alkylsulfinyl group, a group of formulae:

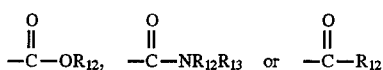

in which $R_{12}$ and $R_{13}$, which are identical or different, represent a hydrogen atom or a $C_1$-$C_7$ alkyl group, or $R_8$ and $R_9$ represent a $C_6$-$C_{10}$ aryl, ($C_6$-$C_{10}$)arylsulfonyl or ($C_6$-$C_{10}$)arylsulfinyl group, optionally substituted by one to six substituents chosen from halo, hydroxyl, nitro, cyano, carboxyl, carbamoyl, trifluoromethyl, trifluoromethoxy, pentafluoroethyl, $C_1$-$C_7$ alkyl, $C_1$-$C_7$ alkoxy, $C_1$-$C_7$ alkylthio, $C_1$-$C_7$ acylthio, $C_1$-$C_7$ alkylsulfonyl or $C_1$-$C_7$ alkylsulfinyl, or $R_8$ and $R_9$, which are identical or different, represent a heterocycle having from 3 to 11 members in the ring including 1 to 4 hetereoatoms, which are identical or different, chosen from O, S and N, optionally substituted by one to six substituents chosen from halo, hydroxyl, nitro, cyano, carboxyl, carbamoyl, trifluoromethyl, trifluoromethoxy, pentafluoroethyl, $C_1$-$C_7$ alkyl, $C_1$-$C_7$ alkoxy, $C_1$-$C_7$ alkylthio, $C_1$-$C_7$ acylthio, $C_1$-$C_7$ alkylsulfonyl or $C_1$-$C_7$ alkyl sulfinyl, or $R_8$ and $R_9$ together form a group $(CH_2)_n$, n being a number from 1 to 6, or $R_8$ and $R_9$ together form a heterocycle having from 3 to 11 members including 1 to 4 heteroatoms, which are identical or different, chosen from O, S and N, optionally substituted by one to six substituents chosen from halo, hydroxyl, nitro, cyano, carboxyl, carbamoyl, trifluoromethyl, trifluoromethoxy, pentafluoroethyl, $C_1$-$C_7$ alkyl, $C_1$-$C_7$ alkoxy, $C_1$-$C_7$ alkylthio, $C_1$-$C_7$ acylthio, $C_1$-$C_7$ alkylsulfonyl or $C_1$-$C_7$ alkylsulfinyl, and their N-oxides and their pharmaceutically acceptable salts.

"$C_1$-$C_7$ alkyl group" means the groups containing a linear or branched $C_1$-$C_7$ chain, especially the methyl, ethyl, propyl, isopropyl, butyl, tert-butyl, isobutyl, pentyl, hexyl and heptyl groups.

"$C_1$-$C_7$ alkoxy group" means the groups containing a linear or branched $C_1$-$C_7$ chain, especially the methoxy, ethoxy, propoxy, butoxy, pentoxy, hexyloxy and heptyloxy groups.

"$C_1$-$C_7$ acyloxy group" means the alkyl groups containing a linear or branched $C_1$-$C_6$ chain linked to a carbonyloxy functional group, especially the acetoxy and propionyloxy groups.

"$C_1$-$C_7$ alkylthio group" means the alkyl groups containing a linear or branched $C_1$-$C_7$ chain linked to a sulfur atom, especially the methylthio, ethylthio, propylthio, butylthio, pentylthio, hexylthio and heptylthio groups.

"$C_1$-$C_7$ alkylsulfonyl group" means the alkyl groups containing a linear or branched $C_1$-$C_7$ chain linked to a —$SO_2$— sulfonyl group, especially the methylsulfonyl, ethylsulfonyl, propylsulfonyl, butylsulfonyl, pentylsulfonyl, hexylsulfonyl and heptylsulfonyl groups.

"$C_1$-$C_7$ alkylsulfinyl group" means the alkyl groups containing a linear or branched $C_1$-$C_7$ chain linked to a —SO— sulfinyl group, especially the methylsulfinyl, ethylsulfinyl, propylsulfinyl, butylsulfinyl, pentylsulfinyl, hexylsulfinyl and heptylsulfinyl groups.

"$C_6$-$C_{10}$ aryl group" means the mono- or bicyclic carbocyclic aromatic groups, especially the phenyl, naphthyl or indenyl groups.

The term "halogen" means the fluorine, chlorine, bromine or iodine atoms.

The heterocycle containing from 3 to 11 atoms, including 1 to 4 hetereoatoms chosen from O, S and N, can be aromatic or nonaromatic, monocyclic or bicyclic, and is in particular a pyridyl, imidazolyl, furyl, tetrahydrofuryl, furazanyl, thienyl, aziridinyl, oxiranyl, azetidinyl, quinolyl, tetrahydroquinolyl and tetrazolyl group.

When $R_8$ and $R_9$ together form a heterocycle having from 3 to 11 members, including 1 to 4 identical or different hetereoatoms chosen from O, S and N, they represent, especially with the phenyl group to which they are, attached, a quinolyl, isoquinolyl, benzimidazolyl, benzofuryl, benzothienyl and benzoxadiazolyl group.

The $R_6$ group is in particular a 2-pyridyl, 2-pyridyl N-oxide, 3-pyridyl, 3-pyridyl N-oxide, 4-pyridyl, 3-hydroxy-4-pyridyl, 2-pyrimidyl, 2-pyrimidyl N-oxide, 6-pyrimidyl, 6-pyrimidyl N-oxide, 2-quinolyl, 2-quinolyl N-oxide, 1-isoquinolyl and 1-isoquinolyl N-oxide group, optionally substituted on the carbon atoms by 1 to 3 substituents chosen from hydroxyl, nitro, cyano, $C_1$-$C_7$ alkyl and $C_1$-$C_7$ alkoxy.

The physiologically acceptable salts of the compounds of formula I comprise the salts formed with metals such as sodium, potassium, calcium and magnesium or salts of organic acids such as oxalic, fumaric, maleic, citric, methanesulfonic and lactic acids.

The N-oxides of formula I are the compounds in which 1 or more of the nitrogen atoms of the $R_6$ group are oxidized.

The term "trans" used for the compounds which carry asymmetric carbon atoms in the rings shows that two substituents are found on either side of a central plane of the ring, and the term "cis" is applied for two substituents which are found on the same side of the same central plane of the ring.

The preferred compounds of general formula I are those in which X represents an oxygen atom.

Advantageously, $R_1$ and $R_2$ represent a hydrogen atom and/or $R_5$ represents a hydrogen atom.

Advantageously, $R_7$ is chosen from a hydrogen atom or the hydroxyl, methoxy and acetoxy group.

A first preferred family of compounds of the present invention correspond to the compounds of general formula II:

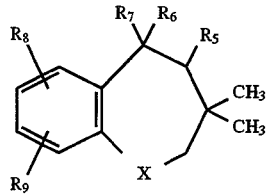

in which X represents O or CH—R, and R, $R_5$, $R_6$, $R_7$, $R_8$ and $R_9$ are as defined above.

Carbon atoms 4 and 5 of the formula II can together or independently represent a chiral centre. Derivatives such as optical isomers, racemates, cis or trans derivatives, enantiomers and diastereoisomers form part of the invention.

Among the preferred compounds of formula II, it is possible in particular to mention the following compounds:

3,3-dimethyl-5-(2-pyridyl N-oxide)-2,3,4,5-tetrahydro-1-benzoxepin-5-ol;

7-fluoro-3,3-dimethyl-5-(2-pyridyl N-oxide)-2,3,4,5-tetrahydro-1-benzoxepin-5-ol;

7-bromo-3,3-dimethyl-5-(2-pyridyl N-oxide)-2,3,4,5-tetrahydro 1-benzoxepin-5-ol;

8-bromo-3,3-dimethyl-5-(2-pyridyl N-oxide)-2,3,4,5-tetrahydro-1-benzoxepin-5-ol;

7-bromo-3,3-dimethyl-5-(3-pyridyl N-oxide)-2,3,4,5-tetrahydro 1-benzoxepin-5-ol;

5-acetyloxy-7-bromo-3,3-dimethyl-5-(2-pyridyl N-oxide)-2,3,4,5-tetrahydro-1-benzoxepine;

7-bromo-4,5-epoxy-3,3-dimethyl-5-(2-pyridyl N-oxide)-2,3,4,5-tetrahydro-1-benzoxepine;

7-bromo-5-methoxy-3,3-dimethyl-5-(2-pyridyl N-oxide)-2,3,4,5-tetrahydro-1-benzoxepine;

7- ethyl-3,3-dimethyl-5-(2-pyridyl N-oxide)-2,3,4,5-tetrahydro -1-benzoxepin-5-ol;

7-methoxy-3,3-dimethyl-5-(2-pyridyl N-oxide)-2,3,4,5-tetrahydro-1-benzoxepin-5-ol;

3,3-dimethyl-7-(1-methylpropyl)-5-(2-pyridyl N-oxide)-2,3,4,5-tetrahydro-1-benzoxepin-5-ol;

3,3 -dimethyl-5-(2-pyridyl N-oxide)-7-trifluoromethyl-2,3,4,5-tetrahydro-1-benzoxepin-5-ol;

3,3 -dimethyl-5-(2-pyridyl N-oxide)-7-trifluoromethoxy -2,3,4,5-tetrahydro-1-benzoxepin-5-ol;

3-dimethyl-7-phenyl-5-(2-pyridyl N-oxide)-2,3,4,5-tetrahydro-1-benzoxepin-5-ol;

8-chloro-7-fluoro-3,3-dimethyl-5-(2-pyridyl N-oxide) 2,3,4,5-tetrahydro-1-benzoxepin-5-ol;

3-dimethyl-5-(3-pyridyl N-oxide)-7-trifluoromethyl -2,3,4,5-tetrahydro-l-benzoxepin-5-ol;

8-dichloro-3,3-dimethyl-5-(2-pyridyl N-oxide) 2,3,4,5-tetrahydro-1-benzoxepin-5-ol;

6,8-dichloro-3,3-dimethyl-5-(2-pyridyl N-oxide) -2,3,4,5-tetrahydro-1-benzoxepin-5-ol;

7,8-dichloro-3,3-dimethyl-5-(3-pyridyl N-oxide) -2,3,4,5-tetrahydro-1-benzoxepin-5-ol;

7,8-dimethoxy-3,3-dimethyl-5-(2-pyridyl N-oxide) -2,3,4,5-tetrahydro-1-benzoxepin-5-ol;

7,9-dichloro-3,3-dimethyl-5-(2-pyrldyl N-oxide) -2,3,4,5-tetrahydro-1-benzoxepin-5-ol.

A second preferred family of compounds of the present invention correspond to the compounds of general formula III:

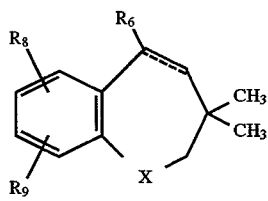

in which X represents O or

CH—R, and R, $R_6$, $R_8$ and $R_9$ are as defined above.

Among the preferred compounds of formula III, it is possible in particular to mention the following compounds:
3,3-dimethyl-5-(2-pyridyl N-oxide)-2,3-dihydro-1-benzoxepine;

7-fluoro-3,3-dimethyl-5-(2-pyridyl N-oxide)-2,3-dihydro-1-benzoxepine;

7-bromo-3,3-dimethyl-5-(2-pyridyl N-oxide)-2,3-dihydro-1-benzoxepine;

7-chloro-3,3-dimethyl-5-(2-pyridyl N-oxide)-2,3-dihydrobenzoxepine;

8-bromo-3,3-dimethyl-5-(2-pyridyl N-oxide)-2,3-dihydro-1-benzoxepine;

7,8-bromo-3,3-dimethyl-5-(3-pyridyl N-oxide)-2,3-dihydro-1-benzoxepine;

3,3,7-trimethyl-5-(2-pyridyl N-oxide)-2,3-dihydro-1-benzoxepine;

7-ethyl-3,3-dimethyl-5-(2-pyridyl N-oxide)-2,3-dihydro-1-benzoxepine;

3,3 -dimethyl-7-(1-methylpropyl)-5-(2-pyridyl N-oxide) -2,3-dihydro-1-benzoxepine;

7-isopropyl-3,3-dimethyl-5-(2-pyridyl N-oxide) -2,3-dihydro-1-benzoxepine;

7-methoxy-3,3-dimethyl-5-(2-pyridyl N-oxide)-2,3-dihydro1-benzoxepine;

3,3-dimethyl-5-(2-pyridyl N-oxide)-7-trifluoromethyl -2,3-dihydro-1-benzoxepine;

3,3-dimethyl-5-(2-pyridyl N-oxide)-8-trifluoromethyl -2,3- dihydro-1-benzoxepine;

3,3-dimethyl-5-(2-pyridyl N-oxide)-7-trifluoromethoxy -2,3-dihydro-1-benzoxepine;

3,3-dimethyl-7-methylsulfinyl-5-(2-pyridyl)-2,3-dihydro1-benzoxepine;

3,3-dimethyl-7-methylsulfonyl-5-(2-pyridyl)-2,3-dihydro-1-benzoxepine;

3,3-dimethyl-7-methylsulfonyl-5-(2-pyridyl N-oxide) -2,3-dihydro-1-benzoxepine;

8-cyano-3,3-dimethyl-5-(2-pyridyl N-oxide)-2,3-dihydrobenzoxepine;

7-cyano-3,3-dimethyl-5-(2-pyridyl N-oxide)-2,3-dihydro-1-benzoxepine;

3,3-dimethyl-5-(2-pyridyl N-oxide)-7-pentafluoroethyl-2,3-dihydro-1-benzoxepine; 3,3-dimethyl-7-phenyl-5-(2-pyridyl N-oxide)-2,3-dihydro -1-benzoxepine;

3,3-dimethyl-7-nitro-5-(4-nitro-2-pyridyl N-oxide) -2,3-dihydro-1-benzoxepine;

7,8-dichloro-3,3-dimethyl-5-(3-pyridyl N-oxide) -2,3-dihydro-1-benzoxepine;

6,8-dichloro-3,3-dimethyl-5-(2-pyridyl N-oxide) -2,3-dihydro-1-benzoxepine;

7,9-dichloro-3,3-dimethyl-5-(2-pyridyl N-oxide) -2,3-dihydro-1-benzoxepine;

8,9-dichloro-3,3-dimethyl-5-(2-pyridyl N-oxide) -2,3dihydro-1-benzoxepine;

7,8-dichloro-3,3-dimethyl-5-(2-pyridyl N-oxide) -2,3-dihydro-1-benzoxepine;

7,8-difluoro-3,3-dimethyl-5-(2-pyridyl N-oxide) -2,3-dihydro-1-benzoxepine;

9-ethyl-7-fluoro-3,3-dimethyl-5-(2-pyridyl N-oxide) -2,3-dihydro-1-benzoxepine;

8-cyano-3,3,7-trimethyl-5-(2-pyridyl N-oxide) -2,3-dihydro-1-benzoxepine;

7-cyano-3,3,8-trimethyl-5-(2-pyridyl N-oxide) -2,3-dihydro-1-benzoxepine;

7,8 -dimethoxy-3,3-dimethyl-5-(2-pyridyl N-oxide) -2,3-dihydro-1-benzoxepine;

8-chloro-7-fluoro-3,3-dimethyl-5-(2-pyridyl N-oxide) -2,3-dihydro-1-benzoxepine;

3,3-dimethyl-5-(2-pyridyl N-oxide)-2,3,7,8,9,10-hexahydro -1-naphth [2,3-b]oxepine;

8-cyano-3,3-dimethyl-1-(2-pyridyl N-oxide)-4,5-dihydro -H-benzo [4,3-f]cycloheptene;

3,3-dimethyl-5-(2-pyridyl N-oxide)-2,3-dihydro-1-benzoxepine; -7-carboxamide;

3,3-dimethyl-7-phenylsulfonyl-5-(2-pyridyl N-oxide) -2,3-dihydro-1-benzoxepine;

7-chloro-8-ethyl-3,3-dimethyl-5-(2-pyridyl N-oxide ) -2,3-dihydro-1-benzoxepine;

8-bromo-3,3-dimethyl-1-(2-pyridyl N-oxide)-3H-benzo [f]-cyclohepta-1,4-diene.

The compounds of the invention can be prepared by a process comprising:

a) the reaction of a ketone of general formula IV:

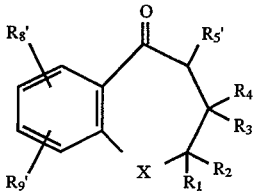

in which X, $R_1$, $R_2$, $R_3$ and $R_4$ are as defined above, and $R_5'$, $R_8'$ and $R_9'$ respectively represent the optionally protected $R_5$, $R_8$ and $R_9$ groups as defined above, with an organometallic compound of general formula:

in which $R_6'$ represents a group of formula:

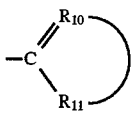

in which $R_{10}$ and $R_{11}$, taken together with the carbon atom to which they are attached, form an optionally aromatic, mono- or bicyclic nitrogenous heterocyclic group having from 3 to ,11 members, including 1 or 2 nitrogen atoms, and optionally substituted on the carbon atoms by 1 to 7 groups, optionally protected if necessary, chosen from hydroxyl, nitro, cyano, $C_1$–$C_7$ alkyl or $C_1$–$C_7$ alkoxy; and b) the deprotection of protected groups to produce a compound of general formula VI:

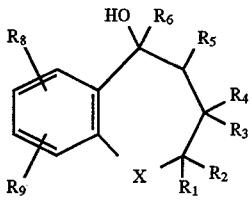

in which X, $R_1$, $R_2$, $R_3$, $R_4$, $R_5$, and $R_6$, and $R_8$ and $R_9$ are as defined above; and optionally either c1) the reaction of the compound of general formula VI thus obtained with a reactant of general formula VII:

in which $R_{14}$ represents a $C_1$–$C_7$ alkyl or $C_1$–$C_7$ acyl group and Y represents a leaving group, to produce a compound of general formula I in which $R_7$ represents a $C_1$–$C_7$ alkoxy or $C_1$–$C_7$ acyloxy group, respectively; or c2) the dehydration of the compound of general formula VI obtained in b) in the presence of an acid or of an acid chloride to produce a compound of following general formula I:

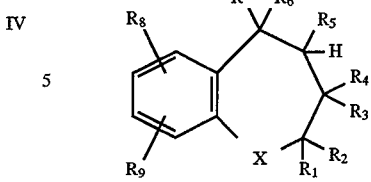

in which X, $R_1$, $R_2$, $R_3$, $R_4$, $R_5$, $R_6$, $R_8$ and $R_9$ are as defined above; and optionally d) the reaction of the compound of formula I obtained in Stage c2) with a peroxide to produce a compound of general formula I in which $R_5$ and $R_7$ together form a O group; and optionally e) the reaction of the compound of general formula VI obtained in Stage b) or of the compound of general formula I obtained in Stage c1), c2) or d) with an oxidizing agent to form a corresponding N-oxide compound; and/or optionally f) the reaction of the compound of general formula VI obtained in Stage b) or of the compound of general formula I obtained in Stage c1), c2) or d) with a pharmaceutically acceptable inorganic or organic acid to form a corresponding salt.

In the reaction of Stage a), a compound of formula IV as defined above is advantageously reacted with an organolithiumcompound of formula $LiR'_6$, $R'_6$ being as defined above.

The compounds of formula $LiR'_6$ can be prepared in a known way by a person skilled in the art, for example by reacting a compound of the formula $R'_6Br$, $R'_6$ being as defined above, with n-butyllithium in an organic solvent such as diethyl ether or tetrahydrofuran, optionally in the presence of hexamethylphosphoramide or of 1,3-dimethylimidazolidone at a temperature between –110° C. and the reflux temperature of the solvent, or of the mixture of solvents, for a time between 4 hours and 24 hours.

When the compounds of formula IV or V comprise OH groups, the latter are protected by a protective group of the hydroxyl functional group known to a person skilled in the art, for example an $SiMe_3$ or $SiMe_3tBu$ group.

The reaction of Stage a) takes place in an inert organic solvent, in particular diethyl ether, THF or hexane, at a temperature between –78° C. and –20° C., followed by the addition of a dilute acid to release the alcohol from the lithium alkoxide complex formed.

The deprotection reaction of Stage b) is carried out by an acid treatment in aqueous medium or by the use of fluoride (for example of tetrabutylammonium fluoride) in tetrahydrofuran at a temperature between –20° C. and 100° C., preferably 25° C.

In Stage c1), the leaving group Y is in particular a halogen atom or an alkyl- or arylsulfonyloxy group, in particular a mesyloxy or tosyloxy group.

Preferably, an acyl halide or an alkyl halide is used in the presence of a Lewis base in a solvent such as dimethylformamide.

The reaction for the removal of $H_2O$ in Stage c2) is advantageously carried out in acid medium and in the presence of an organic solvent, such as benzene, toluene or xylene, the acid being in particular para-toluene-sulfonic acid or sulfuric acid.

The acid can also consist of an acid chloride such as the chloride of methanesulfonic acid, in the presence of a solvent such as chloroform, dichloromethane or dichloroethane.

The reaction is advantageously carried out at the reflux temperature of the solvent.

The reaction of Stage d) takes place in the presence of a peroxide, in particular a peracid, such as peracetic acid, perbenzoic acid, perphthalic acid or 3-chloroperbenzoic acid. The amount of peroxide used can vary from 1 to 4 equivalents depending on the compound to be oxidized. The solvent used is preferably water, acetic acid or chlorinated solvents such as dichloromethane, chloroform or dichloroethane. The temperature of the reaction is advantageously between −20° C. and the reflux temperature of the solvent.

The reaction of Stage e) takes place in the presence of an oxidizing agent, in particular a peracid such as mentioned above (for example 3-chloroperbenzoic acid) in a solvent such as dichloromethane.

The ketones prepared are in particular:

7-bromo-3,3-dimethyl-2,3,4,5-tetrahydro-1-benzoxepin-one B.p.$_{(53.2\ Pa=0.4\ mm\ Hg)}$=117°–121° C.

7-chloro-3,3-dimethyl-2,3,4,5-tetrahydro-1-benzoxepin-5-one B.p.$_{(66.5\ Pa=0.5\ mm\ Hg)}$=80°–100° C.

7-cyano-3,3-dimethyl-2,3,4,5-tetrahydro-1-benzoxepin-5-one M.p.=114° C.

7-ethyl-3,3-dimethyl-2,3,4,5-tetrahydro-1-benzoxepin-5-one B.p.$_{(39.9\ Pa=0.3\ mm\ Hg)}$97°–104° C.

7-fluoro-3,3-dimethyl-2,3,4,5-tetrahydro-1-benzoxepin-5-one B.p.$_{(53.2\ Pa=0.4\ mm\ Hg)}$=102°–108° C.

7-isopropyl-3,3-dimethyl-2,3,4,5-tetrahydro-1-benzoxepin-5-one B.p.$_{(53.2\ Pa=0.4\ mm\ Hg)}$=112°–122° C.

7-methoxy-3,3-dimethyl-2,3,4,5-tetrahydro-1-benzoxepin-3-one B.p.$_{(33.25\ Pa=0.25\ mm\ Hg)}$=122°–126° C.

3,3-dimethyl-2,3,4,5-tetrahydro-1-benzoxepin-5-one B.p.$_{(103.4\ Pa=0.8\ mm\ Hg)}$=90° C.

3,3,7-trimethyl-2,3,4,5-tetrahydro-1-benzoxepin-5-one B.P.$_{(53.2\ Pa=0.4\ mm\ Hg)}$=90°–104° C.

7-(1-methylpropyl)-3,3-dimethyl-2,3,4,5-tetrahydro-1-benzoxepin-5-one B.p.$_{(53.2\ Pa=0.4\ mm\ Hg)}$=115°120° C.

7-methylthio-3,3-dimethyl-2,3,4,5-tetrahydro-1-benzoxepin-5-one B.p.$_{(79.8\ Pa=0.6\ mm\ Hg)}$=125°135° C.

7-pentafluoroethyl-3,3-dimethyl-2,3,4,5-tetrahydro-1-benzoxepin-5-one 7-phenyl-3,3-dimethyl-2,3,4,5-tetrahydro-1-benzoxepin-5-one B.p.$_{(26.6\ Pa=0.2\ mm\ Hg)}$=135°–140° C.

7-phenylthio-3,3-dimethyl-2,3,4,5-tetrahydro-1-benzoxepin-5-one 7-trifluoromethoxy-3,3-dimethyl-2,3,4,5-tetrahydro-1-benzoxepin-5-one B.p.$_{(2128\ Pa=16\ mm\ Hg)}$=135°–138° C.

7-trifluoromethyl-3,3-dimethyl-2,3,4,5-tetrahydro-1-benzoxepin-5-one B.p.$_{(133\ Pa=1\ mm\ Hg)}$=80°–100° C.

8-bromo-3,3-dimethyl-2,3,4,5-tetrahydro-1H-benzo[f]cyclo hepten-1-one M.p.=94° C.

8-bromo-3,3-dimethyl-2,3,4,5-tetrahydro-1-benzoxepin-5-one B.p.$_{(39.9\ Pa=0.3\ mm\ Hg)}$=108°–112° C.

8-trifluoromethyl-3,3-dimethyl-2,3,4,-tetrahydro-1-benzoxepin-5-one B.p.$_{(39.9\ Pa=0.3\ mm\ Hg)}$=85°–110° C.

9-bromo-3,3-dimethyl-2,3,4,5-tetrahydro-1-benzoxepin-5-one M.p.=86° C.

7-(2-methylpropyl)-3,3-dimethyl-2,3,4,5-tetrahydro-1-benzoxepin-5-one B.p.$_{(53.2\ Pa=0.4\ mm\ Hg)}$=128°–138° C.

7-(2-methylpropyl)-3,3-dimethyl-2,3,4,5-tetrahydro-1-benzoxepin-5-one B.p.=128°–136° C.

7-bromo-8-methyl-3,3-dimethyl-2,3,4,5-tetrahydro-1-benzoxepin-5-one B.p.$_{(53.2\ Pa=0.4\ mm\ Hg)}$=120°–130° C.

6,8-dichloro-3,3-dimethyl-2,3,4,5-tetrahydro-1-benzoxe-pin-5-one B.p.$_{(106.4\ Pa=0.8\ mm\ Hg)}$=120° C.

7,8-dichloro-3,3-dimethyl-2,3,4,5-tetrahydro-1-benzoxe-pin-5-one M.p.=94° C.

7,9-dichloro-3,3-dimethyl-2,3,4,5-tetrahydro-1-benzoxe-pin-5-one B.p.$_{(79.8\ Pa=0.6\ mm\ Hg)}$=120°–130° C. 8,9-dichloro-3,3-dimethyl-2,3,4,5-tetrahydro-1-benzoxe-pin-5-one 7-chloro-8-ethyl-3,3-dimethyl-2,3,4,5-tetrahydro-1-benzoxepin-5-one B.p.$_{(53.2\ Pa=0.4\ mm\ Hg)}$=108°–112° C.

7-chloro-3,3,8-trimethyl-2,3,4,5-tetrahydro-1-benzoxepin-5-one B.p.$_{(53.2\ Pa=0.4\ mm\ Hg)}$=115°–122° C.

7,8-difluoro-3,3-dimethyl-2,3,4,5-tetrahydro-1-benzoxepin-5-one M.p.=84° C.

7-fluoro-3,3-dimethyl-2,3,4,5-tetrahydro-1-benzoxepin-5-one B.p. M.p. =82° C.

7-fluoro-9-ethyl-3,3-dimethyl-2,3,4,5-tetrahydro-1-benzoxepin-5-one B.p.$_{(79.8\ Pa=0.6\ mm\ Hg)}$=102°–106° C.

7,8-dimethoxy-3,3-dimethyl-2,3,4,5-tetrahydro-1-benzoxepin-5-one M.p.=110° C.

7-methyl-8-bromo-3,3-dimethyl-2,3,4,5-tetrahydro-1-benzoxepin-5-one B.p.$_{(66.5\ Pa=0.5\ mm\ Hg)}$=125°–130° C.

7,8-dichloro-3,3-dimethyl-2,3,4,5-tetrahydro-1-benzoxepin-5-one M.p.=95° C.

3,3-dimethyl-2,3,4,5,7,8,9,10-octahydro-1-naphth[2,3-b]-oxepin-5-one B.p.$_{(53.2\ Pa=0.4\ mm\ Hg)}$=135°–150° C.

7-(2-methylpropyl)-3,3-dimethyl-2,3,4,5-tetrahydro-1-benzoxepin-5-one B.p.=128°–136° C.;

8-chloro-3,3-dimethyl-7-trifluoromethyl-2,3,4,5-tetrahydro-1-benzoxepin-5-one M.p.=80° C.;

7-bromo-8-chloro-3,3-dimethyl-2,3,4,5-tetrahydro-1-benzoxepin-5-one M.p.=94° C.;

3,3-dimethyl-8-phenylthio-2,3,4,5-tetrahydro-1H-benzo[f]cycloheptane-1-one;

7,8-dichloro-3,3-dimethyl-2,3,4,5-tetrahydro-1H-benzo[f]cycloheptane-1-one M.p.=74°.

8-bromo-4,4-dimethyl-2,3,4,5-tetrahydro-1H-benzo[f]cycloheptane-1-one;

8-bromo-3,3-dimethyl-2,3,4,5-tetrahydro-1H-benzo[f]cycloheptane-1-one M.p.=94° C.

The ketones of formula IV can be obtained by cyclization of the acids of formula VIII:

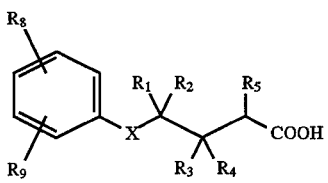

VIII in which x, $R_1$, $R_2$, $R_3$, $R_4$, $R_5$, $R_8$ and $R_9$ are as defined above, according to the method described by Guy Fontaine (Annalen der Chemie, 1968, Volume 3, No. 3, page 180) for the preparation of benzoxepines by cyclization of phenoxybutyric acids in the presence of phosphoric acid, alone or as a mixture with an organic solvent such as xylene, toluene or benzene, or by a Friedel-Crafts reaction from aluminium-chloride and the chlorides of the corresponding 4-phenoxybutanoic, 4-phenylthiobutanoic or 5-phenylpentanoic acids in a solvent such as $CS_2$ or nitrobenzene.

Other synthetic routes can also be used, in particular the Dieckmann condensation reactions.

The acids of general formula VIII can be prepared when X represents O by reaction of a compound of general formula IX:

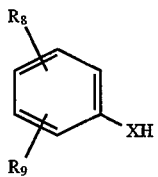

IX in which $R_8$ and $R_9$ are as defined above, with a compound of general formula X:

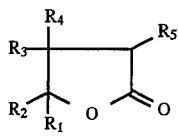

in which $R_1$, $R_2$, $R_3$, $R_4$ and $R_5$ are as defined above, according to the method of Reppe W. (Annalen der Chemie, 1955, book 596, p. 158–224).

The reaction takes place by heating in butanol in the presence of NaOH.

The acids of general formula VIII can also be prepared by reacting a phenol of formula IX as defined above with a compound of general formula XI:

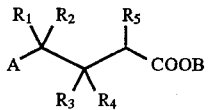

XI in which $R_1$, $R_2$, $R_3$, $R_4$ and $R_5$ are as defined above, A represents a halogen atom and B a lower alkyl or phenyl group, in a solvent such as DMF and in the presence of $K_2CO_3$ or in acetone in the presence of $K_2CO_3$ and KI.

When X represents CHR, the acids of general formula VIII can be prepared according to Mathut K. C. and Singh V. P. (Proc. Natl. Acad. Sci. India. Sect A, 1981, 51 (2), p. 177 and 180), or according to Klaus Michael and Mohr Peter (EP-0,315,071) by:

a) reaction of a compound of formula XII:

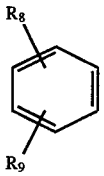

XII with a compound of formula XIII or XIV:

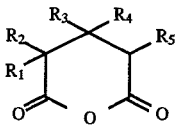

XIII

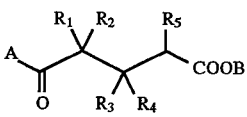

XIV in which $R_1$, $R_2$, $R_3$, $R_4$ and $R_5$ are as defined above, A represents a halogen atom and B a lower alkyl or phenyl group, in the presence of $AlCl_3$ in a solvent like $CS_2$ or nitrobenzene, or in the absence of solvent, to produce a compound of general formula XV:

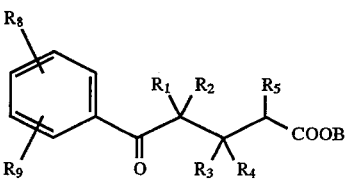

XV in which $R_1$, $R_2$, $R_3$, $R_4$ and $R_5$, $R_6$, $R_9$ and B are as defined above;

b) hydrolysis of the compound of general formula XV thus obtained either in basic medium such as NaOH, KOH, $NaHCO_3$, for example in water/alcohol medium, or in acid medium:

to produce a compound of general formula XVI:

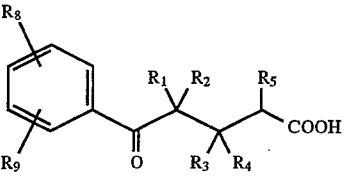

XVI in which $R_1$, $R_2$, $R_3$, $R_4$, $R_5$, $R_8$ and $R_9$ are as defined above, and c) reduction of the carbonyl functional group of the compound of formula XVI according to the Wolff-Kishner reaction in the presence of an excess of hydrazine and of strong base, for example potassium hydroxide, in diethylene glycol or polyethylene glycol at high temperature.

The acids of formula VIII prepared are in particular:

4-phenoxy-3,3-dimethylbutanoic acid, B.p.$_{(13.3\ Pa=0.1\ mm\ Hg)}$=130° C.;

4-(4-bromophenoxy)-3,3-dimethylbutanoic acid, B.p.$_{(53.2\ Pa=0.4\ mm\ Hg)}$=154°162° C.;

4-(4-chlorophenoxy)-3,3-dimethylbutanoic acid, B.p.$_{(53.2\ Pa=0.4\ mm\ Hg)}$=130°–145° C.;

4-(4-fluorophenoxy)-3,3-dimethylbutanoic acid, B.p.$_{(53.2\ Pa=0.4\ mm\ Hg)}$=128°–134° C.;

4-(4-methylphenoxy)-3,3-dimethylbutanoic acid, B.p.$_{(53.2\ Pa=0.4\ mm\ Hg)}$=130°–136° C.;

4(4-ethylphenoxy)-3,3-dimethylbutanoic acid, B.p.$_{(53.2\ Pa=0.4\ mm\ Hg)}$=132°136° C.;

4-(4-isopropylphenoxy)-3,3-dimethylbutanoic acid, B.p.$_{(53.2\ Pa=0.4\ mm\ Hg)}$=130°–142° C.;

4-[4-(1-methylpropyl) phenoxy]-3,3-dimethylbutanoic acid, B.p.$_{(53.2\ Pa=0.4\ mm\ Hg)}$=155°–165° C.;

4-(4-methoxyphenoxy)-3,3-dimethylbutanoic acid, M.p.=69° C.

4-(4-trifluoromethoxyphenoxy)-3,3-dimethylbutanoic acid, B.p.$_{(53.2\ Pa=0.4\ mm\ Hg)}$=100°–120° C.;

4-(4-methylthiophenoxy)-3,3-dimethylbutanoic acid, B.p.$_{(106.4\ Pa.\ =0.8\ mm\ Hg)}$=150°170° C.;

4-(4-phenylphenoxy)-3,3-dimethylbutanoic acid, M.p.=124° C.

4-(3-bromophenoxy)-3,3-dimethylbutanoic acid, B.p.$_{(106.4\ Pa=0.4\ mm\ Hg)}$=140°–160 ° C.;

4-(3,5-dichlorophenoxy)-3,3-dimethylbutanoic acid, B.p.$_{(53.2\ Pa=0.4\ mm\ Hg)}$=130°–150° C.;

4-(3,4-dichlorophenoxy)-3,3-dimethylbutanoic acid, M.p.=66° C.;

4-(2,4-dichlorophenoxy)-3,3-dimethylbutanoic acid, B.p.$_{(66.5\ Pa=0.5\ mm\ Hg)}$=150°–160° C.;

4-(2,3-dichlorophenoxy) -3,3-dimethylbutanoic acid, B.p.$_{(66.5\ Pa=0.5\ mm\ Hg)}$=130°–160° C.;

4- (3,4-difluorophenoxy) -3,3-dimethylbutanoic acid, B.p.$_{(53.2\ Pa=0.4\ mm\ Hg)}$=110°134° C.;

4-(3-chloro-4-fluorophenoxy)-3,3-dimethylbutanoic acid, B.p.$_{(53.2\ Pa=0.4\ mm\ Hg)}$=130°145° C.;

4-(2-ethyl-4-fluorophenoxy)-3,3-dimethylbutanoic acid, B.p.$_{(53.2\ Pa=0.4\ mm\ Hg)}$=123°–126° C.;

4-(3,4-dimethoxyphenoxy)-3,3-dimethylbutanoic acid, B.p.$_{(53.2\ Pa=0.4\ mm\ Hg)}$=150°–170° C.;

4-(4-bromo-3-methylphenoxy)-3,3-dimethylbutanoic acid, B.p.$_{53.2\ Pa=0.4\ mm\ Hg)}$=130°–135° C.;

4-(3-bromo-4-methylphenoxy)-3,3-dimethylbutanoic acid, B.p.$_{(53.2\ Pa=0.4\ mm\ Hg)}$=155°–160° C.;

4-(5,6,7,8-tetrahydro-2-naphthyloxy)-3,3-dimethylbutanoic acid, M.p.=85° C.;

4-[4-(2-methylpropyl)phenoxy]-3,3-dimethylbutanoic acid,

4-B.p.$_{(66.5\ Pa=0.4\ mm\ Hg)}$=160°–180° C.; (4-chloro-3-ethylphenoxy)-3,3-dimethylbutanoic acid, B.p.$_{(53.2\ Pa=0.4}$mm Hg)=160°–166° C.;

4-(4-chloro-3-methylphenoxy)-3,3-dimethylbutanoic acid, B.p.$_{(53.2\ Pa=0.4\ mm\ Hg)}$=150°–158° C.;

4-(4-bromo-3-chlorophenoxy)-3,3-dimethyl-butanoic acid, B.p.$_{(53.2\ Pa=0.4\ mm\ Hg)}$=150°170° C.;

5-(4-bromophenyl)-3,3-dimethylpentanoic acid, M.p.=72° C.; 5-(3,4-dichlorophenyl)-3,3-dimethylpentanoic acid;

5-(4-bromophenyl)-4,4-dimethylpentanoic acid, M.p.=106°–108° C.

The compounds of the invention have excellent properties in the activation of potassium channels and have a powerful relaxant effect on smooth musculature. Consequently, they can be used as bronchodilators in disorders of the respiratory system, and in particular against asthma and obstruction of the upper airways. They also have an advantage in the control of hypertension and in the case of disorders of the contraction of the smooth musculature of the gastrointestinal tract, of the uterus, of the urinary tract, and in incontinence phenomena. They are useful in the case of cardiovascular disorders other than hypertension, in particular cardiac insufficiency, angina pectoris, cerebral and peripheral vascular pathologies and pulmonary hypertension. These compounds are additionally active in the treatment of alopecia.

The "potassium channel activating" activity was measured by the rate of exit of rubidium-86 from tracheal smooth muscle cell according to the method described by Allen, S. L., Br. J. Pharmac., 1986, 87, p. 117–127 and 89, p. 395–405.

Rate of the efflux of rubidium-86 in in vitro guinea pig trachea:

Male guinea pigs weighing 250 to 600 g are stunned and exsanguinated by sectioning the jugular. The trachea is rapidly freed and cleaned in situ. The parts removed are placed on hold in an oxygenated modified Krebs-Henseleit (M.K.H.) solution. When all the tracheas are removed each is enriched in smooth muscle. The trachea is placed in a crystallizing dish containing the M.K.H. and a stream of $O_2/CO_2$ at 37° C. Two longitudinal incisions are carefully made on both sides of the muscle strip at 1 mm from the latter. The tracheae are then equilibrated in a beaker containing 30 ml of M.K.H. for 30 minutes, after which the rubidium-86 radioactive charge is added. A constant and sustained gaseous flow rate is maintained throughout the manipulation.

The beaker is then replaced by another containing 25 ml of oxygenated M.K.H. and 125 microcuries of $^{86}$Rb for 3 hours. The tracheas are washed twice in succession in a beaker containing approximately 100 ml of M.K.H. for 3 minutes.

The tracheae are introduced individually into a series of 10 ml disposable tubes. The latter are filled, 30 seconds before immersion of the tracheae, with 4 ml of oxygenated M.K.H. There are then carried out an immersion of the tracheae for 5 minutes and 5 rinsings of 10 minutes and then efflux periods of 3 minutes. A first group of tubes are used for estimating the base efflux: they contain 10 µl of pure DMSO plus 4 ml of M.K.H. A second group of tubes makes it possible to bring the sample into contact with a concentration of product to be tested lasting seven periods of 3 minutes. The products are used in the form of mother solutions containing 40.1 mmol of pure DMSO, then diluted in the same solvent and introduced in the set amount of 10 µl per 4 ml of M.K.H. The counting is carried out by the Cerenkov effect.

The effective concentration of the product which increases the base efflux rate by 25% ($EC_{25\%}$) is determined.

The efflux rate of the tracer is expressed as percentage of release per minute with respect to the total amount of tracer at the time under consideration.

The $EC_{25\%}$ is calculated by linear regression from the relationship: Maximum efflux in the presence of product with respect to the base efflux as a function of the logarithm of the concentration.

The results obtained with representative pounds of the invention are reported in Table I below.

TABLE I

Results of the activating activity of the compounds of the invention for potassium channels

| Compound | Efflux of $^{86}$Rb $EC_{25\%}$ (µmol) |
|---|---|
| 91 | 1.1 |
| 100 | 2.0 |
| 104 | 0.7 |
| 109 | 1.8 |
| 111 | 0.8 |

The bronchodilating activity was measured in vivo by the method of Konzett H. and Rossler R. (Arch. Exp. Pathol. Pharmak., 1940, 195, p. 71 to 74) and Duhault J. et al. (Arzneim. Forsch./Drug. res., 1987, 37, p. 1353 to 1362).

Measurement of the bronchodilating activity:

Dukin-Hartley guinea pigs (400–500 g) are prepared according to the methodology described by Konzett and Rossler. The animals are anaesthetized by an intraperitoneal injection of urethane (1.5 g/kg) and a tracheotomy is prepared for artificial respiration (45 cycles/min; respiratory volume 10 ml/kg).

The animal is connected to a respiratory pump, which is adjusted to deliver a volume of 1 ml per 100 g of body weight of the guinea pig. It is connected to a recorder via a pressure sensor.

A catheter is placed in the jugular for the I.V. injections.

An I.V. injection of gallamine and propanolol is carried out. After stabilizing the pulmonary pressure for 30 minutes, an I.V. injection of histamine is carried out every 10 minutes until reproducibility is achieved; at that point, the test product is injected 10 minutes after the last spasm. Histaxnine is tested 5 minutes and 15 minutes after the injection of the product and the effective dose for a 50 % inhibition is calculated.

The results obtained with representative compounds of the invention are reported in Table II below.

TABLE II

Results of the bronchodilating activity of the compounds of the invention

| Compound | Bronchospam $ED_{50}$ mg/kg | |
|---|---|---|
| | at 5 min | at 15 min |
| 91 | 0.100 | — |
| 100 | 0.069 | 0.101 |
| 104 | 0.038 | 0.210 |
| 109 | 0.086 | 0.331 |
| 111 | 0.049 | 0.100 |
| 114 | 0.040 | 0.300 |
| 118 | 0.150 | 0.200 |
| 119 | 0.310 | 0.530 |

The compounds of the invention are active in man and animals, in particular in mammals, in particular in dogs, guinea pigs, rabbits, rats and mice.

The compounds of the invention are non-toxic.

Another subject of the invention is a pharmaceutical composition comprising, as active ingredient, a compound according to the invention as defined above, in combination with a pharmaceutically acceptable vehicle.

These pharmaceutical compositions are used in oral, intravenous, intraarterial, cutaneous or intestinal administration or as an aerosol. Moreover, these new products have a long-lasting action, whatever the mode of administration.

The products of the general formula I will be combined in the pharmaceutical form with excipients, flavours and dyes, which are suitable for forming, for example, tablets, which can additionally be provided in the liposomal, microcapsule or nanocapsule form, or in the form of coated tablets, gelatin capsules, solutions, injectable solutions, suppositories, aerosols or creams. The excipients used can be, for example, microcrystalline cellulose, lactose, polyvidone, starch sodium glycolate, talc or magnesium stearate. The excipients for the liposomal or microcapsule forms can be poly (alkyl cyano-acrylates) or phospholipids.

The coating of the tablets can be carried out with additives such as hydroxypropyl methylcellulose, various acrylic polymers, propylene glycol and titanium dioxide.

The preparations for oral administration can contain artificial flavours and sweeteners such as sugar or aspartame.

The injectable solution preparations will be made up with water which will contain stabilization agents, solubilization agents, such as sodium chloride, mannitol and sorbitol, and/or buffers necessary for the injectable solutions.

The preparations for suppositories can use excipients such as semi-synthetic glycerides.

The preparations for creams will be made, inter alia, by the addition of nonionic surface-active agents.

The preparations for aerosol administration can be made from the micronized active principle, in combination with a surface-active agent such as sorbitan trioleate, in a carrier gas such as CFC-11 and -12 or any other substituted carrier gas.

The compounds of the invention can also be used in combination with any other substance of therapeutic use, for example diuretics, beta-blockers, PAF-acether antagonists, $TxA_2$ antagonists, converting enzyme inhibitors, beta-adrenergic inhibitors and anti-arrhythmics.

The daily doses of active principle, administered once or a number of times, can be between 0.0001 and 100 mg/kg of body weight and preferably between 0.001 and 1 mg/kg. However, these limits can be exceeded in the event of necessity.

A formulation example of a tablet and of a gelatin capsule according to the invention will be given below.

| Tablet formulation example: | |
| --- | --- |
| Compound of formula 91 | 5 mg |
| Microcrystalline cellulose | 90 mg |
| Lactose | 144 mg |
| Starch sodium glycolate | 10 mg |
| Magnesium stearate | 1 mg |
| | 250 mg |
| Gelatin capsule formulation example: | |
| Compound of formula 111 | 10 mg |
| Microcrystalline cellulose | 109 mg |
| Lactose | 100 mg |
| Starch | 30 mg |
| Magnesium stearate | 1 mg |
| | 250 mg |

The following examples illustrate the invention is a non-limiting way.

In the proton nuclear magnetic resonance ($^1$H NMR) data, the following abbreviations have been used: ppm for part per million; s for singlet; d for doublet; t for triplet; q for quartet; b for broad; J for the couplings expressed in hertz; dd for double doublet.

EXAMPLE 1

7-Bromo-3,3-dimethyl-5-(2-pyridyl)-2,3,4,5-tetrahydro-1-benzoxepin-5-ol $C_{17}H_{18}BrNO_2$ MM=348.239

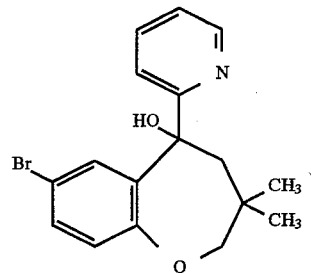

Formula 1

A solution of n-butyllithium (1.6 mol/l) in hexane (93 ml, 0.15 mol) and of anhydrous diethyl ether (200 ml) is cooled to −78° C. under a dry nitrogen stream. A solution of 2-bromopyridine (14.3 ml, 0.15 mol) in diethyl ether (100 ml) is added over 1 hour and the mixture is then stirred for a further 0.5 hour at −78° C.

A solution of 7-bromo-3,3-dimethyl-2,3,4,5-tetrahydro-1-benzoxepin-5-one (13.5 g, 0.05 mol) in dry benzene (150 ml) is added over 1 hour at −78° C. Stirring is continued for 1.5 hours at −78° C. and 1 hour at −15° C. Ice-cold water (100 ml) is then added via a dropping funnel and extraction is carried out with diethyl ether. The organic phase is washed with water and dried over anhydrous sodium sulfate. The solution is concentrated under reduced pressure (brown oil).

[yellow solid; 14 g; M.p.=124°–128° C.; hexane; 80%]IR in cm$^{-1}$: 3340, 2950, 1595, 1580 $^1$H NMR (CDCl$_3$) in ppm: 8.50 (1H, dd, J=4.5 Hz), 7.20 (6H, m), 5.75 (1H, s), 4.08 (1H, d, J=11 Hz), 3.80 (1H, d, J=11 Hz), 2.34 (1H, d, J=13.5 Hz), 1.66 (1H, d, J=13.5 Hz), 1.06 (3H, s), 0.86 (3H, s).

| | Elemental analysis | | | | |
| --- | --- | --- | --- | --- | --- |
| | C | H | Br | N | O |
| % Found | 58.56 | 5.28 | 22.95 | 4.02 | |
| % Calculated | 58.63 | 5.21 | 22.95 | 4.02 | 9.19 |

By using the same process, the following compounds are prepared.

7-Chloro-3,3-dimethyl-5-(2-pyridyl)-2,3,4,5-tetrahydro-1-benzoxepin-5-ol $C_{17}H_{18}ClNO_2$ MM=303.788

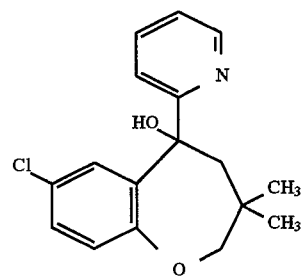

Formula 2

[flash chromatography: CH$_2$Cl$_2$; M.p.=118° C.; hexane 83%]IR in cm$^{-1}$: 3340, 2950, 1595, 1570.

$^1$H NMR (CDCl$_3$) in ppm: 8.54 (1H, dd, J=1.5 Hz), 7.22 (6H, m), 5.75 (1H, s), 4.11 (1H, d, J=11 Hz), 3.85 (1H, d, J=11 Hz), 2.37 (1H, d, J=13.5 Hz), 1.71 (1H, d, J=13.5 Hz), 1.07 (3H, s), 0.88 (3H, s). 7-Fluoro-3,3-dimethyl-5-(2- pyridyl)-2,3,4,5-tetrahydro-1-benzoxepin-5-ol C₁₇H₁₈FNO₂ MM=287.333

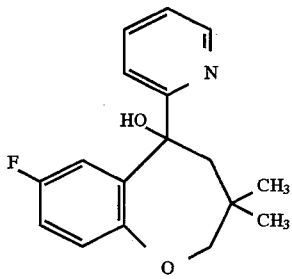

Formula 3

[M.p.=110° C.; hexane; 64%]IR in cm⁻¹: 3320, 2960, 1595, 1580. ¹H NMR (CDCl₃) in ppm: 8.50 (1H, dd, J=4.5 Hz), 7.05 (6H, m), 5.65 (1H, s), 4.05 (1H, d, J=12 Hz), 3.80 (1H, d, J=12 Hz), 2.42 (1H, d, J =14 Hz), 1.75 (1H, d, J=14 Hz), 1.09 (3H, s), 0.88 (3H, s). 3,3-Dimethyl-5-(2-pyridyl)-2,3,4,5-tetrahydro-1-benzoxepin-5-ol C₁₇H₁₉NO₂ MM=269.343

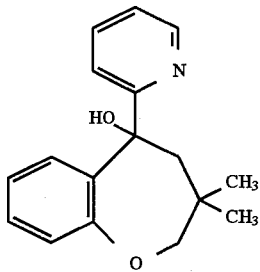

Formula 4

[chromatography with silica gel and CH₂Cl₂; oil; 87%]IR in cm⁻¹: 3360, 2950, 1595, 1580 ¹H NMR (CDCl₃) in ppm: 8.46 (1H, dd, J=4.5 Hz), 7.15 (6H, m), 5.75 (1H, m), 4.15 (1H, d, J=12 Hz), 3.85 (1H, d, J=12 Hz), 2.37 (1H, d, J=13.5 Hz), 1.70 (1H, d, J=13.5 Hz), 1.10 (3H, s), 0.92 (3H, s). 3,3,7-Trimethyl-5-(2-pyridyl)-2,3,4,5-tetrahydro-1-benzoxepin-5-ol

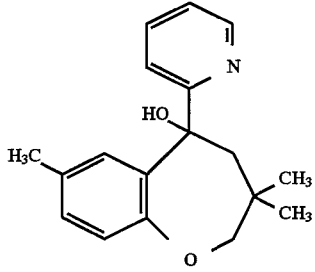

Formula 5

[M.p.=126° C.; hexane; 66%]IR in cm⁻¹: 3310, 2960, 1595, 1575, 1500 ¹H NMR (CDCl₃) in ppm: 8.52 (1H, dd, J=4.5 Hz), 7.05 (6H, m), 5.63 (1H, m), 4.07 (1H, d, J=11 Hz), 3.85 (1H, d, J=11 Hz), 2.41 (1H, d, J=13.5 Hz), 2.10 (3H, s), 1.74 (1H, d, J=13.5 Hz), 1.09 (3H, s), 0.88 (3H, s). 7-Ethyl-3,3-dimethyl-5-(2-pyridyl)-2,3,4,5-tetrahydro-1-benzoxepin-5-ol C₁₉H₂₃NO₂ MM=297.396

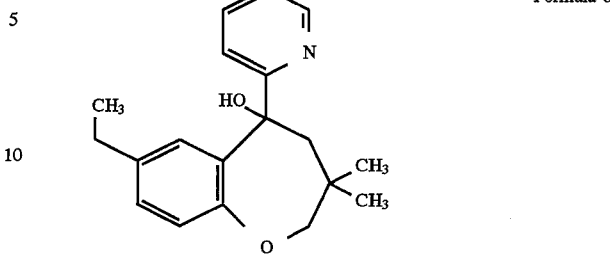

Formula 6

[chromatography with silica gel and dichloromethane/methanol: 98/2; M.p.=84° C.; hexane; 76%]IR in cm⁻¹: 3350, 2970, 1595, 1565, 1500 7-Isopropyl-3,3-dimethyl-5-(2-pyridyl)-2,3,4,5-tetra-hydro-1-benzoxepin-5-ol C₂₀H₂₅NO₂ MM=311.423

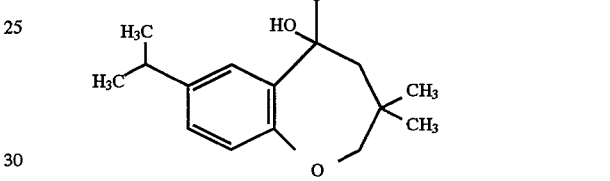

Formula 7

[M.p.=72° C.; crystallizes from pentane; 72%]IR in cm⁻¹: 3310, 2960, 1585, 1495 ¹H NMR (CDCl₃) in ppm: 8.50 (1H, m) , 7.53 (1H, m) , 6.91 (5H, m), 5.63 (1H, s), 4.10 (1H, d, J=11 Hz), 3.82 (1H, d, J=11 Hz), 2.68 (1H, m), 2.38 (1H, d, 13.5 Hz), 1.70 (1H, d, 13.5 Hz), 1.02 (12H, m). 3,3-Dimethyl-7-(1-methylpropyl)-5-(2-pyridyl) -2,3,4,5-tetrahydro-1-benzoxepin-5-ol C₂₁H₂₇NO₂ MM=325.450

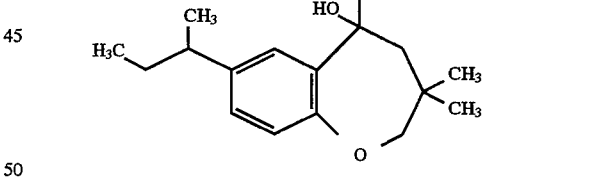

Formula 8

[chromatography with silica gel and dichloromethane/ heptane: 80/20; 33 %]IR in cm⁻¹: 3370, 2970, 1600, 1580, 1500 ¹H NMR (CDCl₃) in ppm: 8.46 (1H, m) , 7.05 (6H, m) , 5.65 (1H, s), 4.09 (1H, d, J=11 Hz), 3.79 (1H, d, J=11 Hz), 2.35 (1H, d, J=13.5 Hz), 2.22 (1H, m), 1.65 (1H, d, J=13.5 Hz), 1.06 (14H, m). 7-Methoxy-3,3-dimethyl-5-(2-pyridyl) -2,3,4,5-tetrahydro -1-benzoxepin-5-ol C₁₈H₂₁NO₃ MM=299.369

Formula 9

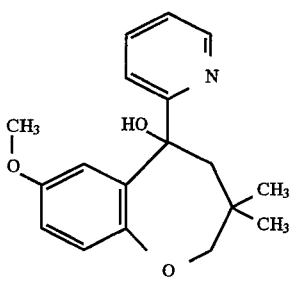

[chromatography with silica gel and dichloromethane/methanol: 95/5; M.p. 98° C.; hexane; 68%]IR in cm⁻¹: 3270, 2970, 1595, 1575, 1500 ¹H NMR (CDCl₃) in ppm: 8.50 (1H, dd, J=4.5 Hz), 7.05 (6H, m), 5.53 (1H, s), 3.89 (2H, s), 3.55 (3H, s), 2.42 (1H, d, J=13.5 Hz), 1.76 (1H, d, J=13.5 Hz), 1.04 (3H, s), 0.80 (3H, s). 3,3-Dimethyl-5-(2-pyridyl)-7-trifluoromethoxy-2,3,4,5-tetrahydro-1-benzoxepin-5-ol C$_{18}$H$_{18}$F$_3$NO$_3$ MM=353.340

Formula 10

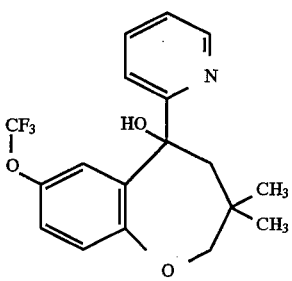

[chromatography with silica gel and dichloromethane; M.p.=76° C.; heptane; 62%]IR in cm⁻¹: 3290, 2950, 1590, 1485 ¹H NMR (CDCl₃) in ppm: 8.52 (1H, m), 7.13 (6H, m), 5.78 (1H, s), 4.16 (1H, d, J=11 Hz), 3.84 (1H, d, J=11 Hz), 2.39 (1H, d, J=13.5 Hz), 1.73 (1H, d, J=13.5 Hz), 1.10 (3H, s), 0.90 (3H, S). 3,3-Dimethyl-7-methylthio-5-(2-pyridyl)-2,3,4,5-tetra -hydro-1-benzoxepin-5-ol C$_{18}$H$_{21}$NO$_2$S MM=315.435

Formula 11

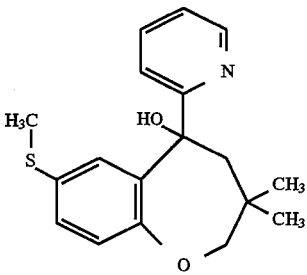

[B.p.$_{0.2\ mm\ Hg}$=180° C.; 69%]IR in cm¹: 3340, 2970, 1595, 1575 ¹H NMR (CDCl₃) in ppm: 8.53 (1H, m), 7.23 (6H, m), 5.70 (1H, s), 4.10 (1H, d, J=11 Hz), 3.81 (1H, d, J=11 Hz), 2.36 (1H, d, J=14 Hz), 2.25 (3H, s), 1.71 (1H, d, J=14 HZ), 1.09 (3H, s), 0.89 (3H, s). 3,3-Dimethyl-7-phenyl-5-(2-pyridyl)-2,3,4,5-tetrahydro -1-benzoxepin-5-ol C$_{23}$H$_{23}$NO$_2$ MM=345.440

Formula 12

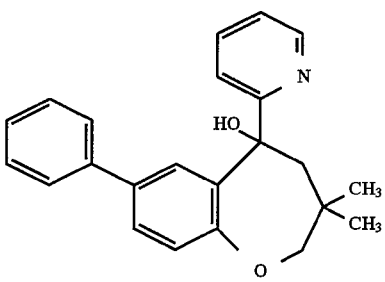

[chromatography with silica gel and dichloromethane; M.p.=140°–150° C.; heptane; 95%]IR in cm⁻¹: 3290, 2930, 1600 ¹H NMR (CDCl₃) in ppm: 8.50 (1H, m), 7.22 (11H, m), 5.82 (1H, m), 4.20 (1H, d, J=11 Hz), 3.89 (1H, d, J=11 Hz), 2.41 (1H, d, J=14 Hz), 1.75 (1H, d, J=14 Hz), 1.13 (3H, s), 0.95 (3H, s). 8-Bromo-3,3 -dimethyl-5-(2-pyridyl)-2,3, 4,5-tetrahydro- -1-benzoxepin-5-ol C$_{17}$H$_{18}$BrNO$_2$ MM=348.239

Formula 13

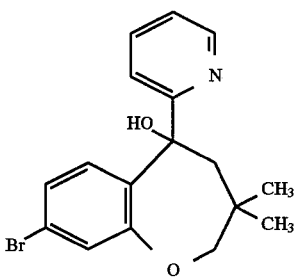

[chromatography with silica gel and dichloromethane; M.p.=110° C.; crystallization from hexane; 85%]IR in cm⁻¹: 3300, 2950, 1595, 1565, 1480 ¹H NMR (CDCl₃) in ppm: 8.55 (1H, m) , 7.55 (1H, dd, J=1.5 Hz, J=7.5 Hz), 7.07 (4H, m), 6.57 (1H, d, J=8 Hz), 5.87 (1H, m), 4.20 (1H, d, J=11 Hz), 3.90 (1H, d, 11 Hz), 2.37 (1H, d, J =13.5 Hz), 1.71 (1H, d, J=13.5 Hz), 1.12 (3H, s), 0.92 (3H, s) . 6,8-Dichloro-3, 3-dimethyl-5-(2-pyridyl) -2,3,4,5-tetra-hydro-1-benzoxepin-5-ol C$_{17}$H$_{17}$Cl$_2$NO$_3$ MM=33.233

Formula 14

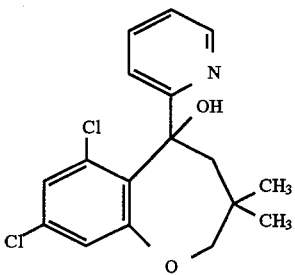

[M.p.=156° C.; heptane; 76%]IR in cm⁻¹: 3350, 3060, 2950, 1585, 1550 ¹H NMR (CDCl₃) in ppm: 8.49 (1H, m) , 7.12 (5H, m) , 5.81 (1H, s), 4.16 (1H, d, J=10.5 Hz), 3.92 (1H, d, J=10.5 Hz), 2.12 (1H, d, J=14 Hz), 1.52 (1H, d, J=14 Hz), 1.19 (3H, s), 0.98 (3H, s). 7,8-Dichloro-3,3-dimethyl-5-(2-pyridyl)-2,3,4,5-tetra-hydro -1-benzoxepin-5-ol C$_{17}$H$_{17}$Cl$_2$NO$_2$ MM=338.233

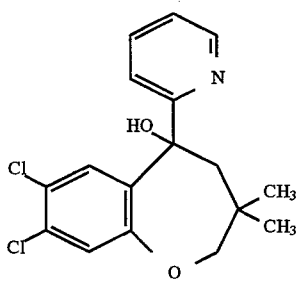

Formula 15

[M.p.=128° C.; hexane; 73%]IR in cm$^{-1}$: 3350, 2970, 1595, 1585, 1550 $^1$NMR (CDCl$_3$) in ppm: 8.51 (1H, m) , 7.35 (3H, m) , 7.08 (1H, s) , 6.83 (1H, s) , 5.77 (1H, s) , 4.12 (1H, d, J=11 Hz), 3.83 (1H, d, J=11 Hz), 2.34 (1H, d, J=13.5 Hz), 1.70 (1H, d, J=13.5 Hz), 1.06 (3H, s), 0.88 (3H, s) . 7,9-Dichloro-3,3 -dimethyl-5- (2-pyridyl) -2,3,4,5-tetrahydro-1-benzoxepin- -5-ol C$_{17}$H$_{17}$Cl$_2$NO$_2$ MM=338.233

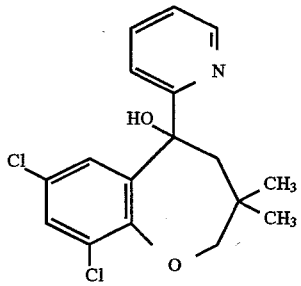

Formula 16

[chromatography with silica gel and dichloromethane; 83% IR in cm$^{-1}$: 3300, 2950, 1590, 1570, 1560 $^1$H NMR (CDCl$_3$) in ppm: 8.52 (1H, m), 7.25 (5H, m), 5.70 (1H, s), 4.00 (2H, s), 2.39 (1H, d, J =14 Hz), 1.76 (1H, d, J=14 Hz), 1.05 (3H, s), 0.86 (3H, s). 8,9-Dichloro-3,3-dimethyl-5-(2-pyridyl)-2, 3,4,5-tetra-hydro -1-benzoxepin-5-ol C$_{17}$H$_{17}$Cl$_2$NO$_2$ MM=338.233

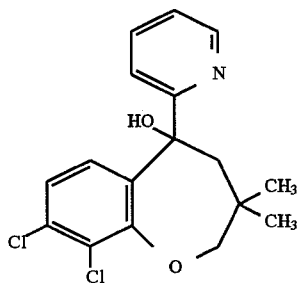

Formula 17

[yellow oil; 37%]IR in cm$^{-1}$: 3300, 2960, 1595, 1585, 1560 $^1$H NMR (CDCl$_3$) in ppm: 8.52 (1H, m) , 7.15 (5H, m) , 5.76 (1H, s), 4.07 (2H, s), 2.37 (1H, d, J =13.5 Hz) , 1.72 (1H, d, J=13.5 Hz), 1.10 (3H, s), 0.90 (3H, s). 7,8-Difluoro-3,3-dimethyl-5-(2-pyridyl) -2,3,4,5-tetra-hydro -1-benzoxepin-5-ol C$_{17}$H$_{17}$F$_2$NO$_2$ MM=305.324

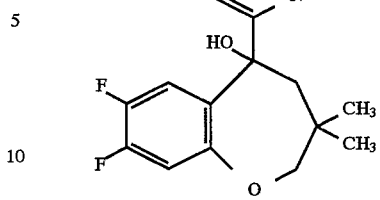

Formula 18

[M.p.=93° C.; crystallizes from pentane; 61%]IR in cm$^{-1}$: 3320, 2990, 1600, 1575, 1505 $^1$H NMR (CDCl$_3$) in ppm: 8.52 (1H, m), 7.61 (1H, m), 6.84 (4H, m), 5.71 (1H, s), 4.08 (1H, d, J=11 Hz), 3.83 (1H, d, J=11 Mz), 2.35 (1H, d, J=13.5 Hz), 1.70 (1H, d, J=13.5 Hz), 1.06 (3H, s), 0.87 (3H, s). 8-Chloro-7-fluoro-3,3-dimethyl-5-(2-pyridyl) -2,3,4,5-tetrahydro-1-benzoxepin-5-ol C$_{17}$H$_{17}$ClFNO$_2$ MM=321.778

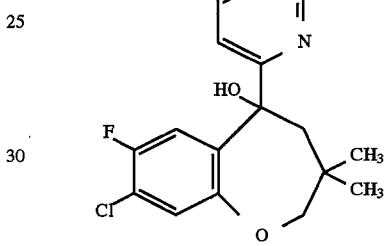

Formula 19

[M.p.=100° C.; hexane; 77%]IR in cm$^{-1}$: 3310, 2965, 1595, 1585, 1485 $^1$H NMR (CDCl$_3$) in ppm: 8.55 (1H, m) , 7.61 (1H, m) , 7.10 (3H, m), 6.63 (1H, d), 5.70 (1H, s), 4.08 (1H, d, J=6 Hz), 3.83 (1H, d, J=6 Hz), 2.40 (1H, d, J=13.5 Hz), 1.75 (1H, d, J=13.5 Hz), 1.08 (3H, s), 0.86 (3H, s). 9-Ethyl-7-fluoro-3,3-dimethyl-5-(2-pyridyl)-2,3,4,5-tetrahydro -1-benzoxepin-5-ol C$_{19}$H$_{22}$FNO$_2$ MM=315.387

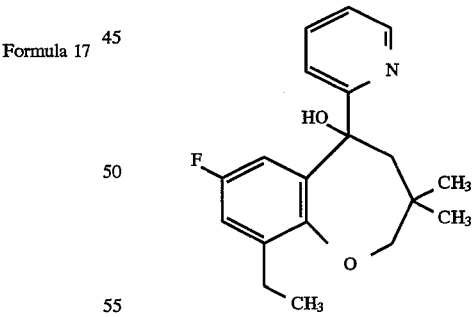

Formula 20

[M.p.=100° C.; crystallizes from pentane; 68%]IR in cm$^{-1}$: 3260, 2965, 1590 $^1$H NMR (CDCl$_3$) in ppm: 8.53 (1H, m), 7.04 (5H, m), 5.45 (1H, s), 3.85 (2H, s), 2.70 (2H, q), 2.40 (1H, d, J=13.5 Hz), 1.75 (1H, d, J=13.5 Hz), 1.19 (3H, t), 1.02 (3H, s), 0.78 (3H, s). 7,8-Dimethoxy-3,3-dimethyl-5-(2-pyridyl)-2,3,4,5-tetra-hydro-1-benzoxepin-5-ol C$_{19}$H$_{23}$NO$_4$ MM=329.395

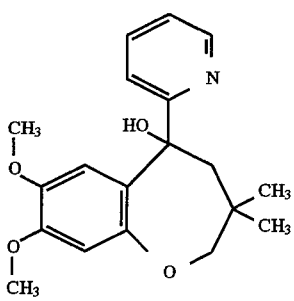

Formula 21

[chromatography with silica gel and dichloromethane/methanol: 98/2; M.p.=90° C.; crystallization from heptane; 63%]

IR in cm$^{-1}$: 3370, 2950, 1610, 1590, 1505 $^1$H NMR (CDCl$_3$) in ppm: 8.52 (1H, m), 7.56 (1H, m), 7.06 (3H, m), 6.54 (1H, s), 6.31 (1H, s), 5.50 (1H, m), 4.08 (1H, d, J=10 Hz), 3.81 (3H, s), 3.80 (1H, d, J=10 Hz), 3.55 (3H, s), 2.38 (1H, d, J=13 Hz), 1.73 (1H, d, J=13 Hz), 1.08 (3H, s), 0.85 (3H, s). 7-Bromo -3,3,8- trimethyl-5-(2-pyridyl)-2,3,4,5-tetrahydro-1-benzoxepin-5-ol C$_{18}$H$_{20}$BrNO$_3$ MM=362.266

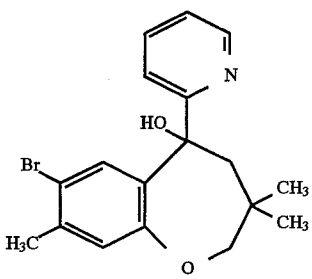

Formula 22

[chromatography with silica gel and dichloromethane; M.p.=147° C.; crystallizes from hexane; 63%]IR in cm$^{-1}$: 3360, 2970, 1595, 1570, 1540 $^1$H NMR (CDCl$_3$) in ppm: 8.54 (1H, m), 7.60 (1H, m), 7.05 (4H, m), 5.70 (1H, m), 4.10 (1H, d, J=11 Hz), 3.81 (1H, d, 11 Hz), 2.35 (1H, d, J=13.5 Hz), 2.27 (3H, s), 1.69 (1H, d, J=13.5 Hz), 1.07 (3H, s), 0.88 (3H, s). 8-Bromo-3,3,7-trimethyl-5-(2-pyrldyl)-2,3,4,5-tetrahydro-1-benzoxepin-5-ol C$_{18}$H$_{20}$BrNO$_2$ MM=362.266

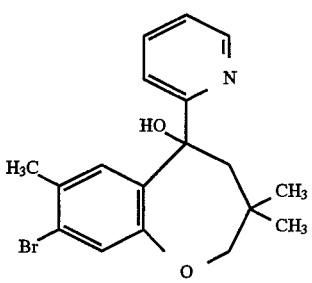

Formula 23

[chromatography with silica gel and dichloromethane; m.p.=129° C.; crystallizes from hexane; 70%]IR in cm$^{-1}$: 3320, 2950, 1595, 1560 $^1$H NMR (CDCl$_3$) in ppm: 8.52 (1H, m), 7.55 (1H, m), 7.14 (1H, s) , 7.04 (2H, m) , 6.62 (1H, s) , 5.64 (1H, s) , 4.05 (1H, d, J=11 Hz), 3.80 (1H, d, J=11 Hz), 2.32 (1H, d, J=13.5 Hz), 2.11 (3H, s), 1.67 (1H, d, J=13.5 Hz), 1.05 (3H, s) , 0.66 (3H, s). 3,3-Dimethyl-5-(2-pyridyl)-2,3,4,5,7,8,9,10-octahydro-1-naphth [2,3-b]oxepin-5-ol C$_{21}$H$_{25}$NO$_2$ MM=323.434

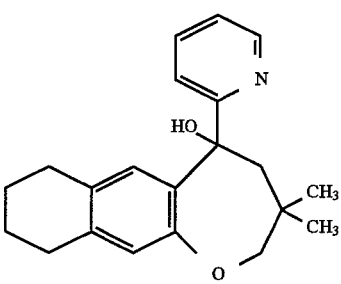

Formula 24

[chromatography with silica gel and dichloromethane; M.p.=134° C.; 67%]IR in cm$^{-1}$: 3330, 3060, 2930, 1620, 1595, 1570, 1500 $^1$H NMR (CDCl$_3$) in ppm: 8.50 (1H, m), 7.54 (1H, m), 7.08 (2H, m), 6.66 (1H, s), 6.50 (1H, s), 5.50 (1H, s), 4.02 (1H, d, J=10.5 Hz), 3.77 (1H, d, J=10.5 Hz), 2.56 (4H, m), 2.36 (1H, d, J=13.5 Hz), 1.74 (5H, m), 1.05 (3H, s), 0.83 (3H, s). 3,3-Dimethyl-5-(2-pyridyl)-7-trifluoromethyl-2,3,4,5-tetrahydro-1-benzoxepin-5-ol C$_{18}$H$_{18}$F$_3$NO$_2$ MM=337.341

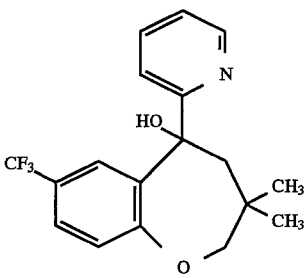

Formula 25

[chromatography with silica gel and dichloromethane; M.p.=116° C.; crystallization from leooctane; 29%]IR in cm$^{-1}$: 3330, 2970, 1625, 1600, 1580, 1505 $^1$H NMR (CDCl$_3$) in ppm: 8.50 (1H, dd, J=4.5 Hz), 7.25 (6H, m), 5.90 (1H, s), 4.22 (1H, d, J=11 Hz), 3.90 (1H, d, J=11 Hz), 2.35 (1H, d, J=13.5 Hz), 1.72 (1H, d, J=13.5 Hz), 1.10 (3H, s), 0.92 (3H, s). 3,3-Dimethyl-5-(2-pyridyl)-8-trifluoromethyl-2,3,4,5-tetrahydro-1-benzoxepin-5-ol C$_{18}$H$_{18}$F$_3$NO$_2$ MM=337.341

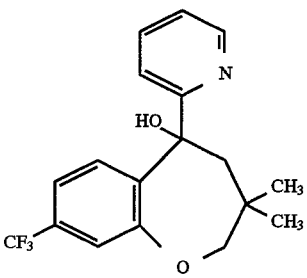

Formula 26

[chromatography with silica gel and dichloromethane; M.p.=78° C.; 31%]IR in cm$^{-1}$: 3330, 2970, 1595, 1575, 1500 $^1$H NMR (CDCl$_3$) in ppm: 8.55 (1H, dd, J=4.5 Hz), 7.25 (6H, m), 5.94 (1H, s), 4.22 (1H, d, J=11 Hz), 3.90 (1H, d, J=11 Hz), 2.40 (1H, d, J=14 Hz), 1.72 (1H, d, J=14 Hz), 1.12 (3H, s), 0.95 (3H, s). 3,3-Dimethyl-5-(2-pyridyl)-7-pentafluoroethyl-2,3,4,5-tetrahydro-1-benzoxepin-5-ol C$_{19}$H$_{18}$ F$_5$NO$_2$ MM=387.349

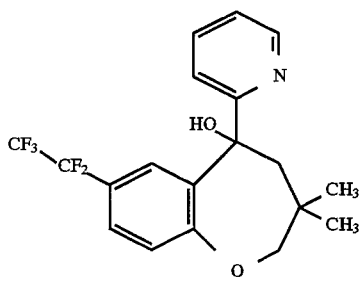

Formula 27

[chromatography with silica gel and dichloromethane; 42%] IR in cm$^{-1}$: 3330, 2950, 1620, 1595, 1575, 1500 $^1$H NMR (CDCl$_3$) in ppm: 8.55 (1H, dd, J=4.5 Hz), 7.28 (6H, m), 6.00 (1H, s), 4.33 (1H, d, J=11 Hz), 3.94 (1H, d, J=11 Hz), 2.38 (1H, d, J=14 Hz), 1.75 (1H, d, J=14 Hz), 1.15 (3H, s), 0.97 (3H, s). 8-Bromo-3,3-dimethyl-1-(2-pyridyl)-2,3,4,5-tetrahydro-1H-benzo [f]-cyclohepten-1-ol C$_{18}$H$_{20}$BrNO MM=346.266

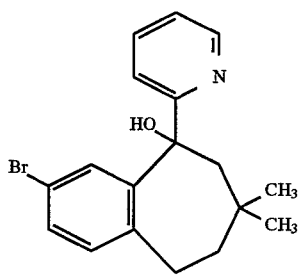

Formula 28

[chromatography with silica gel and dichloromethane; oil; 78%]IR in cm$^{-1}$: 3340, 2960, 1590, 1570 $^1$H NMR (CDCl$_3$) in ppm: 8.50 (1H, m), 7.54 (1H, m), 7.04 (5H, m), 5.39 (1H, s), 2.90 (2H, m), 2.32 (1H, d, J=14 Hz), 1.77 (1H, d, J=14 Hz), 1.70 (2H, m), 1.02 (6H, m). 7-Bromo-3,3-dimethyl-5-(3-pyridyl)-2,3,4,5-tetrahydro-1-benzoxepin-5-ol C$_{17}$H$_{18}$BrNO$_2$ MM=348.234

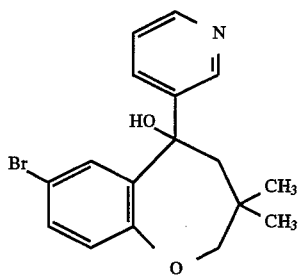

Formula 29

By using the same process as above and the use of 3-bromopyridine replacing 2-bromopyridine. [M.p.=170° C.; ethyl acetate; 46%]IR in cm$^{-1}$: 3120, 2950, 1585, 1475 $^1$H NMR (CDCl$_3$) in ppm: 8.37 (2H, m), 7.14 (4H, m), 6.88 (1H, d, J=9 Hz), 3.76 (2H, s), 3.74 (1H, m), 2.35 (1H, d, J=13.5 Hz), 2.00 (1H, d, J=13.5 Hz), 1.01 (3H, s), 0.62 (3H, s). 7,8-Dichloro-3,3-dimethyl-5-(3-pyridyl)-2,3,4,5-tetrahydro-1-benzoxepin-5-ol C$_{17}$H$_{17}$Cl$_2$NO$_2$ MM=338.233

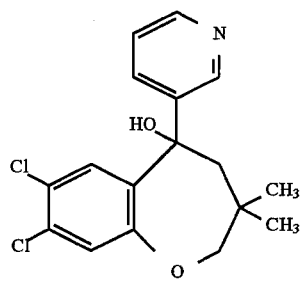

Formula 30

[M.p.=166° C.; crystallization from heptane; 44%]IR in cm$^{-1}$: 3100, 2930, 1595, 1585 $^1$H NMR (CDCl$_3$) in ppm: 8.41 (2H, m), 7.34 (4H, m), 3.76 (3H, s), 2.35 (1H, d, J=13.5 Hz); 2.00 (1H, d, J=13.5 Hz), 1.00 (3H, s), 0.61 (3H, s).

EXAMPLE 2

7-Bromo-5-methoxy-3,3,-dimethyl-5-(2-pyridyl)-1-benzoxepine C$_{18}$H$_{20}$BrNO$_2$ MM=362.265

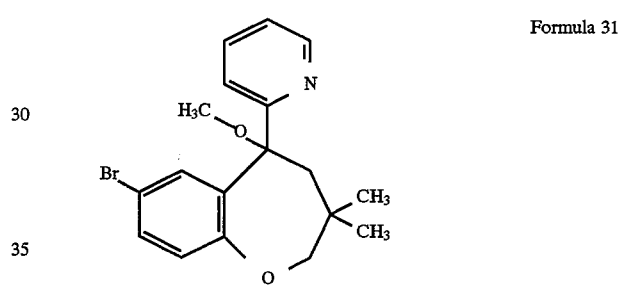

Formula 31

A solution of 7-bromo-3,3-dimethyl-5-(2-pyridyl)-1-benzoxepin-5-ol (5 g, 0.014 mol) in anhydrous DMF (50 ml) is added dropwise to a suspension of sodium hydride (50% dispersed in oil, 0.8 g, 0.0168 mol) in anhydrous DMF (25 ml), the temperature rises to 88° C., stirring is continued for 1 hour and the reaction mixture is maintained at 80° C. A solution of methyl iodide (1.9 g, 0.014 mol) in anhydrous DMF (10 ml) is then added dropwise at 25° C.

The whole mixture is stirred for 16 hours at 25° C. and then hydrolysed with 600 ml of ice-cold water. The paste obtained is dissolved in dichloromethane (250 ml). The organic phase is washed with water, dried over anhydrous sodium sulfate and concentrated under reduced pressure.

[pasty product; 5 g; 98%]IR in cm$^{-1}$: 2960, 1590, 1565 $^1$H NMR (CDCl$_3$) in ppm: 8.55 (1H, dd, J=4.5 Hz), 7.33 (6H, m), 3.91 (1H, s), 3.88 (1H, s), 3.16 (3H, s), 2.26 (2H, s), 1.11 (3H, s), 0.43 (3H, s).

EXAMPLE NO. 3

7-Bromo-3,3-dimethyl-5-(2-pyridyl)-2,3,4,5-tetrhydro-1-benzoxepin-5-yl acetate C$_{19}$H$_{20}$BrNO$_3$ MM=390.276

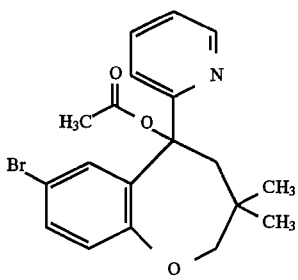

A solution of 7-bromo-3,3-dimethyl-5-(2-pyridyl)-1-benzoxepin-5-ol (5 g, 0.014 mol) in anhydrous DMF (50 ml) is added dropwise at 60° C. to a suspension of sodium hydride (50% dispersed in oil, 0.8 g, 0.0168 mol) in anhydrous DMF (25 ml).

The suspension is stirred for 1 hour at 60° C. and then cooled. Acetyl chloride (1 g, 0.014 mol) is added dropwise at 25° C. and the stirring is continued at 25° C. for 16 hours. The whole mixture is then hydrolysed in 600 ml of ice-cold water. The beige paste obtained is dissolved in 200 ml of dichloromethane. The organic phase is washed with water, dried over anhydrous sodium sulfate and concentratedunder reduced pressure. The oil obtained is purified by chromatography with silica gel and dichloromethane/methanol: 98/2.

[M.p.=140° C.; hexane; 22%]IR in cm$^{-1}$: 2950, 1745, 1590, 1570, 1485 $^1$H NMR (CDCl$_3$) in ppm: 8.50 (1H, dd, J=4.5 Hz), 7.25 (6H, m), 3.78 (2H, s), 2.95 (1H, d, J=13.5 Hz), 2.38 (1H, d, J=13.5 Hz), 2.07 (3H, 8) , 1.05 (3H, 8) , 0.37 (3H, s).

EXAMPLE NO. 4

7-Bromo-3,3-dimethyl-5-(2-pyridyl N-oxide)-2,3,4,5-tetrahydro-1-benzoxepin-5-ol C$_{17}$H$_{18}$BrNO$_3$ MM=364.238

Formula 33

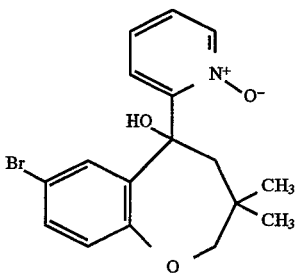

A solution of 7-bromo-3,3-dimethyl-5-(2-pyridyl)-2,3,4,5-tetrahydro-1-benzoxepin-5-ol (3.5 g, 0.01 mol) and of 3-chloroperbenzoic acid (2.8 g, 0.016 mol) in dichloromethane (50 ml) is stirred for 16 hours at 25° C.

The precipitate formed is filtered. The filtrate is washed with a 5% sodium bisulfite solution, then with a 5% sodium bicarbonate solution and with water. The organic phase is dried over anhydrous sodium sulfate and concentrated under reduced pressure (thick yellow oil). The product is recrystallized from hexane (2.6 g).

[M.p.=139°–140° C.; hexane]IR in cm$^{-1}$: 3240, 3050, 2950, 1480 $^1$H NMR (CDCl$_3$) in ppm: 8.18 (1H, m), 7.88 (1H, d), 7.13 (5H, m), 6.03 (1H, m), 3.81 (1H, m), 3.49 (1H, m), 3.31 (1H, m), 1.94 (1H, d, J=13.5 Hz), 0.86 (3H, s) , 0.51 (3H, s).

Formula 32

| | Elemental analysis | | | | |
|---|---|---|---|---|---|
| | C | H | Br | N | O |
| % Found | 56.07 | 5.02 | | 3.73 | 13.42 |
| % Calculated | 56.05 | 4.98 | 21.94 | 3.85 | 13.18 |

By using the same process, the following compounds are prepared.

7-Chloro-3,3-dimethyl-5-(2-pyridyl N-oxide)-2,3,4,5-tetrahydro-1-benzoxepin-5-ol C$_{17}$H$_{18}$ClNO$_3$ MM=319.787

Formula 34

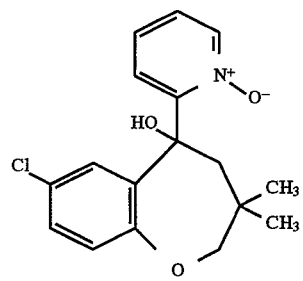

[M.p.=138°–140° C.; ethyl acetate; 34%]IR in cm$^{-1}$: 3250, 3070, 2950, 1480 $^1$H NMR (CDCl$_3$) in ppm: 8.23 (1H, m), 7.77 (1H, d), 7.11 (5H, m), 6.05 (1H, m), 3.82 (1H, m), 3.50 (1H, m), 3.32 (1H, m), 1.93 (1H, d, J=14 Hz), 0.85 (3H, s), 0.56 (3H, s).

| | Elemental analysis | | | | |
|---|---|---|---|---|---|
| | C | H | Cl | N | O |
| % Found | 63.58 | 5.71 | 11.04 | 4.47 | |
| % Calculated | 63.85 | 5.67 | 11.09 | 4.38 | 15.01 |

7-Fluoro-3,3-dimethyl-5-(2-pyridyl N-oxide)-2,3,4,5-tetrahydro-1-benzoxepin-5-ol C$_{17}$H$_{18}$FNO$_3$ MM=303.332

Formula 35

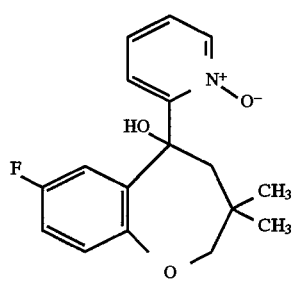

[M.p.=110°–112° C.; hexane 78%]IR in cm$^{-1}$: 3390, 3110, 2950, 1485 $^1$H NMR (CDCl$_3$) in ppm: 8.19 (1H, m), 7.30 (7H, m), 3.80 (1H, m) , 3.48 (1H, m) , 3.34 (1H, m) , 1.93 (1H, d, J=14 Hz), 0.85 (6H, s).

| | Elemental analysis | | | | |
|---|---|---|---|---|---|
| | C | H | F | N | O |
| % Found | 67.14 | 6.04 | 6.16 | 4.53 | |
| % Calculated | 67.31 | 5.98 | 6.26 | 4.62 | 15.82 |

3,3-Dimethyl-5-(2-pyridyl N-oxide)-2,3,4,5-tetrahydro-1-benzoxepin-5-ol $C_{17}H_{19}NO_3$ MM=285.342

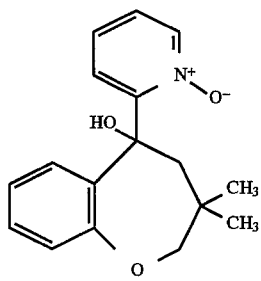

Formula 36

[chromatography with silica gel and ethyl acetate/chloroform/methanol; 60/30/10; M.p.=127°–128° C.; cyclohexane; 41%] IR in cm$^{-1}$: 3180, 3070, 2950, 1605, 1575, 1480 $^1$H NMR (CDCl$_3$) in ppm: 8.20 (1H, m), 7.75 (1H, m), 7.05 (6H, m), 3.81 (1H, m), 3.52 (1H, m), 3.32 (1H, m), 1.97 (1H, d, J=14 Hz), 0.88 (3H, s), 0.60 (3H, s).

| | Elemental analysis | | | |
|---|---|---|---|---|
| | C | H | N | O |
| % Found | 71.58 | 6.88 | 4.85 | |
| % Calculated | 71.56 | 6.71 | 4.91 | 16.82 |

7-Ethyl-3,3-dimethyl-5-(2-pyridyl N-oxide)-2,3,4,5-tetrahydro-1-benzoxepin-5-ol $C_{19}H_{23}NO_3$ MM=313.396

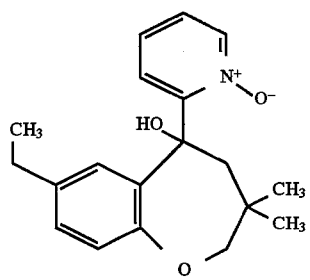

Formula 37

[chromatography with silica gel and dichloromethane/methanol; 98/2; M.p.=123°–125° C.; diisopropyl ether; 23%] IR in cm$^{-1}$: 3230, 3050, 2950, 1615, 1580, 1500 $^1$H NMR (CDCl$_3$) in ppm: 8.20 (1H, m), 7.60 (1H, m), 7.11 (5H, m), 6.50 (1H, m), 3.80 (1H, m), 3.50 (1H, m), 3.30 (1H, m), 2.64 (2H, q), 1.93 (1H, d, J=13.5 Hz), 1.21 (3H, t), 0.83 (3H, s), 0.54 (3H, s).

| | Elemental analysis | | | |
|---|---|---|---|---|
| | C | H | N | O |
| % Found | 73.03 | 7.49 | 4.57 | |
| % Calculated | 72.82 | 7.40 | 4.47 | 15.32 |

3,3-Dimethyl-7-(1-methylpropyl)-5-(2-pyridyl N-oxide)-2,3,4,5-tetrahydro-1-benzoxepin-5-ol $C_{21}H_{27}NO_3$ MM=341.449

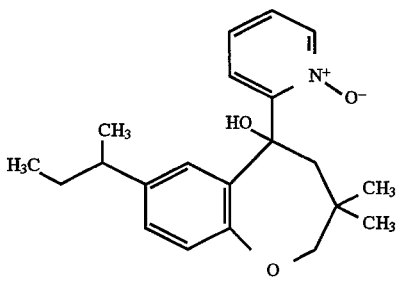

Formula 38

[chromatography with silica gel and dichloromethane; M.p.=131°–133° C.; diisopropyl ether; 39%] IR in cm$^{-1}$: 3150, 2960, 1610, 1495 $^1$H NMR (CDCl$_3$) in ppm: 8.20 (1H, m), 7.20 (7H, m), 3.77 (1H, d, J=11 Hz), 3.48 (1H, d, J=11 Hz), 3.28 (1H, d, J=14 Hz), 2.58 (1H, q), 1.92 (1H, d, J=14 Hz), 1.10 (14H, m).

| | Elemental analysis | | | |
|---|---|---|---|---|
| | C | H | N | O |
| % Found | 73.66 | 7.97 | 4.39 | |
| % Calculated | 73.87 | 7.97 | 4.10 | 14.06 |

7-Methoxy-3,3-dimethyl-5-(2-pyridyl-N-oxide)-2,3,4,5-tetrahydro-1-benzoxepin-5-ol $C_{18}H_{21}NO_4$ MM=315.368

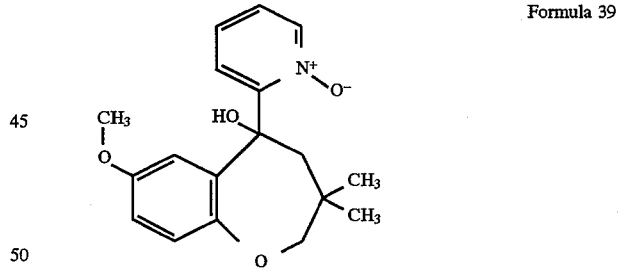

Formula 39

[chromatography with silica gel and dichloromethane/methanol; 98/2; M.p.=109°–110° C.; isooctane] IR in cm$^{-1}$: 3200, 3080, 2950, 1605, 1495 $^1$H NMR (CDCl$_3$) in ppm: 8.19 (1H, m), 7.15 (7H, m), 3.74 (3H, s), 3.58 (3H, m), 1.90 (1H, d, a=13.5 Hz), 0.82 (3H, s), 0.55 (3H, s).

| | Elemental analysis | | | |
|---|---|---|---|---|
| | C | H | N | O |
| % Found | 68.52 | 6.55 | 4.48 | |
| % Calculated | 68.55 | 6.71 | 4.44 | 20.29 |

3,3-Dimethyl-5-(2-pyridyl N-oxide)-7-trifluoromethoxy-2,3,4,5-tetrahydro-1-benzoxepin-5-ol  C$_{18}$H$_{18}$F$_3$NO$_4$  MM=370.348

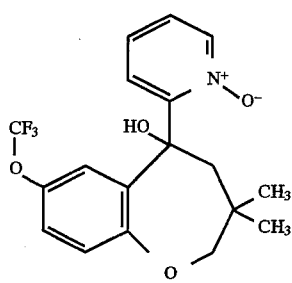

Formula 40

[chromatography with silica gel and dichloromethane; M.p.=114°–116° C.; heptane; 50%]IR in cm$^{-1}$: 3400, 3130, 3060, 2970, 1490 $^1$H NMR (CDCl$_3$) in ppm: 8.21 (1H, m), 7.64 (1H, m), 7.01 (6H, m), 3.80 (1H, d, J=11 Hz), 3.49 (1H, d, J=11 Hz), 3.30 (1H, d, J=14 Hz), 1.91 (1H, d, J=14 Hz), 0.84 (3H, s), 0.52 (3H, s).

| | Elemental analysis | | | | |
|---|---|---|---|---|---|
| | C | H | F | N | O |
| % Found | 58.33 | 4.95 | 15.31 | 3.86 | |
| % Calculated | 58.53 | 4.91 | 15.43 | 3.79 | 17.33 |

3,3-Dimethyl-7-phenyl-5-(2-pyridyl N-oxide)-2,3,4,5-tetrahydro-1-benzoxepin-5-ol  C$_{23}$H$_{23}$NO$_3$  MM=361.440

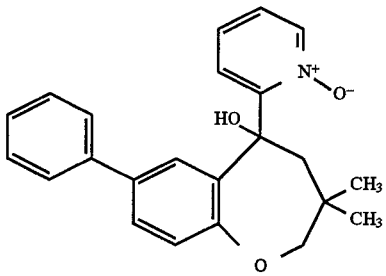

Formula 41

[chromatography with silica gel and methanol; M.p.=175° C.; diisopropyl ether/ethyl acetate; 50/50; 25%]IR in cm$^{-1}$: 3200, 2960, 1610 $^1$H NMR (CDCl$_3$) in ppm: 8.14 (2H, m), 7.27 (10H, m), 3.85 (1H, d, J=11 Hz), 3.55 (1H, d, J=11 Hz), 3.34 (1H, d, J=14 Hz), 2.02 (1H, d, J=14 Hz), 0.90 (3H, s), 0.60 (3H, s).

| | Elemental analysis | | | |
|---|---|---|---|---|
| | C | H | N | O |
| % Found | 76.57 | 6.37 | 3.90 | |
| % Calculated | 76.43 | 6.41 | 3.88 | 13.28 |

7-Bromo-3,3-dimethyl-5-(2-pyridyl N-oxide)-2,3,4,5-tetrahydro-1-benzoxepin-5-ol  C$_{17}$H$_{18}$BrNO$_3$  MM=364.238

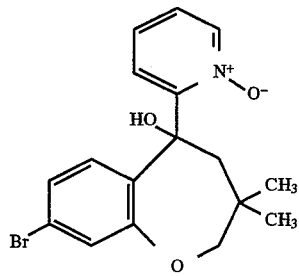

Formula 42

[M.p.=137°–138° C.; ethyl acetate; 20%]IR in cm$^{-1}$: 3090, 2950, 1590, 1560, 1475 $^1$H NMR (CDCl$_3$) in ppm: 8.20 (1H, m) , 7.65 (1H, m) , 7.62 (1H, d, J=8 Hz), 7.03 (5H, m), 3.81 (1H, d, J=11 Hz), 3.50 (1H, d, J=11 Hz), 3.29 (1H, d, J=14 Hz), 1.92 (1H, d, J=14 Hz), 0.88 (3H, s), 0.53 (3H, s).

6,8-Dichloro-3,3-dimethyl-5-(2-pyridyl N-oxide)-2,3,4,5-tetrahydro-1-benzoxepin-5-ol  C$_{17}$H$_{17}$Cl$_2$NO$_3$  MM=354.232

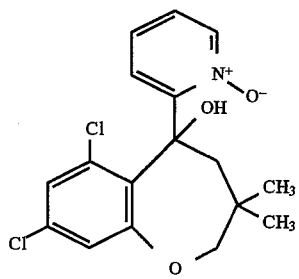

Formula 43

[M.p.=220° C.; ethyl acetate; 35%]IR in cm$^{-1}$: 3065, 2970, 1585, 1550 $^1$H NMR (CDCl$_3$) in ppm: 8.15 (1H, m), 6.92 (5H, m), 4.00 (2H, s), 2.18 (2H, s), 1.28 (3H, s), 1.00 (3H, s).

| | Elemental analysis | | | |
|---|---|---|---|---|
| | C | H | Cl | N | O |
| % Found | 57.54 | 4.84 | 20.23 | 4.04 | |
| % Calculated | 57.64 | 4.84 | 20.02 | 3.95 | 13.55 |

7,8-Dichloro-3,3-dimethyl-5-(2-pyridyl N-oxide)-2,3,4,5-tetrahydro-1-benzoxepin-5-ol  C$_{17}$H$_{17}$Cl$_2$NO$_3$  MM=354.232

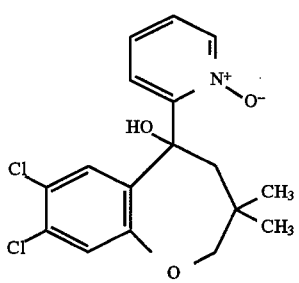

Formula 44

[M.p.=134°–136° C.; diisopropyl oxide; 18%]IR in cm$^{-1}$: 3250, 3050, 2970, 1480 $^1$H (CDCl$_3$) in ppm: 8.21 (1H, m), 7.85 (1H, s), 7.08 (5H, m), 3.80 (1H, d, J=11 Hz), 3.38 (2H, m), 1.90 (1H, d, J=14 Hz), 0.88 (3H, s), 0.55 (3H, s).

| Elemental analysis | | | | | |
|---|---|---|---|---|---|
| | C | H | Cl | N | O |
| % Found | 57.80 | 4.70 | 19.73 | 4.02 | |
| % Calculated | 57.64 | 4.84 | 20.02 | 3.95 | 13.55 |

7,9-Dichloro-3,3-dimethyl-5-(2-pyridyl N-oxide)-2,3,4,5-tetrahydro-1-benzoxepin-5-ol $C_{17}H_{17}Cl_2NO_3$ MM=354.232

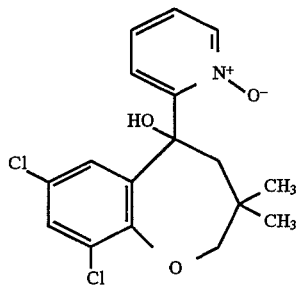

Formula 45

[M.p.=150.5° C.; diisopropyl ether; 33%]IR in cm$^{-1}$: 3230, 3070, 2970, 1570 $^{-1}$H NMR (CDCl$_3$) in ppm: 8.20 (1H, m), 7.70 (1H, m), 7.09 (4H, m), 3.89 (1H, dd, J=1.5 Hz, J=11 Hz), 3.40 (1H, d, J=11 Hz), 3.31 (1H, dd, J=1.5 Hz, J=13.5 Hz), 1.82 (1H, d, J=13.5 Hz), 0.81 (3H, s), 0.59 (3H, s).

| Elemental analysis | | | | | |
|---|---|---|---|---|---|
| | C | H | Cl | N | O |
| % Found | 57.38 | 4.89 | 20.02 | 3.99 | |
| % Calculated | 57.64 | 4.84 | 20.02 | 3.95 | 13.55 |

8-Chloro-7-fluoro-3,3-dimethyl-5-(2-pyridyl N-oxide)-2,3,4,5-tetrahydro-1-benzoxepin-5-ol $C_{17}H_{17}ClFNO_3$ MM=337.777

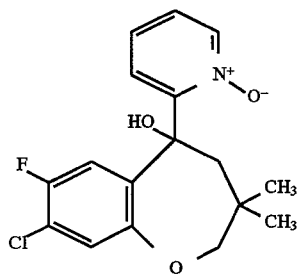

Formula 46

[M.p.=121°123° C.; diisopropyl oxide; 24%]IR in cm$^{-1}$: 3290, 3070, 1485 $^1$H (CDCl$_3$) in ppm: 8.23 (1H, m), 7.87 (1H, s), 7.60 (1H, d), 7.08 (4H, m), 3.58 (3H, m), 1.90 (1H, d, J=14 Hz), 0.84 (3H, s), 0.55 (3H, s).

| Elemental analysis | | | | | |
|---|---|---|---|---|---|
| | C | H | Cl | F | N | O |
| % Found | 60.44 | 5.30 | 10.56 | 5.69 | 4.16 | |
| % Calculated | 60.45 | 5.07 | 10.50 | 5.63 | 4.15 | 14.21 |

7,8-Dimethoxy-3,3-dimethyl-5-(2-pyridyl N-oxide)-2,3,4,5-tetrahydro-1-benzoxepin-5-ol $C_{19}H_{23}NO_5$ MM=345.394

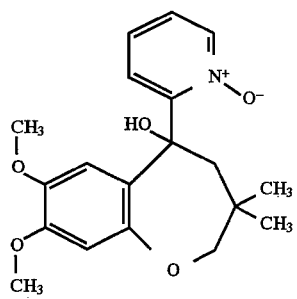

Formula 47

[chromatography with silica gel and dichloromethane/methanol; 98/2; M.p.=174° C.; ethyl acetate]

IR in cm$^{-1}$: 3220, 3090, 2970, 1615, 1510 $^1$H NMR (CDCl$_3$) in ppm: 8.22 (1H, m), 7.18 (4H, m), 6.62 (1H, s), 3.87 (3H, s), 3.80 (3H, s), 3.76 (1H, d, J=10 Hz), 3.50 (1H, d, J=10 Hz), 3.29 (1H, d, J=13 Hz), 1.92 (1H, d, J=13 Hz), 0.87 (3H, s), 0.55 (3H, s).

| Elemental analysis | | | | |
|---|---|---|---|---|
| | C | H | N | O |
| % Found | 66.35 | 6.87 | 4.20 | |
| % Calculated | 66.07 | 6.71 | 4.06 | 23.16 |

3,3-Dimethyl-5-(2-pyridyl N-oxide)-7-trifluoromethyl-2,3,4,5-tetrahydro-1-benzoxepin-5-ol $C_{18}H_{18}F_3NO_3$ MM=353.340

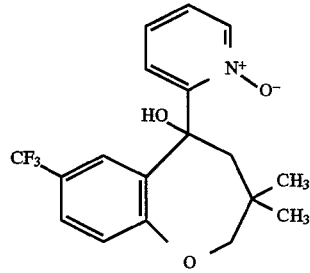

Formula 48

[M.p.=106°–107° C.; hexane; 76%]IR in cm$^-$: 3400, 3110, 2950, 1615, 1590, 1500, 1480 $^1$H NMR (CDCl$_3$) in ppm: 8.05 (2H, m), 7.13 (6H, m), 3.80 (1H, m), 3.50 (1H, m), 3.29 (1H, m), 1.95 (1H, d, J=13.5 Hz), 0.86 (3H, s), 0.54 (3H, s).

| Elemental analysis | | | | |
|---|---|---|---|---|
| | C | H | F | N | O |
| % Found | 61.40 | 5.08 | 16.01 | 4.01 | |
| % Calculated | 61.18 | 5.14 | 16.13 | 3.96 | 13.58 |

3,3-Dimethyl-5-(2-pyridyl N-oxide)-8-trifluoromethyl-2,3,4,5-tetrahydro-1-benzoxepin-5-ol C₁₈H₁₈F₃NO₃ MM=353.340

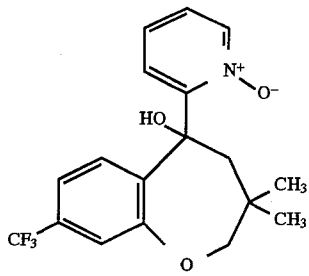

Formula 49

[chromatography with silica gel and dichloromethane/methanol; 98/2; M.p.=102°–105° C.; cyclohexane; 27%]IR in cm⁻¹: 3400, 3050, 2950, 1585, 1480 ¹H NMR (CDCl₃) in ppm: 8.20 (1H, m), 7.37 (7H, m), 3.86 (1H, m), 3.55 (1H, m), 3.32 (1H, m), 1.95 (1H, d, J=14 Hz), 0.88 (3H, s), 0.56 (3H, s). 7-Bromo-5-methoxy-3,3-dimethyl-5-(2-pyridyl N-oxide)-2,3,4,5-tetrahydro-1-benzoxepine C₁₈H₂₀BrNO₃ MM=378.265

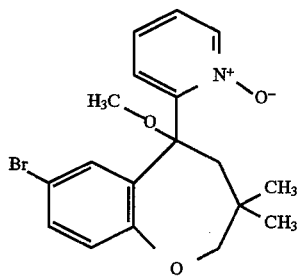

Formula 50

M.p.=178°–180° C.; ethyl acetate; 33%]IR in cm⁻¹: 2960, 1595, 1560, 1480 ⁻¹NMR (CDCl₃) in ppm: 8.06 (1H, m), 7.14 (6H, m), 3.98 (1H, d, J=11 Hz), 3.70 (1H, d, J=11 Hz), 3.33 (1H, d, J=14 Hz), 3.05 (3H, s), 1.61 (1H, d, J=14 Hz), 1.11 (3H, s), 0.95 (3H, s).

| | Elemental analysis | | | | |
|---|---|---|---|---|---|
| | C | H | Br | N | O |
| % Found | 56.96 | 5.50 | 21.10 | 3.58 | |
| % Calculated | 57.15 | 5.33 | 21.13 | 3.70 | 12.69 |

EXAMPLE NO. 5

7-Bromo-3,3-dimethyl-5-(2-pyridyl N-oxide)-2,3,4,5-tetrahydro-1-benzoxepin-5-yl acetate C₁₉H₂₀BrNO₄ MM=406.275

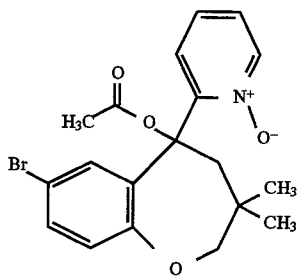

Formula 51

M.p.=145°–147° C.; isooctane/ethyl acetate: 80-20/ IR in cm⁻¹: 2950, 1730, 1605, 1480 ⁻¹H NMR (CDCl₃) in ppm:

8.05 (1H, m), 7.17 (6H, m), 3.58 (3H, m), 2.19 (3H, s), 2.07 (1H, d, J=14 Hz), 0.93 (3H, s), 0.60 (3H, s).

| | Elemental analysis | | | | |
|---|---|---|---|---|---|
| | C | H | Br | N | O |
| % Found | 56.20 | 5.05 | 19.75 | 3.40 | |
| % Calculated | 56.17 | 4.96 | 19.67 | 3.45 | 15.75 |

7-Bromo-4,5-epoxy-3,3-dimethyl-5-(2-pyridyl N-oxide)-2,3-dihydro-1-benzoxepine C₁₇H₁₆BrNO₃ MM=362.222

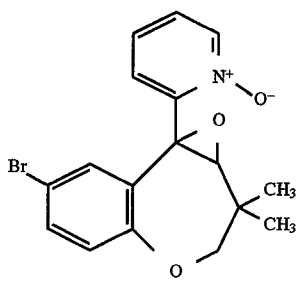

Formula 52

[chromatography with silica gel and ethyl acetate; M.p.= 186°–187° C.; ethanol; 20%]IR in cm⁻¹: 3060, 2970, 1560, 1480 ¹H NMR (CDCl₃) in ppm: 8.05 (1H, m), 7.22 (6H, m), 3.75 (2H, s), 2.98 (1H, s), 1.46 (3H, s), 1.17 (3H, s).

| | Elemental analysis | | | | |
|---|---|---|---|---|---|
| | C | H | Br | N | O |
| % Found | 56.14 | 4.51 | 22.27 | 3.76 | 13.07 |
| % Calculated | 56.37 | 4.45 | 22.06 | 3.87 | 13.26 |

7-Bromo-3,3-dimethyl-5-(3-pyridyl N-oxide)-2,3,4,5-tetrahydro-1-benzoxepin-5-ol C₁₇H₁₈BrNO₃ MM=364.233

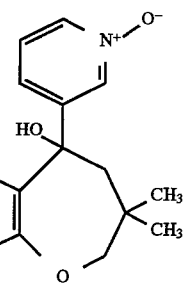

Formula 53

[M.p.=200° C.; ethanol; 38%]IR in cm⁻¹: 3180, 2950, 1595, 1560, 1485 ¹H NMR (DMSO) in ppm: 8.07 (2H, m), 7.14 (5H, m), 6.31 (1H, e), 3.78 (2H, s), 2.30 (1H, d, J=13.5 Hz), 1.88 (1H, d, J=13 Hz), 0.94 (3H, s), 0.69 (3H, s).

| | Elemental analysis | | | | |
|---|---|---|---|---|---|
| | C | H | Br | N | O |
| % Found | 56.03 | 5.03 | 21.71 | 3.85 | |
| % Calculated | 56.05 | 4.98 | 21.94 | 3.85 | 13.18 |

7,8-Dichloro-3,3-dimethyl-5-(3-pyridyl N-oxide)-2,3,4,5-tetrahydro-1-benzoxepin-5-ol  $C_{17}H_{17}Cl_2NO_3$  MM=354.232

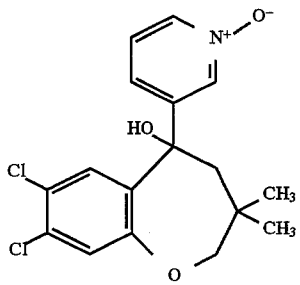

Formula 54

[M.p.=226°–228° C.; isopropanol; 23%]IR in cm$^{-1}$: 3160, 2950, 1590 $^1$H NMR (DMSO) in ppm: 8.05 (2H, m), 7.17 (4H, m), 6.32 (1H, s), 3.81 (2H, s), 2.30 (1H, d, J=14 Hz), 1.86 (1H, d, J=14 Hz), 0.96 (3H, s), 0.71 (3H, s).

| | Elemental analysis | | | | |
|---|---|---|---|---|---|
| | C | H | Cl | N | O |
| % Found | 57.75 | 5.12 | 19.84 | 4.06 | |
| % Calculated | 57.64 | 4.84 | 20.02 | 3.95 | 13.55 |

EXAMPLE NO. 6

7-Bromo-3,3-dimethyl-5-(2-pyridyl)-2,3-dihydro-1-benzoxepine $C_{17}H_{16}BrNo$ MM=330.224

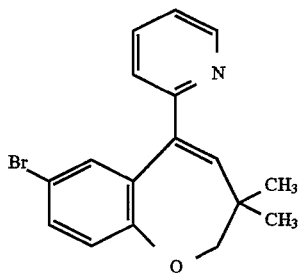

Formula 55

A solution of 7-bromo-3,3-dimethyl-5-(2-pyridyl)-2,3,4,5-tetrahydro-1-benzoxepin-5-ol (13.9 g, 0.04 mol) and of concentrated sulfuric acid (3.3 ml of commercial solution) in benzene (170 ml) is heated for 3 hours at boiling with removal of water.

The solution is washed, at 25° C., with a 1% sodium hydroxide solution and then with water. The organic phase is dried over anhydrous sodium sulfate and concentrated under reduced pressure.

[13.2 g; M.p.=113°–114° C.; hexane; 70%]IR in cm$^{-1}$: 2950, 1580, 1560, 1480 $^1$H NMR (CDCl$_3$) in ppm: 8.62 (1H, m), 7.30 (6H, m), 5.90 (1H, s), 3.93 (2H, s), 1.20 (6H, s).

| | Elemental analysis | | | | |
|---|---|---|---|---|---|
| | C | H | Br | N | O |
| % Found | 61.61 | 4.96 | 24.03 | 4.31 | |
| % Calculated | 61.83 | 4.88 | 24.20 | 4.24 | 4.85 |

By using the same process, the following compounds are prepared.

7-Chloro-3,3-dimethyl-5-(2-pyridyl)-2,3-dihydro-1-benzoxepine $C_{17}H_{16}ClNO$ MM=285.773

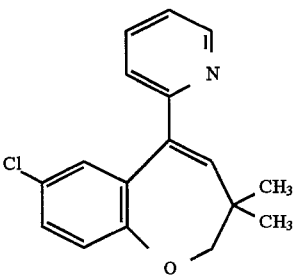

Formula 56

[M.p.=100° C.; hexane; 79%]IR in cm$^{-1}$: 2960, 1585, 1565, 1490 $^1$NMR (CDCl$_3$) in ppm: 8.62 (1H, m), 7.28 (6H, m), 5.92 (1H, s), 3.91 (2H, s), 1.15 (6H, s). 7-Fluoro-3,3-dimethyl-5-(2-pyridyl)-2,3-dihydro-1-benzoxepine $C_{17}H_{16}FNO$ MM=269.318

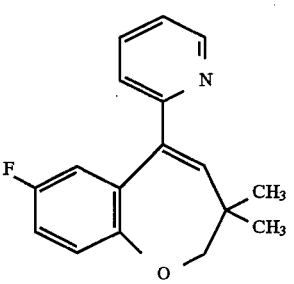

Formula 57

[thick yellow oil; 38 %]IR in cm$^{-1}$: 2970, 1590, 1565, 1495 $^1$H NMR (CDCl$_3$) in ppm: 8.55 (1H, m), 7.02 (6H, m), 5.89 (1H, s), 3.90 (2H, s), 1.16 (6H, s). 3,3-Dimethyl-5-(2-pyridyl)-2,3-dihydro-1-benzoxepine $C_{17}H_{17}NO$ MM=251.327

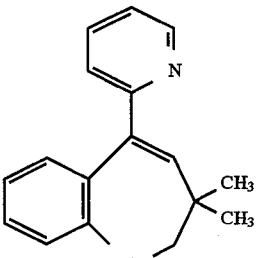

Formula 58

[oil; 98%]IR in cm$^{-1}$: 2960, 1590, 1565, 1495 $^1$H NMR (CDCl$_3$) in ppm: 8.56 (1H, m), 7.20 (7H, m), 5.83 (1H, s), 3.94 (2H, s), 1.18 (6H, s). 3,3,7-Trimethyl-5-(2-pyridyl)-2,3-dihydro-1-benzoxepine $C_{18}H_{19}NO$ MM=265.354

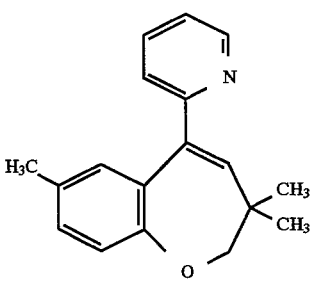

Formula 59

[oil; 98%]IR in cm$^{-1}$: 2960, 1590, 1565, 1500 $^1$H NMR (CDCl$_3$) in ppm: 8.58 (1H, m), 7.10 (6H, m), 5.83 (1H, s), 3.91 (2H, s), 2.10 (3H, s), 1.18 (6H, s). 7-Ethyl-3,3-dimethyl-5-(2-pyridyl)-2,3-dihydro-1-benzoxepine $C_{19}H_{21}NO$ MM=279.381

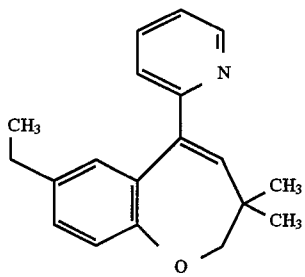

Formula 60

[yellow oil; 97%]IR in cm$^{-1}$: 2960, 1590, 1565, 1500 $^1$H NMR (CDCl$_3$) in ppm: 8.58 (1H, m) , 7.14 (6H, m) , 5.84 (1H, s), 3.91 (2H, s), 2.40 (2H, q), 1.16 (6H, s), 1.03 (3H, t). 7- Isopropyl-3,3-dimethyl-5-(2-pyridyl)-2,3-dihydro-1-benzoxepine C$_{20}$H$_{23}$NO MM=293.408

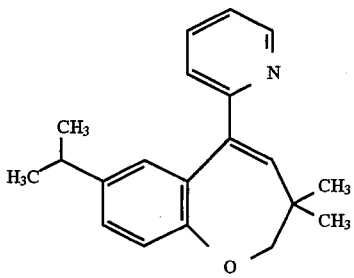

Formula 61

[yellow oil; 98%]IR in cm$^{-1}$: 2960, 1585, 1495 $^1$H NMR (CDCl$_3$) in ppm: 8.59 (1H, m) , 7.64 (1H, m) , 6.90 (5H, m), 5.84 (1H, s), 3.91 (2H, s), 2.68 (1B, m), 1.10 (12H, m). 3,3-Dimethyl-7-(1-methylpropyl)-5-(2-pyridyl)-2,3-dihydro-1-benzoxepine C$_{21}$H$_{23}$NO MM=307.435

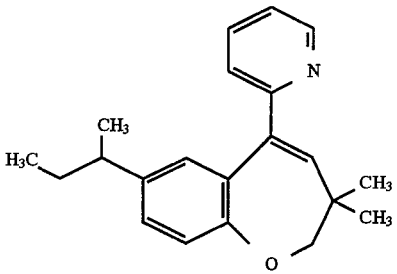

Formula 62

[yellow oil; 77%]IR in cm$^{-1}$: 2965, 1585, 1565, 1500 $^1$H NMR (CDCl$_3$) in ppm: 8.59 (1H, m) , 7.29 (5H, m) , 6.54 (1H, s) , 5.86 (1H, s), 3.92 (2H, s), 2.31 (1H, m), 1.09 (14H, m). 7-Methoxy-3,3-dimethyl-5-(2-pyridyl)-2,3-dihydro-1-benzoxepine C$_{18}$H$_{19}$NO$_2$ MM=281.353

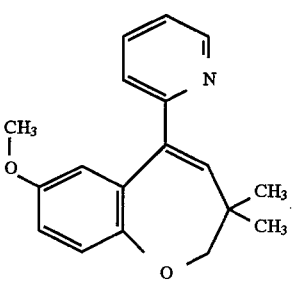

Formula 63

[M.p.=80° C.; 78%]IR in cm$^{-1}$: 2960, 1585, 1565, 1495 $^1$H NMR (CDCl$_3$) in ppm: 8.54 (1H, m), 7.00 (6H, m) , 5.85 (1H, s), 3.88 (2H, s), 3.50 (3H, s), 1.03 (6H, s). 3-Dimethyl-5-(2-pyridyl)-7-trifluoromethoxy-2,3-dihydro-1-benzoxepine C$_{19}$H$_{16}$F$_3$NO$_2$ MM=335.325

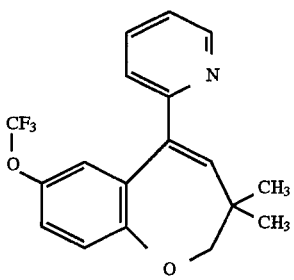

Formula 64

[M.p.=112° C.; cyclohexane; 85%]IR in cm$^{-1}$: 3070, 3045, 2960, 1585, 1560 $^1$H NMR (CDCl$_3$) in ppm: 8.59 (1H, m), 7.66 (1H, m), 7.13 (4H, m), 6.59 (1H, s), 5.91 (1H, s), 3.91 (2H, s), 1.17 (6H, s). 3,3 -Dimethyl-7-methylthio-5-(2-pyridyl) -2,3-dihydro-1-benzoxepine C$_{18}$H$_{19}$NOS MM=297.420

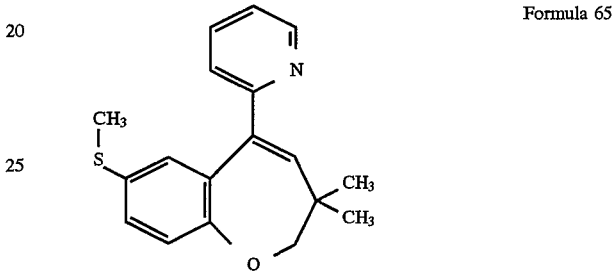

Formula 65

[B.p.$_{0.8\ mm\ Hg}$=140°–160° C.; 60%]IR in cm$^{-1}$: 2970, 2870, 1585, 1560 $^1$H NMR (CDCl$_3$) in ppm: 8.58 (1H, m), 7.65 (1H, m) , 6.96 (5H, m), 5.87 (1H, s), 3.90 (2H, s), 2.22 (3H, s), 1.19 (6H, s). 3,3 -Dimethyl-7-phenyl-5-(2-pyridyl)-2,3-dihydro-1-benzoxepine C$_{23}$H$_{21}$NO MM=327.425

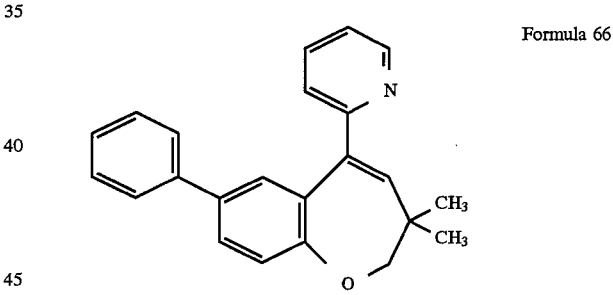

Formula 66

[M.p.=115°–120° C.; heptane; 42%]IR in cm$^{-1}$: 3050, 2950, 1600 $^1$H NMR (CDCl$_3$) in ppm: 8.60 (1H, m), 7.30 (11H, m), 5.91 (1H, s), 3.99 (2H, s), 1.21 (6H, s). 8-Bromo-3,3-dimethyl-5-(2-pyridyl)-2,3-dihydro-1-benzoxepine C$_{17}$H$_{16}$BrNO MM=330.224

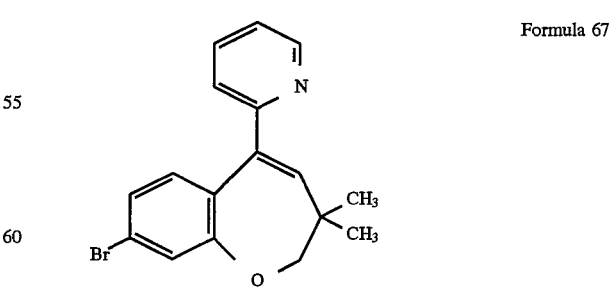

Formula 67

[yellow oil; 90%]IR in cm$^{-1}$: 3060, 2950, 1585, 1555, 1485, 1465 $^1$H NMR (CDCl$_3$) in ppm: 8.59 (1H, m) , 7.62 (1H, dd), 7.11 (4H, m), 6.61 (1H, d, J=8 Hz), 5.90 (1H, s), 3.95 (2H, s), 1.18 (6H, s). 7-Cyano-3,3-dimethyl-5-(2-pyridyl)-2,3-dihydro-1-benzoxepine C$_{18}$H$_{16}$N$_2$O MM=276.337

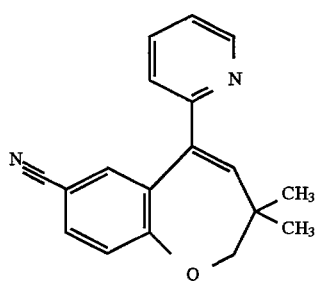

Formula 68

[chromatography with silica gel and cyclohexane/chloroform/methanol; 56/33/11; M.p.=155°–157° C., ethyl acetate; 57%]IR in cm$^{-1}$: 2960, 2220, 1590, 1570, 1495 $^1$H NMR (CDCl$_3$) in ppm: 8.55 (1H, m), 7.37 (6H, m), 5.90 (1H, s), 3.95 (2H, s), 1.20 (6H, s).

| | Elemental analysis | | | |
|---|---|---|---|---|
| | C | H | N | O |
| % Found | 78.06 | 5.94 | 10.14 | |
| % Calculated | 78.23 | 5.84 | 10.14 | 5.79 |

8-Cyano-3,3-dimethyl-5-(2-pyridyl)-2,3-dihydro-1-benzoxepine C$_{18}$H$_{16}$N$_2$O MM=276.337

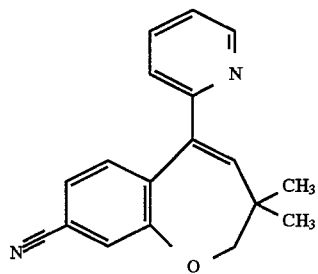

Formula 69

[chromatography with silica gel and dichloromethane; M.p.=132° C.; crystallization from heptane; 30%]IR in cm$^{-1}$: 2950, 2210, 1585, 1565, 1540, 1500 $^1$H NMR (CDCl$_3$) in ppm: 8.56 (1H, m), 7.66 (1H, m), 7.16 (4H, m), 6.83 (1H, d, J=8 Hz), 6.01 (1H, s), 3.95 (2H, s), 1.19 (6H, s). 3,3-Dimethyl-5-(2-pyridyl)-7-trifluoromethyl-2,3-dihydro-1-benzoxepine C$_{18}$H$_{16}$F$_3$NO MM=319.326

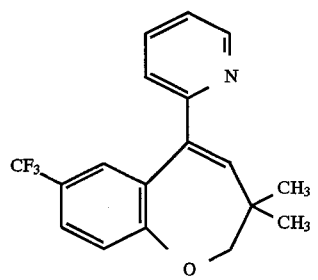

Formula 70

[M.p.=90° C.; isooctane; 60%]IR in cm$^{-1}$: 2960, 1585, 1565, 1500 3,3 -Dimethyl -5-(2-pyridyl )-8-trifluoromethyl-2,3-dihydro-1-benzoxepine C$_{18}$H$_{16}$F$_3$NO MM=319.326

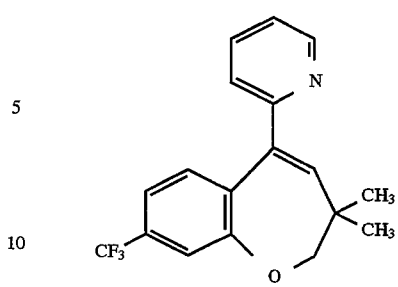

Formula 71

[oil; 85%]IR in cm$^{-1}$: 2960, 1585, 1565, 1500 $^1$H NMR (CDCl$_3$) in ppm: 8.60 (1H, m), 7.34 (6H, m), 6.00 (1H, s), 3.98 (2H, s), 1.19 (6H, s). 3,3-Dimethyl-5-(2-pyridyl)-7-pentafluoroethyl-2,3-dihydro-1-benzoxepine C$_{19}$H$_{16}$F$_5$NO MM=369.334

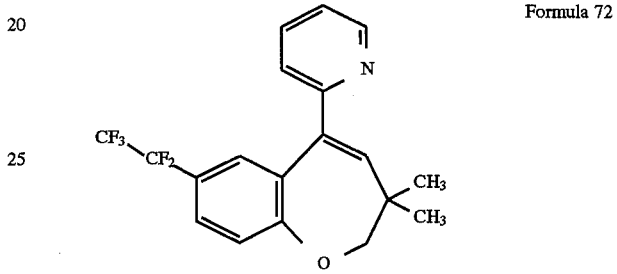

Formula 72

[oil; 90%]IR in cm$^{-1}$: 2960, 1590, 1565, 1500 6,8-Dichloro-3,3-dimethyl-5-(2-pyridyl)-2,3-dihydro-1-benzoxepine C$_{17}$H$_{15}$Cl$_2$NO MM=320.218

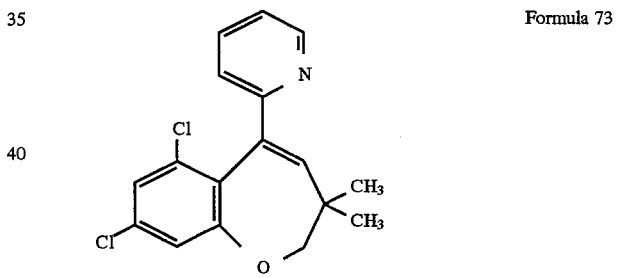

Formula 73

[oil]IR in cm$^{-1}$: 2960, 1585, 1545 $^1$H NMR (CDCl$_3$) in ppm: 8.47 (1H, m), 7.22 (5H, m), 6.50 (1H, s), 4.05 (2H, s), 1.10 (6H, s). 7,8-Dichloro-3,3-dimethyl-5-(2-pyridyl)-2,3-dihydro-1-benzoxepine C$_{17}$H$_{15}$Cl$_2$NO MM=320.218

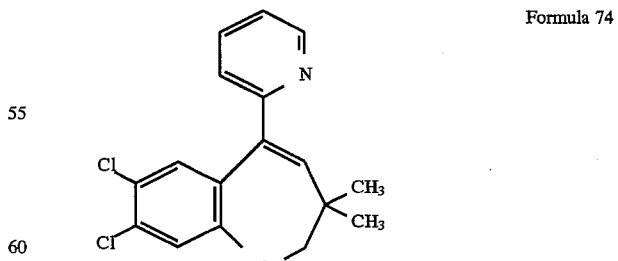

Formula 74

[M.p.=98° C.; hexane; 81%]IR in cm$^{-1}$: 2960, 1580, 1475 $^1$H NMR (CDCl$_3$) in ppm: 8.58 (1H, m), 7.40 (5H, m), 5.88 (1H, s), 3.90 (2H, s), 1.15 (6H, s). 7,9-Dichloro-3,3-dimethyl-5-(2-pyridyl)-2,3-dihydro-1-benzoxepine C$_{17}$H$_{15}$Cl$_2$NO MM=320.218

Formula 75

[M.p.=124° C.; heptane; 66%]IR in cm$^{-1}$: 2970, 1585, 1470 $^1$H NMR (CDCl$_3$) in ppm: 8.59 (1H, m), 7.45 (4H, m), 6.62 (1H, d, J=1.5 Hz), 5.95 (1H, s), 4.00 (2H, s), 1.21 (6H, s). 8,9 -Dichloro-3,3-dimethyl-5-(2 -pyridyl) -2,3 -dihydro-1-benzoxepine C$_{17}$H$_{15}$Cl$_2$NO MM=320.218

Formula 76

[M.p.=112° C.; heptane; 55 %]IR in cm$^{-1}$: 2970, 1580, 1475 $^1$H NMR (CDCl$_3$) in ppm: 8.62 (1H, m), 7.67 (1H, m), 7.15 (2H, m), 6.92 (1H, d, J=8 Hz), 6.57 (1H, d, J=8 Hz), 5.92 (1H, s), 4.02 (2H, s), 1.22 (6H, s). 7,8-Difluoro-3,3-dimehtyl-5-(2-pyridyl)-2,2-dihydro-1-benzoxepine C$_{17}$H$_{15}$F$_2$NO MM=287.308

Formula 77

[M.p.=86° C.; crystallization from pentane; 86%]IR in cm$^{-1}$: 3070, 2970, 1585, 1510 $^1$H NMR (CDCl$_3$) in ppm: 8.58 (1H, m), 7.68 (1H, m), 6.85 (4H, m), 5.85 (1H, s), 3.93 (2H, s), 1.20 (6H, s). 8-Chloro-7-fluoro-3,3-dimethyl-5-(2-pyridyl) -2,3 -dihydro-1-benzoxepine C$_{17}$H$_{15}$ClFNO MM=303.763

Formula 78

[M.p.=86° C.; 94%]IR in cm$^{-1}$: 2950, 1585, 1560, 1485 $^1$H NMR (CDCl$_3$) in ppm: 8.63 (1H, m), 7.68 (1H, m), 7.18 (3H, m), 6.55 (1H, d), 5.90 (1H, s), 3.92 (2H, s), 1.15 (6H, s). 9-Ethyl-7-fluoro-3,3-dimethyl-5-(2-pyridyl)-2,3-dihydro-1-benzoxepine C$_{19}$H$_{20}$NFO MM=297.372

Formula 79

[chromatography with silica gel and dichloromethane; 95%] IR in cm$^{-1}$: 2950, 1585 $^1$H NMR (CDCl$_3$) in ppm: 8.60 (1H, m), 7.64 (1H, m), 7.15 (2H, m), 6.70 (1H, dd, J=2 Hz, J=8 Hz), 6.30 (1H, dd, J=2 Hz, J=10 Hz.), 5.90 (1H, s), 3.90 (2H, s), 2.69 (2H, q), 1.20 (9H, m). 7,8 -Dimethoxy-3,3-dimethyl-5-(2-pyridyl)-2,3-dihydro-1-benzoxepine C$_{19}$H$_{21}$NO$_3$ MM=311.380

Formula 80

[M.p.=86° C.; 57%]IR in cm$^{-1}$: 2950, 1605, 1580, 1515 $^1$H NMR (CDCl$_3$) in ppm: 8.61 (1H, m), 7.63 (1H, m), 7.17 (2H, m), 6.59 (1H, s), 6.25 (1H, s), 5.76 (1H, s), 3.92 (2H, s), 3.56 (3H, s), 3.50 (3H, s), 1.16 (6H, s). 7-Cyano-3,3,8-trimethyl-5-(2-pyridyl) -2,3-dihydro-1-benzoxepine C$_{19}$H$_{18}$N$_2$O MM=290.364

Formula 81

[chromatography with silica gel and dichloromethane; M.p.=171° C., toluene; 32%]IR in cm$^{-1}$: 3060, 2970, 2220, 1610, 1585, 1560, 1495 $^1$H NMR (CDCl$_3$) in ppm: 8.59 (1H, m), 7.69 (1H, m), 7.19 (2H, m), 7.00 (1H, s), 6.90 (1H, s), 5.85 (1H, s), 3.95 (2H, s), 2.41 (3H, s), 1.19 (6H, s). 8-Cyano-3,3,7- trimethyl-5- (2-pyridyl) -2,3-dihydro-1-benzoxepine C$_{19}$H$_{18}$N$_2$O MM=290.364

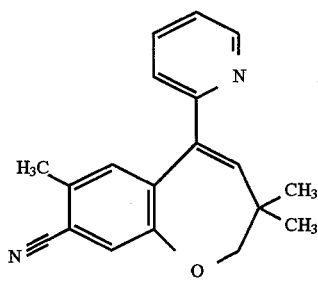

Formula 82

[M.p.=136° C.; hexane; 40%]IR in cm$^{-1}$: 3070, 2980, 2230, 1590, 1500 $^1$H NMR (CDCl$_3$) in ppm: 8.56 (1H, m) , 7.66 (1H, m) , 7.17 (1H, s) , 7.14 (2H, m) , 6.62 (1H, s) , 5.96 (1H, s) , 3.90 (2H, s), 2.27 (3H, s), 1.18 (6H, s). 3,3-Dimethyl-5-(2-pyridyl)-2,3,7,8,9,10-hexahydro-1-naphth[2,3-oxepine C$_{21}$H$_{23}$NO MM=305.419

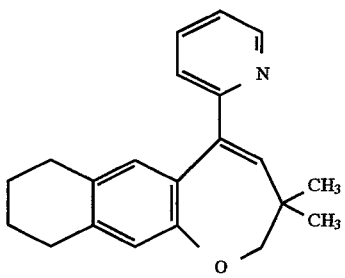

Formula 83

[M.p.=75° C.; crystallization from hexane; 88%]IR in cm$^{-1}$: 2930, 1610, 1580, 1560, 1500 $^1$H NMR (CDCl$_3$) in ppm: 8.56 (1H, m) , 7.60 (1H, m) , 7.17 (2H, m), 6.71 (1H, s), 6.40 (1H, s), 5.75 (1H, s), 3.90 (2H, s), 2.56 (4H, m), 1.70 (4H, m), 1.14 (6H, s). 8-Cyano-3,3-dimethyl-1-(2-pyridyl)-4,5-dihydro-3H-benzo-[f]-cycloheptene C$_{19}$H$_{18}$N$_2$ MM=274.365

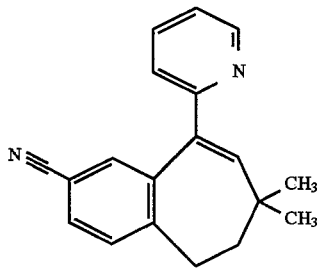

Formula 84

[chromatography with silica gel and ethyl acetate/hexane: 25/75 mixture; M.p.=120° C.; diisopropyl ether; 31%]IR in cm$^{-1}$: 2960, 2915, 2230, 1585, 1560 $^1$H NMR (CDCl$_3$) in ppm: 8.55 (1H, m), 7.62 (1H, m), 7.20 (5H, m), 6.30 (1H, s), 2.80 (2H, m), 1.88 (2H, m), 0.95 (6H, m). 7-Bromo-3,3-dimethyl-5-(3-pyridyl)-2,3-dihydro-1-benzoxepine C$_{17}$H$_{16}$BrNO MM=330.224

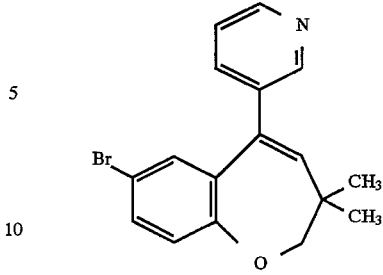

Formula 85

[M.p.=116° C.; heptane; 73%]IR in cm$^{-1}$: 2950, 1560, 1485, 1465 $^1$H NMR (CDCl$_3$) in ppm: 8.51 (2H, m), 7.35 (3H, m), 6.88 (2H, m), 5.74 (1H, s), 3.91 (2H, s), 1.17 (6H, s). 7-Cyano-3,3-dimethyl-5-(3-pyridyl)-2,3-dihydro-1-benzoxepine C$_{18}$H$_{16}$N$_2$O MM=276.237

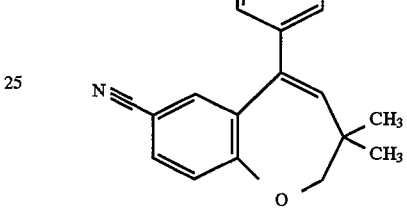

Formula 86

[chromatography with silica gel and cyclohexane/chloroform/methanol mixture: 56/33/11; M.p.=150° C.; heptane; 38%]IR in cm$^{-1}$: 3090, 2980, 2250, 1600, 1570, 1500 $^1$H NMR (CDCl$_3$) in ppm: 8.46 (2H, m) , 7.18 (5H, m) , 5.79 (1H, s), 3.95 (2H, s), 1.18 (6H, s). 7,8-Dichloro-3,3-dimethyl-5-(3-pyridyl)-2,3-dihydro-1-benzoxepine C$_{17}$H$_{15}$Cl$_2$NO MM=320.218

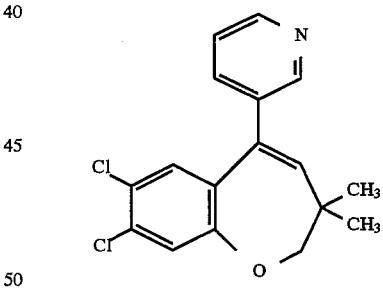

Formula 87

[M.p.=112° C.; diisopropyl ether; 36%]IR in cm$^{-1}$: 3020, 2970, 1590, 1565, 1540 $^1$H NMR (CDCl$_3$) in ppm: 8.54 (2H, m) , 7.35 (2H, m) , 7.10 (1H, s), 6.77 (1H, s), 5.72 (1H, s), 3.92 (2H, s), 1.17 (6H, s).

EXAMPLE NO. 7

7-Ethyl-3,3-dimethyl-5-(2-pyridyl)-2,3,4,5-tetrahydro-1-benzoxepine C$_{19}$H$_{23}$NO MM=281.386

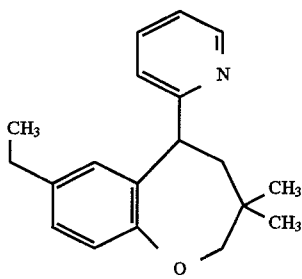

Formula 88

A solution of 7-ethyl-3,3-dimethyl-5-(2-pyridyl)-2,3-dihydro-1-benzoxepine (75 g, 0.26 mol) in 96% ethanol (95 ml) is placed in a 125 ml autoclave. Palladium containing 50% moisture is then added (0.3 g at 10% on charcoal).

The hydrogen is introduced under pressure: 180 bar.

The whole mixture is stirred for 4 hours at 80° C.

The suspension is filtered and concentrated under reduced pressure.

[yellow oil; 78%]IR in cm$^{-1}$: 2960, 1590, 1570, 1495 $^1$H NMR (CDCl$_3$) in ppm: 8.63 (1H, m) , 7.30 (5H, m) , 6.19 (1H, s), 4.54 (1H, dd, J=2 Hz, J=9 Hz), 3.89 (1H, d, 12 Hz), 3.48 (1H, d, J=12 Hz), 2.42 (3H, m), 1.67 (1H, m), 1.20 (3H, s), 1.03 (3H, t), 0.85 (3H, s).

EXAMPLE NO. 8

3,3-Dimethyl-7-nitro-5-(4-nitro-2-pyridyl) -2,3-dihydro-1-benzoxepine C$_{17}$H$_{15}$N$_3$O$_5$ MM=341.323

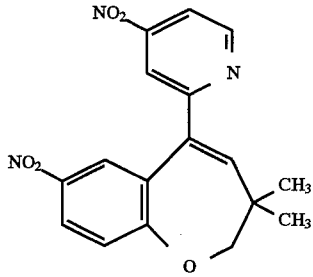

Formula 89

A mixture of 3,3-dimethyl-5-(2-pyridyl)-1-benzoxepin-5-ol (5 g, 0.018 mol) and of a commercial concentrated sulfuric acid solution (32 ml) is cooled to 0° C. Sodium nitrate (1.8 g, 0.02 mol) is added in portions over 2 hours at 0° C. with stirring. The reaction mixture is then poured into ice-cold water (100 ml) and extracted with dichloromethane.

The organic phase is washed with water, dried over anhydrous sodium sulfate and concentrated under reduced pressure.

[1.4 g; M.p.=180° C.; ethyl acetate; 25%]IR in cm$^{-1}$: 3100, 2970, 1545, 1530, 1480 $^1$H NMR (CDCl$_3$) in ppm: 8.56 (1H, m) , 8.34 (1H, d, J=2.50 Hz), 7.90 (1H, d, J=2.50 Hz), 7.48 (3H, m), 6.15. (1H, s), 4.15 (2H, s), 1.25 (6H, s).

By using the process described for Example 4, the following compounds are prepared.

7-Bromo-3,3-dimethyl-5-(2-pyridyl N-oxide)-2,3-dihydro-1-benzoxepine C$_{17}$H$_{16}$BrNO$_2$ MM=346.223

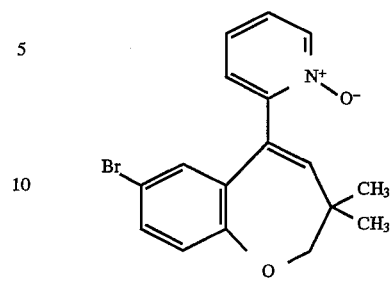

Formula 90

[chromatography with silica gel and ethyl acetate; M.p.= 158°–160° C.; ethyl acetate; 29%]IR in cm$^{-1}$: 3040, 2960, 1480 $^1$H NMR (CDCl$_3$) in ppm: 8.25 (1H, m), 6.98 (6H, m), 5.82 (1H, s), 3.95 (2H, s), 1.19 (6H, s).

| | Elemental analysis | | | | |
|---|---|---|---|---|---|
| | C | H | Br | N | O |
| % Found | 59.24 | 4.68 | 23.09 | 3.91 | |
| % Calculated | 58.97 | 4.66 | 23.08 | 4.05 | 9.24 |

7-Chloro-3,3-methyl-(2-pyridyl N-oxide)-2,3-dihydro-1-benzoxepine C$_{17}$H$_{16}$ClNO$_2$ MM=301.772

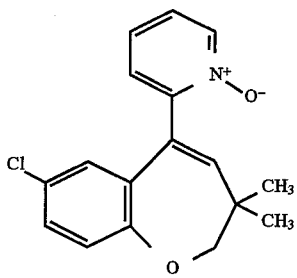

Formula 91

[M.p.=168°–170° C.; acetone; 15%]IR in cm$^{-1}$: 2960, 1480 $^1$H NMR (CDCl$_3$) in ppm:8.25 (1H, m), 6.93 (6H, m), 5.84 (1H, s), 3.95 (2H, s), 1.19 (6H, s).

| | Elemental analysis | | | | |
|---|---|---|---|---|---|
| | C | H | Cl | N | O |
| % Found | 67.85 | 5.19 | 11.91 | 4.51 | |
| % Calculated | 67.66 | 5.34 | 11.75 | 4.64 | 10.60 |

7-Fluoro-3,3-dimethyl-5-(2-pyridyl N-oxide) -2,3-dihydro-1-benzoxepine C$_{17}$H$_{16}$PNO$_2$ MM=269.318

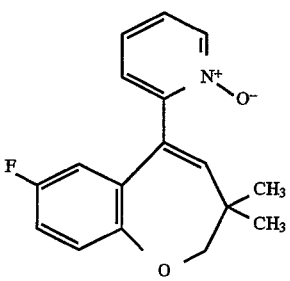

Formula 92

[M.p.=814°–185° C.; ethyl acetate; 28%]IR in cm$^{-1}$: 3050, 2950, 1490 $^1$H NMR (CDCl$_3$) in ppm: 8.23 (1H, m) , 6.75 (6H, m) , 5.83 (1H, s), 3.96 (2H, s), 1.19 (6H, s).

| Elemental analysis | | | | | |
|---|---|---|---|---|---|
| | C | H | F | N | O |
| % Found | 71.62 | 5.57 | 6.91 | 4.81 | |
| % Calculated | 71.56 | 5.65 | 6.66 | 4.91 | 11.22 |

3,3-Dimethyl-5-(2-pyridyl N-oxide)-2,3-dihydro-1-benzoxepine $C_{17}H_{17}NO_2$ MM=265.327

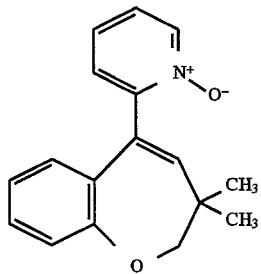

Formula 93

[M.p.=188°–189° C.; isopropanol; 19%]IR in $cm^{-1}$: 3050, 3010, 2960, 2870, 1605, 1570, 1490 $^1$H NMR (CDCl$_3$) in ppm: 8.20 (1H, m), 6.91 (7H, m), 5.80 (1H, s), 4.00 (2H, s), 1.21 (6H, s).

| Elemental analysis | | | | |
|---|---|---|---|---|
| | C | H | N | O |
| % Found | 76.53 | 6.45 | 5.05 | |
| % Calculated | 76.38 | 6.41 | 5.24 | 11.97 |

3,3,3,7-Trimethyl-5-(2-pyridyl N-oxide)-2,3-dihydro-1-benzoxepine $C_{18}H_{19}NO_2$ MM=281.354

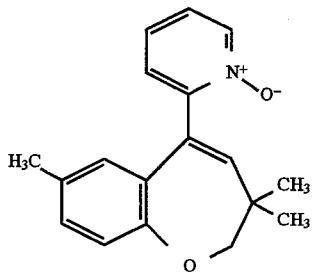

Formula 94

[M.p.=146°–147° C.; ethyl acetate]IR in $cm^{-1}$: 3030, 2960, 2930, 2870, 1605, 1570, 1490 $^1$H NMR (CDCl$_3$) in ppm: 8.23 (1H, m) , 7.21 (3H, m) , 6.89 (2H, m), 6.34 (1H, m), 5.75 (1H, s), 3.95 (2H, s), 2.11 (3H, s), 2.11 (3H, s), 1.16 (6H, s)

| Elemental analysis | | | | |
|---|---|---|---|---|
| | C | H | N | O |
| % Found | 77.04 | 6.75 | 5.07 | |
| % Calculated | 76.84 | 6.81 | 4.98 | 11.37 |

7-Ethyl-3,3-dimethyl-5-(2-pyridyl N-oxide)-2,3-dihydro-1-benzoxepine $C_{19}H_{21}NO_2$ MM=295.369

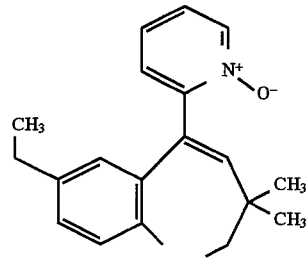

Formula 95

[M.p.=126°–129° C.; ethyl acetate/diisopropyl ether: 2/1; 20%]IR in $cm^{-1}$: 3030, 2960, 2930, 2870, 1610, 1575, 1500 $^1$H NMR (CDCl$_3$) in ppm: 8.28 (1H, m), 7.23 (3H, m), 6.94 (2H, m), 6.38 (1H, m), 5.78 (1H, s), 3.96 (2H, s), 2.43 (2H, q), 1.18 (6H, s), 1.04 (3H, t).

| Elemental analysis | | | | |
|---|---|---|---|---|
| | C | H | N | O |
| % Found | 77.48 | 7.26 | 4.79 | |
| % Calculated | 77.26 | 7.17 | 4.74 | 10.83 |

7-Isopropyl-3,3-dimethyl-5-(2-pyridyl N-oxide)-2,3-dihydro-1-benzoxepine $C_{20}H_{23}NO_2$ MM=309.407

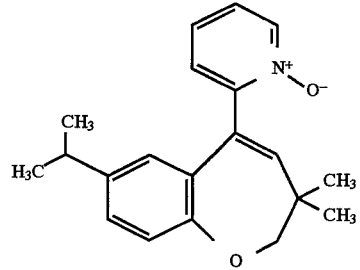

Formula 96

M.p.=162°–164° C.; ethyl acetate]IR in $cm^{-}$: 3025, 2950, 1500 $^1$NMR (CDCl$_3$) in ppm: 8.26 (1H, m), 7.08 (5H, m), 6.38 (1H, s), 5.75 (1H, s), 3.95 (2H, s), 2.65 (1H, m), 1.10 (12H, m)

| Elemental analysis | | | | |
|---|---|---|---|---|
| | C | H | N | O |
| % Found | 77.43 | 7.50 | 4.49 | |
| % Calculated | 77.64 | 7.49 | 4.53 | 10.34 |

3,3-Dimethyl-7-(1-methylpropyl)-5-(2-pyridyl N-oxide)-2,3-dihydro-1-benzoxepine $C_{23}H_{25}NO_2$ MM=323.434

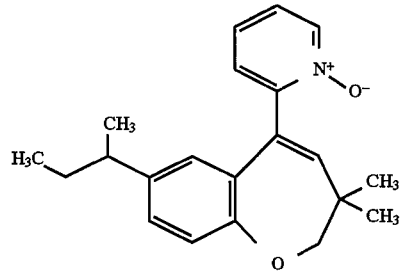

Formula 97

[chromatography with silica gel and dichloromethane/methanol: 99/1; M.p.=110°–112° C.; cyclohexane]
IR in cm$^{-1}$: 3030, 2950, 1605, 1500, 1480 $^1$H NMR (CDCl$_3$) in ppm: 8.28 (1H, m), 7.20 (3H, m), 6.91 (2H, m), 6.33 (1H, s), 5.77 (1H, s), 3.98 (2H, s), 2.32 (1H, m), 1.18 (6H, s), 1.05 (8H, m)

| Elemental analysis | | | | |
|---|---|---|---|---|
| | C | H | N | O |
| % Found | 77.93 | 7.81 | 4.24 | |
| % Calculated | 77.98 | 7.79 | 4.33 | 9.89 |

7-Methoxy-3,3-dimethyl-5-(2-pyridyl N-oxide)-2,3-dihydro-1-benzoxepine C$_{18}$H$_{19}$NO$_3$ MM=297.353

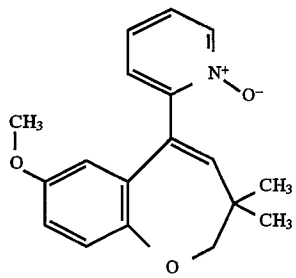

Formula 98

[M.p.=164°–166° C.; ethyl acetate]IR in cm$^{-1}$: 3050, 2960, 1615, 1580, 1510, 1495 $^1$H NMR (CDCl$_3$) in ppm: 8.20 (1H, m), 6.93 (5H, m), 6.14 (1H, m), 5.79 (1H, s), 3.93 (2H, s), 3.56 (3H, s), 1.15 (6H, s)

| Elemental analysis | | | | |
|---|---|---|---|---|
| | C | H | N | O |
| % Found | 73.00 | 6.49 | 4.71 | |
| % Calculated | 72.70 | 6.44 | 4.71 | 16.14 |

3,3-Dimethyl-5-(2-pyridyl N-oxide)-7-trifluoromethoxy-2,3-dihydro-1-benzoxepine C$_{18}$H$_{16}$F$_3$NO$_3$ MM=351.325

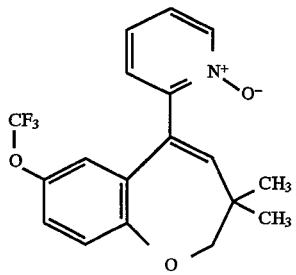

Formula 99

[M.p.=157°–159° C.; ethyl acetate]IR in cm$^{-1}$: 3070, 2970, 1495 $^1$H NMR (CDCl$_3$) in ppm: 8.24 (1H, m), 7.14 (5H, m), 6.39 (1H, s), 5.85 (1H, s), 3.96 (2H, s), 1.19 (6H, s).

| Elemental analysis | | | | |
|---|---|---|---|---|
| | C | H | F | N | O |
| % Found | 61.79 | 4.77 | 16.38 | 3.91 | |
| % Calculated | 61.53 | 4.59 | 16.22 | 3.99 | 13.66 |

3,3-Dimethyl-5-(2-pyridyl N-oxide)-7-trifluoromethyl-2,3-dihydro-1-benzoxepine C$_{15}$H$_{16}$F$_3$NO$_2$ MM=335.325

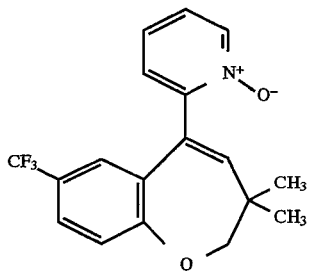

Formula 100

[M.p.=152°–153° C.; ethyl acetate/hexane: ½]IR in cm$^{-1}$: 3060, 2970, 1610, 1495 $^1$H NMR (CDCl$_3$) in ppm: 8.20 (1H, m), 7.13 (6H, m), 5.89 (1H, s), 4.00 (2H, s), 1.18 (6H, s)

| Elemental analysis | | | | |
|---|---|---|---|---|
| | C | H | F | N | O |
| % Found | 64.55 | 4.76 | 17.55 | 4.10 | |
| % Calculated | 64.47 | 4.81 | 17.00 | 4.18 | 9.54 |

3,3-Dimethyl-7-methylsulfonyl-5-(2-pyridyl N-oxide)-2,3-dihydro-1-benzoxepine C$_{18}$H$_{19}$NO$_4$S MM=345.418

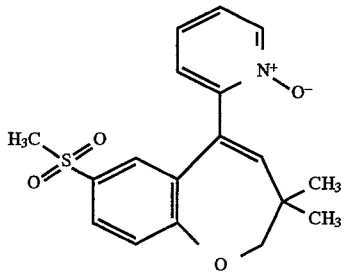

Formula 101

[chromatography with silica gel and acetone; M.p.=200° C., diisopropyl ether]IR in cm$^{-1}$: 2970, 1600, 1565, 1490 $^1$H NMR (CDCl$_3$) in ppm: 8.23 (1H, m), 7.65 (1H, m), 7.19 (5H, m), 5.97 (1H, s), 4.04 (2H, s), 2.91 (3H, s), 1.22 (6H, s)

| Elemental analysis | | | | |
|---|---|---|---|---|
| | C | H | N | O | S |
| % Found | 62.86 | 5.64 | 3.95 | 18.25 | 9.25 |
| % Calculated | 62.59 | 5.54 | 4.06 | 18.53 | 9.28 |

3,3-Dimethyl-7-phenyl-5-(2-pyridyl N-oxide)-2,3-dihydro-1-benzoxepine C$_{23}$H$_{21}$NO$_2$ MM=343.424

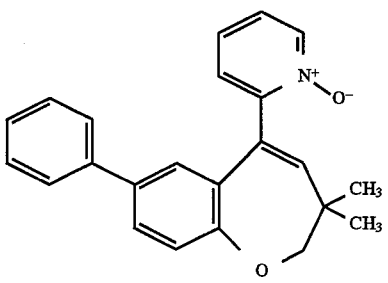

Formula 102

[chromatography with silica gel and ethyl acetate/chloroform/methanol mixture: 60/30/10; M.p.=165°–168°

C.; IR in cm$^{-1}$: 3050, 2960, 1605 $^1$H NMR (CDCl$_3$) in ppm: 8.24 (1H, m), 7.08 (11H, m), 5.82 (1H, s), 3.98 (2H, s), 1.16 (6H, s)

| Elemental analysis | | | | |
|---|---|---|---|---|
| | C | H | N | O |
| % Found | 80.04 | 6.20 | 4.01 | |
| % Calculated | 80.44 | 6.16 | 4.08 | 9.32 |

8-Bromo-3,3-dimethyl-5-(2-pyridyl N-oxide)-2,3-dihydro-1-benzoxepine C$_{17}$H$_{16}$BrNO$_3$ MM=346.223

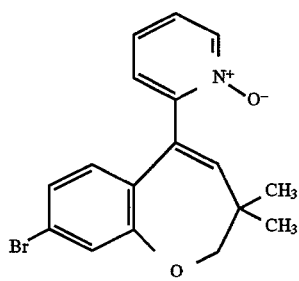

Formula 103

[chromatography on silica gel and dichloromethane/ methanol: 98/2; M.p.=135°–137° C.; diisopropyl ether/ethyl acetate: 60/40]IR in cm$^{-1}$: 3080, 2970, 1590, 1550, 1480 $^1$H NMR (CDCl$_3$) in ppm: 8.21 (1H, m) , 7.09 (5H, m) , 6.40 (1H, d, J=8 Hz), 5.81 (1H, s), 3.95 (2H, s), 1.17 (6H, s)

| Elemental analysis | | | | | |
|---|---|---|---|---|---|
| | C | H | Br | N | O |
| % Found | 59.23 | 4.70 | 22.94 | 3.97 | |
| % Calculated | 58.97 | 4.66 | 23.08 | 4.05 | 9.24 |

7-Cyano-3,3-dimethyl-5-(2-pyridyl N-oxide)-2,3-dihydro-1-benzoxepine C$_{18}$H$_{16}$N$_2$O$_2$ MM=292.337

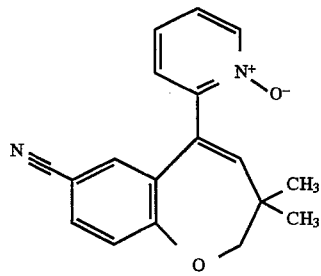

Formula 104

[M.p.=206°–207° C.; ethyl acetate; 33%]IR in cm$^{-1}$: 2985, 2220, 1595, 1560, 1490 $^1$H NMR (CF$_3$COOD) in ppm: 8.79 (1H, m), 8.05 (4H, m), 7.25 (1H, d, J=8 Hz), 6.88 (1H, d, J=2 Hz), 6.22 (1H, s), 4.15 (2H, s), 1.30 (6H, s)

| Elemental analysis | | | | |
|---|---|---|---|---|
| | C | H | N | O |
| % Found | 74.09 | 5.57 | 9.40 | |
| % Calculated | 73.95 | 5.52 | 9.58 | 10.95 |

8-Cyano-3,3-dimethyl-5-(2-pyridyl N-oxide)-2,3-dihydro-1-benzoxepine C$_{18}$H$_{16}$N$_2$O$_2$ MM=292.337

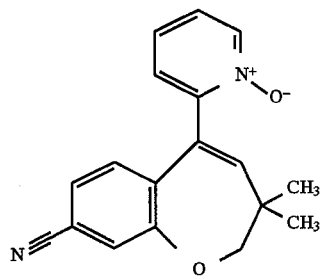

Formula 105

[chromatography with silica gel and dichloromethane/ methanol: 98/2: M.p.=195°–197° C.; ethanol]IR in cm$^{-1}$: 3090, 2970, 2230, 1550 $^1$H NMR (CDCl$_3$) in ppm: 8.20 (1H, m), 7.18 (5H, m), 6.64 (1H, d, J=8 Hz), 5.95 (1H, s), 3.96 (2H, s), 1.20 (6H, s).

| Elemental analysis | | | | |
|---|---|---|---|---|
| | C | H | N | O |
| % Found | 74.21 | 5.61 | 9.77 | |
| % Calculated | 73.95 | 5.52 | 9.58 | 10.95 |

3,3-Dimethyl-5-(2-pyridyl N-oxide)-8-trifluromethyl-2,3-dihydro-1-benzoxepine C$_{19}$H$_{16}$F$_3$NO$_2$ MM=335.325

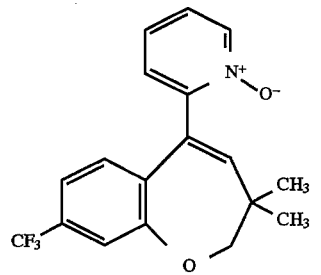

Formula 106

M.p.=130°–131° C.; hexane; 25%]IR in cm$^{-1}$: 3060, 2960, 1570, 1485 $^1$H NMR (CDCl$_3$) in ppm: 8.25 (1H, m) , 7.03 (6H, s) , 5.95 (1H, s), 4.01 (2H, s), 1.19 (6H, s)

| Elemental analysis | | | | | |
|---|---|---|---|---|---|
| | C | H | F | N | O |
| % Found | 64.74 | 4.93 | 17.00 | 4.18 | |
| % Calculated | 64.47 | 4.81 | 17.00 | 4.18 | 9.54 |

3,3-Dimethyl-5-(2-pyridyl N-oxide)-7-pentafluoroethyl-2,3-dihydro-1-benzoxepine C$_{19}$H$_{16}$F$_5$NO$_2$ MM=385.333

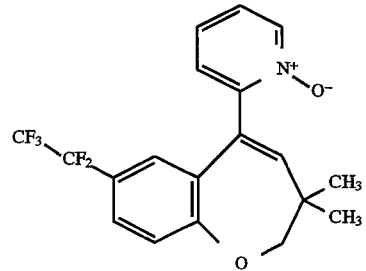

Formula 107

[M.p.=161°–162° C.; ethyl acetate]IR in cm$^{-1}$: 3070, 2970, 1610, 1585, 1600, 1590 $^1$H NMR (CDCl$_3$) in ppm: 8.25 (1H, m), 7.98 (6H, m), 5.93 (1H, s), 4.03 (2H, s), 1.20 (6H, s)

| Elemental analysis | | | | |
|---|---|---|---|---|
| | C | H | F | N | O |
| % Found | 59.52 | 4.31 | 24.27 | 3.62 | |
| % Calculated | 59.22 | 4.19 | 24.65 | 3.64 | 8.30 |

3,3,-Dimethyl-7-nitro-5-(4-nitro-2-pyridyl N-oxide)-2,3-dihydro-1-benzoxepine C$_{17}$H$_{15}$N$_3$O$_6$ MM=357.322

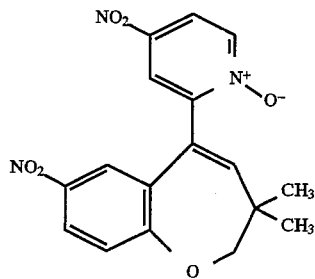

Formula 108

[chromatography with silica gel and ethyl acetate/chloroform/methanol: 60/30/10; M.p.=228° C., methanol]IR in cm$^{-1}$: 3100, 2970, 1545, 1530, 1480 $^1$H NMR (CDCl$_3$) in ppm: 8.37 (1H, d, J=2.70 Hz), 8.25 (1H, m, J=2.50 Hz), 7.65 (1H, d, J=2.70 Hz), 7.38 (3H, m, J=2.50 Hz), 6.17 (1H, s), 4.21 (2H, s), 1.28 (6H, s)

| Elemental analysis | | | | |
|---|---|---|---|---|
| | C | H | N | O |
| % Found | 57.35 | 4.25 | 11.49 | |
| % Calculated | 57.14 | 4.23 | 11.76 | 26.86 |

8-Cyano-3,3-dimethyl-1-(2-pyridyl N-oxide)-4,5-dihydro-3H-benzo[f]cycloheptane C$_{19}$H$_{18}$N$_2$O MM=290.364

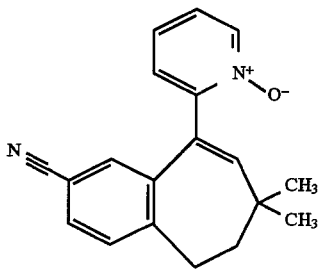

Formula 109

[chromatography with silica gel and cyclohexane/chloroform/methanol mixture: 70/20/10; M.p. =189° C., toluene; 42%]IR in cm$^{-1}$: 2950, 2225, 1595 $^1$H NMR (CDCl$_3$) in ppm: 8.08 (1H, m), 7.27 (5H, m), 6.85 (1H, s) 5.92 (1H, s), 2.93 (2H, m), 1.88 (2H, m), 0.95 (6H, m)

| Elemental analysis | | | | |
|---|---|---|---|---|
| | C | H | N | O |
| % Found | 78.30 | 5.90 | 9.39 | |
| % Calculated | 78.59 | 6.25 | 9.65 | 5.51 |

6,8-Dichloro-3,3-dimethyl-5-(2-pyridyl N-oxide)-3,3-dihydro-1-benzoxepine C$_{17}$H$_{15}$Cl$_2$NO$_2$ MM=336.217

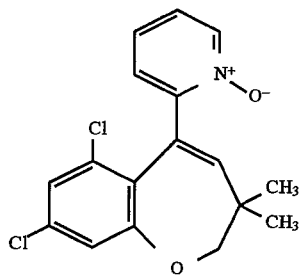

Formula 110

[M.p.=163°–164° C.; ethyl acetate]IR in cm$^{-1}$: 3050, 2970, 1590, 1550 $^1$H NMR (CDCl$_3$) in ppm: 8.09 (1H, m), 7.47 (5H, m), 6.21 (1H, s), 4.00 (2H, s), 1.15 (6H, s)

| Elemental analysis | | | | |
|---|---|---|---|---|
| | C | H | Cl | N | O |
| % Found | 60.75 | 4.70 | 21.26 | 4.12 | |
| % Calculated | 60.73 | 4.50 | 21.09 | 4.17 | 9.52 |

7,8-Dichloro-3,3-dimethyl-5-(2-pyridyl N-oxide)-2,3-dihydro-1-benzoxepine C$_{17}$H$_{15}$Cl$_2$NO$_2$ MM=336.217

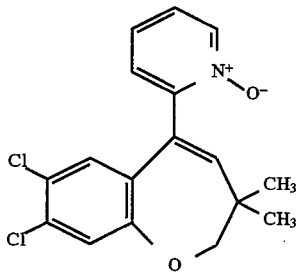

Formula 111

[M.p.=173°–174° C.; ethyl acetate; 37%]IR in cm$^{-1}$: 3070, 2960, 1475 $^1$H NMR (CDCl$_3$) in ppm: 8.20 (1H, m), 7.20 (4H, m), 6.60 (1H, s), 5.85 (1H, s), 3.95 (2H, s), 1.15 (6H, s)

| Elemental analysis | | | | |
|---|---|---|---|---|
| | C | N | Cl | N | O |
| % Found | 60.47 | 4.46 | 21.11 | 4.12 | |
| % Calculated | 60.73 | 4.50 | 21.09 | 4.17 | 9.52 |

7,9-Dichloro-3,3-dimethyl-5-(2-pyridyl N-oxide)-2,3-dihydro-1-benzoxepine C$_{17}$H$_{15}$Cl$_2$NO$_2$ MM=336.217

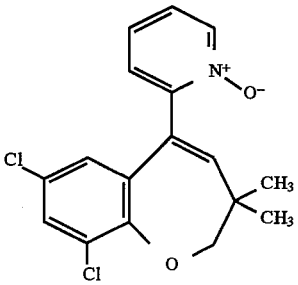

Formula 112

[M.p.=155°–157° C.; diisopropyl ether/ethyl acetate: 70/30; 30 %]IR in cm$^{-1}$: 3035, 1470, 1419 $^1$H NMR (CDCl$_3$) in ppm: 8.22 (1H, m), 7.34 (4H, m), 6.42 (1H, d, J=2 Hz), 5.88 (1H, s), 4.02 (2H, s), 1.21 (6H, s)

| Elemental analysis | | | | | |
|---|---|---|---|---|---|
| | C | H | Cl | N | O |
| % Found | 60.83 | 4.55 | 20.82 | 4.16 | |
| % Calculated | 60.73 | 4.50 | 21.09 | 4.17 | 9.52 |

8,9-Dichloro-3,3-dimethyl-5-(2-pyridyl N-oxide)-2,3-dihydro-1-benzoxepine $C_{17}H_{15}Cl_2NO_2$ MM=336.217

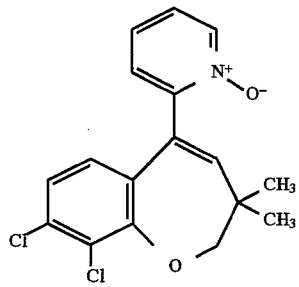

Formula 113

[M.p.=168° C.; ethyl acetate; 26%]IR in cm$^{-1}$: 2960, 1470, 1422 $^1$H NMR (CDCl$_3$) in ppm: 8.20 (1H, m), 7.25 (3H, mR), 6.95 (1H, d, J=8 Hz), 6.42 (1H, d, J=8 Hz), 5.85 (1H, s), 4.07 (2H, s), 1.24 (6H, s)

| Elemental analysis | | | | | |
|---|---|---|---|---|---|
| | C | H | Cl | N | O |
| % Found | 61.14 | 4.71 | 21.21 | 4.07 | |
| % Calculated | 60.73 | 4.50 | 21.09 | 4.17 | 9.52 |

7,8-Difluoro-3,3-dimethyl-5-(2-pyridyl N-oxide)-2,3-dihydro-1-benzoxepine $C_{17}H_{15}F_2NO_2$ MM=303.308

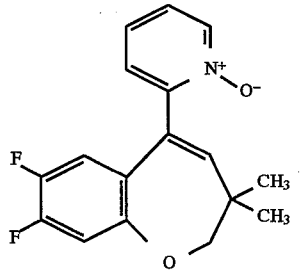

Formula 114

[M.p.=163°–165° C.; ethyl acetate]IR in cm$^{-1}$: 3060, 2965, 1600, 1515 $^1$H NMR (CDCl$_3$) in ppm: 8.23 (1H, m), 7.28 (3H, m), 6.80 (1H, dd, J=7.0 Hz), 6.35 (1H, dd, J=8.0 Hz), 5.80 (1H, s), 3.95 (2H, s), 1.18 (6H, s)

| Elemental analysis | | | | | |
|---|---|---|---|---|---|
| | C | H | F | N | O |
| % Found | 67.36 | 4.56 | 12.73 | 4.95 | |
| % Calculated | 67.32 | 4.99 | 12.53 | 4.62 | 10.55 |

8-Chloro-7-fluoro-3,3-dimethyl-5-(2-pyridyl N-oxide)-2,3-dihydro-1-benzoxepine $C_{17}H_{15}ClFNO_2$ MM=319.762

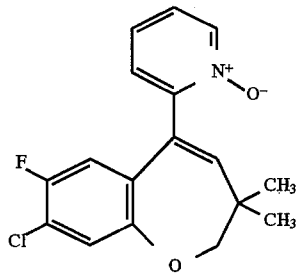

Formula 115

[M.p.=149°–151° C.; ethyl acetate]IR in cm$^{-1}$: 3050, 2970, 1485 $^1$H NMR (CDCl$_3$) in ppm: 8.20 (1H, m), 7.15 (4H, m), 6.35 (1H, d), 5.85 (1H, s), 3.93 (2H, s), 1.14 (6H, s)

| Elemental analysis | | | | | |
|---|---|---|---|---|---|
| | C | H | Cl | F | N | O |
| % Found | 64.04 | 4.82 | 11.16 | 5.91 | 4.41 | |
| % Calculated | 63.85 | 4.73 | 11.09 | 5.94 | 4.38 | 10.01 |

9-Ethyl-7-fluoro-3,3-dimethyl-5-(2-pyridyl N-oxide)-2,3-dihydro-1-benzoxepine $C_{19}H_{20}NFO_2$ MM=313.371

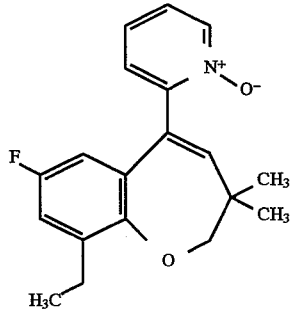

Formula 116

[chromatography with silica gel and acetone/ethyl acetate mixture: 50/50; M.p.=120°–2° C.; diisopropyl ether]IR in cm$^{-1}$: 2960, 2940, 1610, 1590 $^1$H NMR (CDCl$_3$) in ppm: 8.20 (1H, m), 7.20 (3H, m), 6.69 (1H, dd, J=2 Hz, J=8 Hz), 6.25 (1H, dd, J=2 Hz, J=10 Hz), 5.79 (1H, s), 3.94 (2H, s), 2.66 (2H, q), 1.19 (6H, s), 1.16 (3H, t).

| Elemental analysis | | | | |
|---|---|---|---|---|
| | C | H | F | N | O |
| % Found | 73.12 | 6.54 | 6.18 | 4.58 | |
| % Calculated | 72.82 | 6.43 | 6.06 | 4.47 | 10.21 |

7,8-Dimethoxy-3,3-dimethyl-5-(2-pyridyl N-oxide)-2,3-dihydro-1-benzoxepine $C_{15}H_{21}NO_4$ MM=327.379

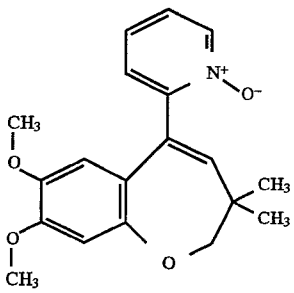

Formula 117

[chromatography with silica gel and dichloromethane/methanol: 98/2; M.p.=146° C.; ethyl acetate]IR in cm$^{-1}$: 3110, 2950, 1615, 1520, 1490 $^1$H NMR (CDCl$_3$) in ppm: 8.26 (1H, m), 7.25 (3H, m), 6.57 (1H, s), 6.08 (1H, s), 5.70 (1H, s), 3.99 (2H, s), 3.81 (3H, s), 3.56 (3H, s), 1.19 (6H, s).

| | Elemental analysis | | | |
|---|---|---|---|---|
| | C | H | N | O |
| % Found | 69.86 | 6.70 | 4.12 | |
| % Calculated | 69.70 | 6.47 | 4.28 | 19.55 |

7-Cyano-3,3,8-trimethyl-5-(2-pyridyl N-oxide)-2,3-dihydro-1-benzoxepine $C_{19}H_{18}N_2O_2$ MM=306.363

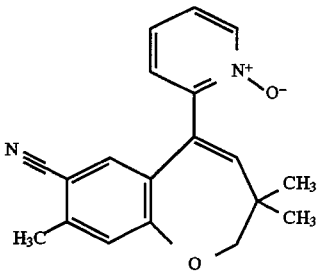

Formula 118

[chromatography with silica gel and chloroform/methanol mixture: 98/2; M.p.=230°–235° C.; toluene/diisopropyl ether]IR in cm$^{-1}$: 3060, 2950, 2210, 1605, 1495

| | Elemental analysis | | | |
|---|---|---|---|---|
| | C | N | N | O |
| % Found | 74.39 | 6.00 | 8.93 | |
| % Calculated | 74.49 | 5.92 | 9.15 | 10.45 |

[Cyano-3,3,7-trimethyl-5-(2-pyridyl N-oxide)-2,3-dihydro-1-benzoxepine $C_{19}H_{18}N_2O_2$ MM=306.363

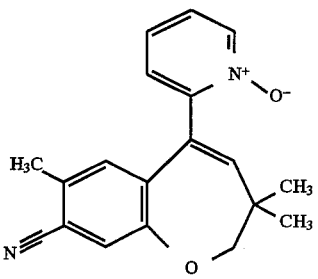

Formula 119

[M.p.=182° C.; toluene; 30%]IR in cm$^{-1}$: 3070, 2960, 2225, 1605, 1545, 1490 $^1$H NMR (CDCl$_3$) in ppm: 8.20 (1H, m), 7.22 (4H, m), 6.44 (1H, s), 5.90 (1H, s), 3.92 (2H, s), 2.26 (3H, s), 1.18 (6H, s)

| | Elemental analysis | | | |
|---|---|---|---|---|
| | C | H | N | O |
| % Found | 74.70 | 5.91 | 9.04 | |
| % Calculated | 74.49 | 5.92 | 9.15 | 10.45 |

3,3-Dimethyl-5-(2-pyridyl N-oxide)-2,3,7,8,9,10-hexahydro-1-naphth[2,3-b]oxepine $C_{21}H_{23}NO_2$ MM=321.418

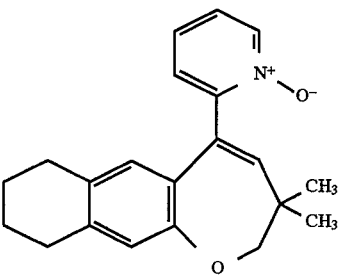

Formula 120

[chromatography with silica gel and dichloromethane/methanol: 98/2; M.p.=184° C.; toluene]IR in cm$^{-1}$: 2930, 1610, 1550, 1500 $^1$H NMR (CDCl$_3$) in ppm: 8.22 (1H, m), 7.22 (3H, m), 6.72 (1H, s), 6.24 (1H, s), 5.69 (1H, s), 3.95 (2H, s), 2.58 (4H, m), 1.70 (4H, m), 1.16 (6H, s).

| | Elemental analysis | | | |
|---|---|---|---|---|
| | C | H | N | O |
| % Found | 78.30 | 7.39 | 4.48 | |
| % Calculated | 78.47 | 7.21 | 4.36 | 9.96 |

7-Ethyl-3,3-dimethyl-5-(2-pyridyl N-oxide)-2,3,4,5-tetrahydro-1-benzoxepine $C_{19}H_{23}NO_2$ MM=297.385

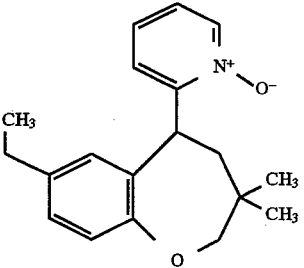

Formula 121

[m.p.=88°–89° C.; diisopropyl ether]IR in cm$^{-1}$: 3060, 3020, 2960, 2930, 2870, 1610, 1490 $^1$NMR (CDCl$_3$) in ppm: 8.28 (1H, m), 7.16 (3H, m), 6.96 (2H, m), 6.45 (1H, m), 5.20 (1H, dd, J=2 Hz, J=9 Hz), 3.71 (2H, s), 2.50 (3H, m), 1.70 (1H, dd, J=2 Hz, J=13.5 Hz), 1.07 (3H, s), 1.06 (3H, t), 0.80 (3H, s)

| | Elemental analysis | | | |
|---|---|---|---|---|
| | C | H | N | O |
| % Found | 76.63 | 7.75 | 4.62 | |
| % Calculated | 76.73 | 7.80 | 4.71 | 10.76 |

7-Bromo-3,3-dimethyl-5-(3-pyridyl N-oxide)-2,3-dihydro-1-benzoxepine C$_{17}$H$_{16}$BrNO$_2$ MM=346.223

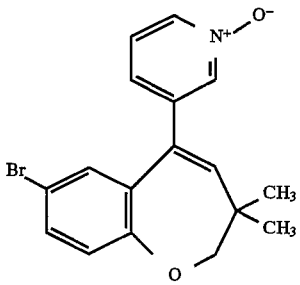

Formula 122

M.p.=161°–162° C.; ethyl acetate; 50%]IR in cm$^{-1}$: 3090, 2950, 1580, 1540, 1460 $^1$H NMR (CDCl$_3$) in ppm: 8.19 (2H, m), 7.23 (3H, m), 6.90 (2H, m), 5.77 (1H, s), 3.90 (2H, s), 1.17 (6H, s)

| | Elemental analysis | | | |
|---|---|---|---|---|
| | C | H | Br | N | O |
| % Found | 59.07 | 4.72 | 22.99 | 4.13 | |
| % Calculated | 58.97 | 4.66 | 23.06 | 4.05 | 9.26 |

7-Cyano-3,3-dimethyl-5-(3-pyridyl N-oxide)-2,3-dihydro-1-benzoxepine C$_{18}$H$_{16}$N$_2$O$_2$ MM=292.337

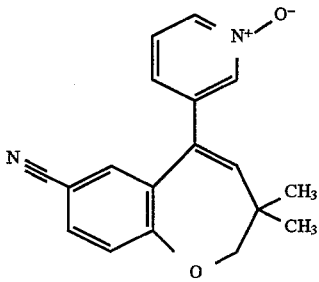

Formula 123

M.p.=162°–164° C.; ethyl acetate; 45%]IR in cm$^{-1}$: 3070, 2960, 2230, 1600 $^1$H ,NMR (CDCl$_3$) in ppm: 8.17 (2H, m), 7.25 (5H, m), 5.85 (1H, s), 3.92 (2H, s), 1.15 (6H, s)

| | Elemental analysis | | | |
|---|---|---|---|---|
| | C | H | N | O |
| % Found | 73.89 | 5.52 | 9.68 | |
| % Calculated | 73.95 | 5.52 | 9.58 | 10.95 |

7,8-Dichloro-3,3-dimethyl-5-(3-pyridyl N-oxide)-2,3-dihydro-1-benzoxepine C$_{17}$H$_{15}$Cl$_2$NO$_2$ MM=336.217

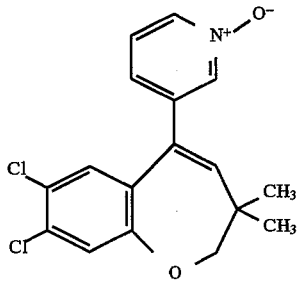

Formula 124

[137°–139° C.; isooctane and diisopropyl ether: 50/50; 46%]IR in cm$^{-1}$: 3120, 3030, 2950, 1590, 1540 $^1$H NMR (CDCl$_3$) in ppm: 8.20 (2H, m), 7.16 (3H, m), 6.80 (1H, s), 5.79 (1H, s), 3.90 (2H, s), 1.19 (6H, s)

| | Elemental analysis | | | |
|---|---|---|---|---|
| | C | H | Cl | N | O |
| % Found | 66.70 | 4.54 | 21.24 | 4.05 | |
| % Calculated | 60.73 | 4.50 | 21.09 | 4.17 | 9.52 |

3,3-Dimethyl-5-(2-pyridyl N-oxide)-2,3-dihydro-1-benzoxepine-7-carboxamide C$_{18}$H$_{18}$N$_2$O$_3$ MM=310.352

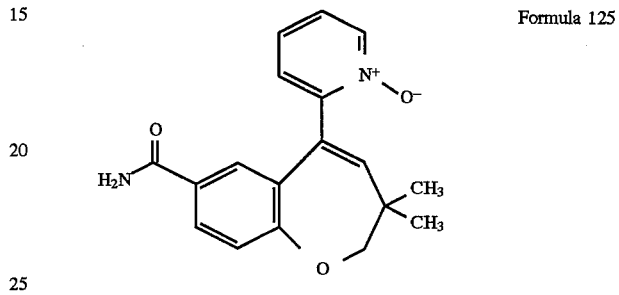

Formula 125

[M.p.=215°–217° C.; methanol; 28%]IR in cm$^{-1}$: 3400, 3200, 2970, 1665, 1605 $^1$H NMR (DMSO) in ppm: 8.16 (1H, m), 7.35 (6H, m), 5.85 (1H, s), 3.93 (2H, s), 1.13 (6H, s).

| | Elemental analysis | | | |
|---|---|---|---|---|
| | C | H | N | O |
| % Found | 69.49 | 5.84 | 8.80 | |
| % Calculated | 69.66 | 5.85 | 9.03 | 15.47 |

3,3-Dimethyl-7-phenylsulfonyl-5-(2-pyridyl N-oxide)-2,3-dihydro-1-benzoxepine C$_{23}$H$_{21}$NO$_4$S MM=407.490

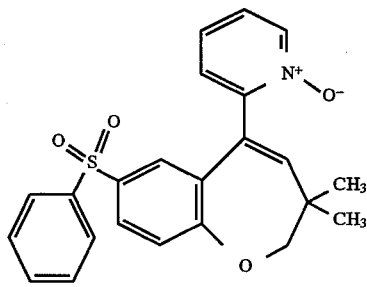

Formula 126

[M.p.=167°–169° C.; diisopropyl ether; 19%]IR in cm$^{-1}$: 3060, 2950, 1600, 1560, 1490 $^1$H NMR (CDCl$_3$) in ppm: 8.20 (1H, m), 7.38 (11H, m), 5.93 (1H, s), 3.99 (2H, s), 1.19 (6H, s)

| | Elemental analysis | | | | |
|---|---|---|---|---|---|
| | C | H | N | O | S |
| % Found | 67.84 | 5.34 | 3.42 | 15.57 | 7.83 |
| % Calculated | 67.79 | 5.20 | 3.44 | 15.71 | 7.87 |

7-Chloro-8-ethyl-3,3-dimethyl-5-(2-pyridyl N-oxide)-2,3-dihydro-1-benzoxepine $C_{19}H_{20}ClNO_2$ MM=329.829

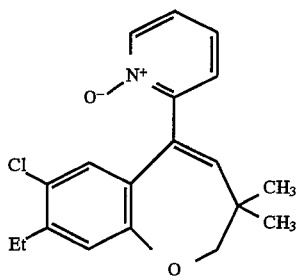

Formula 127

[M.p.=144°–146° C.; ethyl acetate; 34%]IR in $cm^{-1}$: 3070, 2950, 1485 $^1$H NMR (CDCl$_3$) in ppm: 8:23 (1H, m), 7.20 (3H, m), 6.87 (1H, s), 6.50 (1H, s), 5.78 (1H, s), 3.95 (2H, s), 2.62 (2H, q), 1.18 (3H, t), 1.15 (6H, s)

| | Elemental analysis | | | | |
|---|---|---|---|---|---|
| | C | H | Cl | N | O |
| % Found | 69.25 | 6.01 | 10.89 | 4.26 | |
| % Calculated | 69.19 | 6.11 | 10.75 | 4.25 | 9.70 |

8-Bromo-3,3-dimethyl-1-(2-pyridyl N-oxide)-3H-benzo[f]-cyclohepta-1,4-diene $C_{18}H_{16}BrNO$ MM=342.235

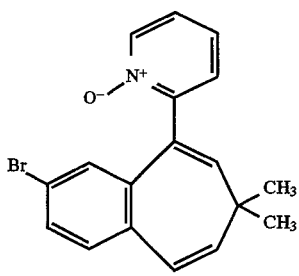

Formula 128

[M.p.=167° C.; diisopropyl ether; 10%]IR in $cm^{-1}$: 3080, 2980, 1485 $^1$H NMR (CDCl$_3$) in ppm: 8.11 (1H, m), 7.15 (6H, m), 6.52 (1H,d,J=10 Hz), 5.88 (1H, s), 5.75 (1H, d, J=10 Hz), 1.11 (6H, s).

| | Elemental analysis | | | | |
|---|---|---|---|---|---|
| | C | H | Br | N | O |
| % Found | 63.16 | 4.56 | 23.05 | 4.09 | |
| % Calculated | 63.17 | 4.71 | 23.35 | 4.09 | 4.68 |

3,3-Dimethyl-7-(2-methylpropyl)-5-(2-pyridyl-N-oxide)-2,3-dihydro-1-benzoxepine $C_{21}H_{25}NO_2$ MM=323.434

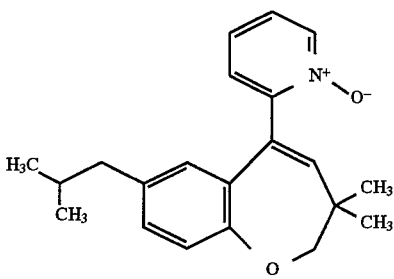

FORMULA 130

[M.p.=114°–116° C.; diisopropyl ether;, 25%]IR in $cm^{-1}$: 3060; 2960; 1500; 1490 $^1$NMR (CDCl$_3$) in ppm:8.20(1H, m); 7.20(3H, m); 6.86(2H, m); 6.30(1H, s); 5.76(1H, s); 3.95(2H, s); 2.22(2H, d); 1.68(1H, m); 1.16(6H, s); 0.8(3H, s); 0.58(3H, s).

| | Elemental analysis | | | |
|---|---|---|---|---|
| | C | H | N | O |
| % Found | 77,92 | 7,55 | 4,42 | |
| % Calculated | 77,98 | 7,79 | 4,33 | 9,89 |

7-Chloro-3,3,8-trimethyl-5-(2-pyridyl-N-oxide)-2,3-dihydro-1-benzoxepine $C_{18}H_{18}ClNO_2$ MM=315,803

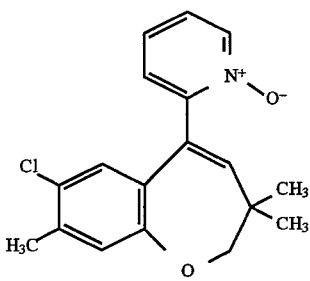

FORMULA 131

[M.p.=178°–180° C.; ethyl acetate 20%]IR in $cm^{-1}$: 3060; 2960; 1610; 1490 $^1$H NMR (CDCl$_3$) in ppm: 8.19(1H, m); 7.20(3H, m); 6.85(1H, s); 6.49(1H,s); (1H, s); 5.75(1H, s); 3.92(2H, s); 2.22(3H, s): 1.15(6H, s).

| | Elemental analysis | | | | |
|---|---|---|---|---|---|
| | C | H | Cl | N | O |
| % Found | 68,74 | 5,73 | 11,48 | 4,42 | |
| % Calculated | 68,48 | 5,75 | 11,23 | 4,44 | 10,13 |

7-Bromo-8-chloro-3,3-dimethyl-5-(2-pyridyl-N-oxyde)-2,3-dihydro-1-benzoxepine $C_{17}H_{15}BrClNO_2$ MM=380,672

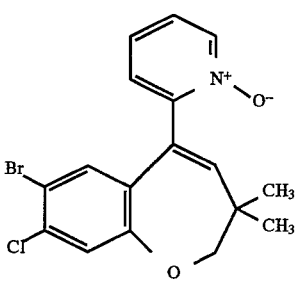

FORMULA 132

[M.p.=182°–183° C.; ethyl acetate; 44%]IR in $cm^{-1}$: 3060; 2950; 1580; 1540; 1470 $^1$NMR (CDCl$_3$) in ppm: 8.22(1H, m); 7.22(3H, m); 7.08(1H, s); 6.72(1H, s); 5.83(1H, s); 3.95(2H, s); 1.17(6H, s).

| | Elemental analysis | | | | | |
|---|---|---|---|---|---|---|
| | C | H | Br | Cl | N | O |
| % Found | 53,72 | 3,87 | 20,89 | 9,46 | 3,75 | |
| % Calculated | 53,63 | 3,97 | 20,99 | 9,31 | 3,68 | 8,41 |

8-Chloro-7-cyano-3,3-dimethyl-5-(2-pyridyl-N-oxide)-2,3-dihydro-1-benzoxepine $C_{18}H_{15}ClN_2O_2$ MM=326,786

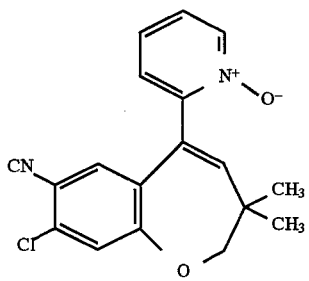

FORMULA 133

[M.p.=206°–207° C.; ethyl acetate; 53%]IR in $cm^{-1}$: 3080; 2990; 2240; 1600; 1550; 1490 $^1$(CDCl$_3$) in ppm: 8.20(1H, m); 7.23(3H, m); 7.13 (1H, s): 6.83(1H, s); 5.93(1H, s); 4.02(2H, s); 1.20(6, s).

| | Elemental analysis | | | | |
|---|---|---|---|---|---|
| | C | H | Cl | N | O |
| % Found | 65,51 | 4,56 | 10,89 | 8,48 | |
| % Calculated | 66,16 | 4,63 | 10,85 | 8,57 | 9,79 |

8-Chloro-3,3-dimethyl-5-(2-pyridyl-N-oxide)-7-trifluoromethyl-2,3-dihydro-1-benzoxepine $C_{18}H_{15}ClF_3NO_2$ MM=369,774

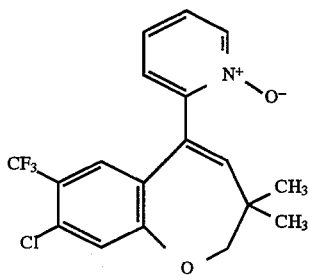

FORMULA 134

[M.p.=158°–161° C.]IR in $cm^{-1}$: 3080; 2980; 1610; 1565; 1495 $^1$NMR (CDCl$_3$) in ppm: 8.18(1H, m); 7.58(4H, m); 6.80(1H, s); 5.88(1H, s); 3.98(2H, s); 1.15(6H, s).

| | Elemental analysis | | | | | |
|---|---|---|---|---|---|---|
| | C | H | Cl | F | N | O |
| % Found | 58,42 | 4,24 | 9,99 | 14,79 | 3,83 | |
| % Calculated | 58,46 | 4,09 | 9,59 | 15,42 | 3,79 | 8,65 |

8-Bromo-3,3-dimethyl-1-(2-pyridyl-N-oxide)4,5-dihydro-3H-benzo[f]-cyclohept-1-ene $C_{18}H_{18}BrNO$ MM=344,250

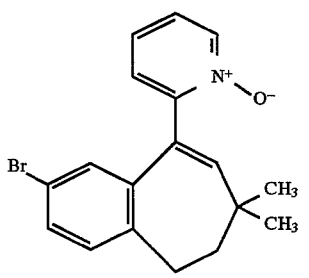

FORMULA 135

[M.p.=173°–175° C.; toluene; 43%]IR in $cm^{-1}$: 3070; 2960; 1590; 1490 $^1$H NMR (CDCl$_3$) in ppm: 8.11(1H, m); 7.18 (5H, m); 6.73(1H, d); 5.90(1H, s); 2.59(2H, m); 1.85(2H, m); 1.09(6H, s).

| | Elemental analysis | | | | |
|---|---|---|---|---|---|
| | C | H | Br | N | O |
| % Found | 62,80 | 5,25 | 23,26 | 3,93 | |
| % Calculated | 62,80 | 5,27 | 23,21 | 4,07 | 4,65 |

3,3-Dimethyl-8-phenylsulfonyl-1-(2-pyridyl-N-oxide)-4,5-dihydro-3H-benzo[f]cyclohept-1-ene $C_{24}H_{23}NO_3S$ MM=405,517

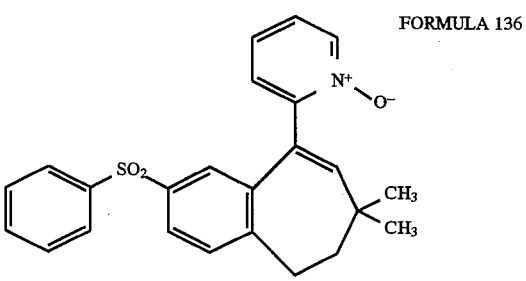

FORMULA 136

[M.p.=191°–192° C.; isopropanol; 45%]IR in $cm^{-1}$: 3060; 2950; 1595; 1585; 1560; 1485 $^1$H NMR (CDCl$_3$) in ppm: 8.08(1H, m); 7.45(11H, m); 5.95(1H, s); 2.92(2H, m); 1.88(2H, m); 1.10(6H, s).

| | Elemental analysis | | | | |
|---|---|---|---|---|---|
| | C | H | N | O | S |
| % Found | 70,86 | 5,82 | 3,34 | | 7,83 |
| % Calculated | 71,08 | 5,72 | 3,45 | 11,84 | 7,91 |

7,8-Dichloro-3,3-dimethyl-1-(2-pyridyl-N-oxide)-4,5-dihydro-3H-benzo[f]cyclohept- 1-ene $C_{18}H_{17}Cl_2NO$ MM=334,252

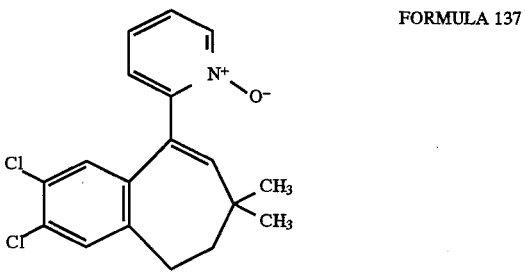

FORMULA 137

[M.p.=195°–196° C.; toluene; 25%]IR in $cm^{-1}$: 3070; 2970; 1550; 1480 $^1$H NMR (CDCl$_3$) in ppm: 8.12(1H, m); 7.25 (4H, m); 6.68(1H, s); 5.92(1H, s); 2.61(2H, m); 1.85(2H, m); 1.11(6H, s).

| | Elemental analysis | | | | |
|---|---|---|---|---|---|
| | C | H | Cl | N | O |
| % Found | 64,32 | 5,17 | 21,10 | 4,31 | |
| % Calculated | 64,38 | 5,13 | 21,22 | 4,19 | 4,79 |

8-Bromo-4,4-dimethyl-1-(2-pyridyl-N-oxide)-3,4-dihydro-3H-benzo[f]cyclohept-1-ene C$_{18}$H$_{18}$BrNO MM=334.250

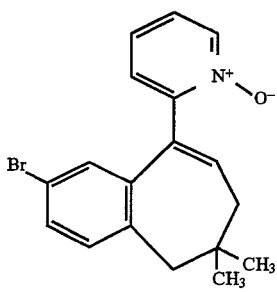

FORMULA 138

[M.p.=137°–139° C.; diisopropyl ether, 20%]IR in cm$^{-1}$: 2960; 2930; 1610; 1590; 1550; 1490 $^1$H NMR (CDCl$_3$) in ppm: 8.12(1H, m); 7.12(6H, m); 6.51(1H, d); 2.58(2H, s); 1.74(2H, d); 1.05(6H, s).

| Elemental analysis | | | | |
|---|---|---|---|---|
| | C | H | Br | N | O |
| % Found | 62,80 | 5,14 | 23,27 | 4,04 | |
| % Calculated | 62,80 | 5,27 | 23,21 | 4,07 | 4,65 |

Hemisulfate of 7-fluoro-3,3-dimethyl-5(2-pyridyl-N-oxide)-2,3-dihydro-1-benzoxepine C$_{17}$H$_{17}$FNO$_4$S$_{0,5}$ MM=334,357

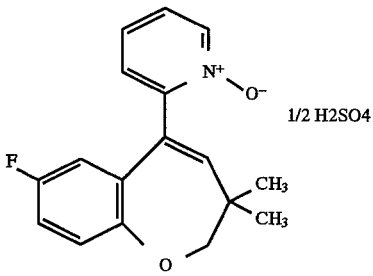

FORMULA 139

[M.p.=198°–199° C.; ethanol; 33%]IR in cm$^{-1}$: 3090; 2970; 1620; 1580; 1500 $^1$NMR (CDCl$_3$) in ppm: 10.28(1H, s); 8.36(1H, m); 7.55(3H, m); 6.99(2H, m); 6.07(2H, m); 3.90 (2H, s); 1.14(6H, s).

| Elemental analysis | | | | | |
|---|---|---|---|---|---|
| | C | H | F | N | O | S |
| % Found | 61,06 | 5,45 | 5,46 | 4,19 | | 5,01 |
| % Calculated | 61,07 | 5,12 | 5,68 | 4,19 | 19,14 | 4,80 |

Hydrochloride of 7,8-dichloro-3,3-dimethyl-5-(2-pyridyl-N-oxide)-2,3-dihydro-1-benzoxepine C$_{17}$H$_{16}$Cl$_3$NO$_2$ MM=372,690

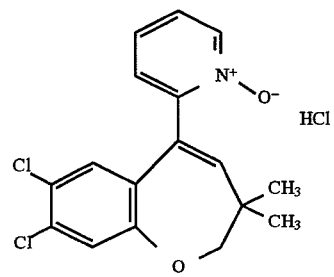

FORMULA 140

[M.p.=182°–186° C.; acetone; 60%]IR in cm$^{-1}$: 3090; 2970; 2270; 1700; 1605; 1525 $^1$NMR (CDCl$_3$) in ppm: 11.78(1H, s); 8.43(1H, m); 7.63(3H, m); 7.26(1H, s); 6.55(1H, s); 6.00(1H, s); 3.95(2H, s); 1.15(6H, s).

| Elemental analysis | | | | |
|---|---|---|---|---|
| | C | H | Cl | N | O |
| % Found | 54,74 | 4,24 | 27,89 | 3,90 | |
| % Calculated | 54,78 | 4,33 | 28,54 | 3,76 | 8,59 |

EXAMPLE 9

4-(4-Fluorophenoxy)-3,3-dimethyl-butanoic acid C$_{12}$H$_{15}$FO$_3$ MM=226.247

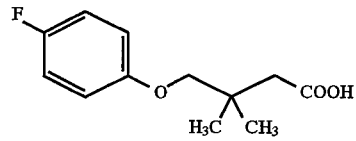

Formula 141

A suspension of 4-fluorophenol(21.3 g; 0.19 mol) and sodium hydroxide (7.6 g; 0.19 mol) in n-butanol under a flow of dry nitrogene is heated by an oil bath at 190° C. during 10 minutes. The reactor is equipped with a distillation system for the elimination of the formed water by azeotropic removal. The heating is continued to distill all of the n-butanol. Then the 3,3-dimethylbutyrolacetone (22.8 g; 0.20 mol) is added. The reaction medium is heated 10 hours at 160° C. (temperature inside the medium), then cooled to 80° C. for the addition of water (65 ml). The obtained solution is washed with dichloromethane and decanted. The aqueous phase is acidified and the desired acid is extracted with dichloromethane dried over anhydrous sodium sulfate. The solution is concentrated under reduced pressure and the oily residue is distilled.

[B.p.(53.2 Pa =0.4 mm Hg)=130°–134° C.; 75%]
IR in cm$^{-1}$: 3480; 2200; 1705; 1600; 1505 $^1$H NMR (CDCl$_3$) in ppm: 10.75 (1H, m); 6.82 (4H, m); 3.66 (2H, S); 2.40 (2H, S); 1.11 (6H, S).

We claim:

1. A Compound of formula I:

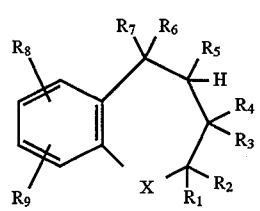

in which:

X represents CHR, R being a hydrogen atom,

R$_1$, R$_2$, R$_3$ and R$_4$, which are identical or different, represent a hydrogen atom or a C$_1$–C$_7$ alkyl group;

$R_5$ represents a hydrogen atom, a hydroxyl group or $R_5$, taken together with $R_7$, forms a bond;

$R_6$ represents a pyridyl group or its n-oxide optionally substituted on the carbon atoms by 1 to 7 groups chosen from hydroxyl, nitro, cyano, $C_1$–$C_7$ alkyl or $C_1$–$C_7$ alkoxy;

$R_7$ represents a hydrogen atom or a hydroxyl, $C_1$–$C_7$ alkoxy or $C_1$–$C_7$ acyloxy group or $R_5$ and $R_7$ together form a bond;

$R_8$ and $R_9$, which are identical or different, represent a hydrogen or halogen atom, a hydroxyl, nitro, cyano, trifluoromethyl, trifluoromethoxy, pentafluoroethyl, $C_1$–$C_7$ alkyl, $C_1$–$C_7$ alkoxy, $C_1$–$C_7$ alkylthio, $C_1$–$C_7$ acylthio, $C_1$–$C_7$ alkylsulfonyl or $C_1$–$C_7$ alkylsulfinyl group, a group of formulae:

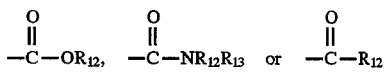

in which $R_{12}$ and $R_{13}$, which are identical or different, represent a hydrogen atom or a $C_1$–$C_7$ alkyl group, or $R_8$ and $R_9$ represent a $C_6$–$C_{10}$ aryl, ($C_6$–$C_{10}$) -arylsulfonyl or ($C_6$–$C_{10}$) arylsulfinyl group, optionally substituted by one to six substituents chosen from halo, hydroxyl, nitro, cyano, carboxyl, carbamoyl, trifluoromethyl, trifluoromethoxy, pentafluoroethyl, $C_1$–$C_7$ alkyl, $C_1$–$C_7$ alkoxy, $C_1$–$C_7$ alkylthio, $C_1$–$C_7$ acylthio, $C_1$–$C_7$ alkylsulfonyl or $C_1$–$C_7$ alkylsulfinyl, and N-oxides and pharmaceutically acceptable salts thereof.

2. A compound of formula I according to claim 1, wherein $R_1$ and $R_2$ represent a hydrogen atom.

3. A compound of formula I according to claim 1, wherein $R_5$ represents a hydrogen atom.

4. A compound of formula I according to claim 1, wherein $R_6$ is chosen from 2-pyridyl, 2-pyridyl N-oxide, 3-pyridyl, 3-pyridyl N-oxide, 4-pyridyl, 3-hydroxy-4-pyridyl, 2 optionally substituted on the carbon atoms by 1 to 3 substituents chosen from hydroxyl, nitro, cyano, $C_1$–$C_7$ alkyl and $C_1$–$C_7$ alkoxy.

5. A compound of formula I according to claim 1, wherein, $R_7$ represents a hydrogen atom or a hydroxyl, methoxy or acetoxy group.

6. A compound according to claim 1 of the formula:

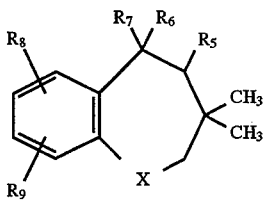

in which X represents CHR, and R, $R_5$, $R_6$, $R_7$, $R_8$ and $R_9$ are as defined in claim 1.

7. A compound according to claim 1 of the formula:

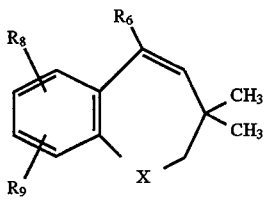

in which X represents CHR, and R, $R_6$, $R_8$ and $R_9$ are as defined in claim 1.

8. The compound 8-cyano-3,3-dimethyl-1-(2-pyridyl N-oxide)-4,5-dihydro -3H-benzocycloheptane.

9. Pharmaceutical composition comprising, as active ingredient, an effective amount of a compound according to claim 1 and a pharmaceutically acceptable carrier.

* * * * *